United States Patent [19]
Watanabe et al.

[11] Patent Number: 6,147,051
[45] Date of Patent: Nov. 14, 2000

[54] METHODS AND COMPOSITIONS FOR THE PROPHYLACTIC AND/OR THERAPEUTIC TREATMENT OF ORGAN HYPOFUNCTION

[75] Inventors: Toshifumi Watanabe; Mitsuhiro Wakimasu; Chieko Kitada, all of Osaka, Japan

[73] Assignee: Takeda Chemical Industries Ltd., Osaka, Japan

[21] Appl. No.: 08/561,096

[22] Filed: Nov. 21, 1995

Related U.S. Application Data

[63] Continuation of application No. 08/231,017, Apr. 21, 1994, abandoned.

[30] Foreign Application Priority Data

Apr. 21, 1993 [JP] Japan ................................. 5-094332

[51] Int. Cl.$^7$ .................................................. A61K 38/12
[52] U.S. Cl. .................................. 514/11; 514/9; 514/13; 514/2
[58] Field of Search ........................ 514/11, 9, 13, 514/2

[56] References Cited

U.S. PATENT DOCUMENTS

| | | | |
|---|---|---|---|
| 5,214,130 | 5/1993 | Patchett et al. | 530/317 |
| 5,240,910 | 8/1993 | Lam et al. | 530/317 |
| 5,514,696 | 5/1996 | Murugesan et al. | 514/380 |
| 5,654,309 | 8/1997 | Furuya et al. | 514/258 |

FOREIGN PATENT DOCUMENTS

| | | |
|---|---|---|
| 0 496 452 A1 | 1/1991 | European Pat. Off. |
| 425 134 A1 | 5/1991 | European Pat. Off. |
| 0 436 189 A1 | 7/1991 | European Pat. Off. |
| 0 457 195 A2 | 11/1991 | European Pat. Off. |
| 0 460 679 A2 | 12/1991 | European Pat. Off. |
| 0 499 266 A1 | 8/1992 | European Pat. Off. |
| 0 555 537 A2 | 11/1992 | European Pat. Off. |
| 0 526 708 A1 | 2/1993 | European Pat. Off. |
| 0 528 312 A2 | 2/1993 | European Pat. Off. |
| 0 558 258 A1 | 2/1993 | European Pat. Off. |
| 569193 A1 | 4/1993 | European Pat. Off. |
| 0 552 489 A2 | 7/1993 | European Pat. Off. |
| 0 577 957 A1 | 1/1994 | European Pat. Off. |
| 0 608 565 A1 | 8/1994 | European Pat. Off. |
| 4-288099 | 10/1992 | Japan . |
| 5-178890 | 7/1993 | Japan . |
| 5-279390 | 10/1993 | Japan . |
| 5-279390 | 2/1994 | Japan . |
| WO 92/12991 | 1/1991 | WIPO . |
| WO 91/13089 | 9/1991 | WIPO . |
| WO 92/20706 | 11/1992 | WIPO . |
| WO 9317701 A1 | 3/1993 | WIPO . |
| WO 93/08799 | 5/1993 | WIPO . |
| WO 93/13218 | 7/1993 | WIPO . |
| WO 93/21219 | 10/1993 | WIPO . |
| WO 93/23404 | 11/1993 | WIPO . |

OTHER PUBLICATIONS

Beatley's Textbook of Pharmaceutics, 8$^{th}$ ed., pp. 641–655.
Furuya et al, Abs. No. (AN 121: 205 395) equivalent to EP 608565.
Kurihara et al, Life Sciences, vol. 51, op. PL 101–106, (1992).
Housset et al, PNAS, USA, vol. 90, pp. 9266–9270, (Oct. 1993).
The Merck Manual, (1992), p. 875.
B. Mugrage et al., "Bioorganic & Medicinal Chemistry Letters", Mon Press pp. 2100–2104.
The 11th Cytoprotection Research Meeting Program/Abstracts, Feb. 2, 1993, pp. 1–4 (english translation) Caretaker on Duty: Keiichi Kawai.
149. RENAL FAILURE –ACUTE RENAL FAILURE (ARF); Genitourinary Disorders, Chapter 149; pp. 1661–1665.

*Primary Examiner*—Keith D. MacMillan
*Assistant Examiner*—T. D. Wessendorf
*Attorney, Agent, or Firm*—Dike, Bronstein, Roberts & Cushman, LLP; David G. Conlin; George W. Neuner

[57] ABSTRACT

Compounds having antagonistic activity on endothelin receptors can be effectively used for prophylaxis and/or treatment of hypofunction of organs which occurs in their surgery or transplant.

6 Claims, No Drawings

```
                           SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
          (A) LENGTH: 21 amino acids
          (B) TYPE: amino acid
          (D) TOPOLOGY: linear (ii) MOLECULE TYPE: peptide (ix) FEATURE:
          (A) NAME/KEY: Disulfide-bond
          (B) LOCATION: 1..15

(ix) FEATURE:
          (A) NAME/KEY: Disulfide-bond
          (B) LOCATION: 3..11

(xi) SEQUENCE DESCRIPTION: SEQ ID NO:1:

Cys Ser Cys Ser Ser Leu Met Asp Lys Glu Cys Val Tyr Phe Cys His
1               5                   10                  15

Leu Thr Leu Ile Trp
            20

(2) INFORMATION FOR SEQ ID NO:2:

(i) SEQUENCE CHARACTERISTICS:
          (A) LENGTH: 21 amino acids
          (B) TYPE: amino acid
          (D) TOPOLOGY: linear (ii) MOLECULE TYPE: peptide
```

(ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:2:

Cys Ser Cys Ser Ser Leu Met Asp Lys Glu Cys Val Tyr Phe Cys His
1               5                  10                  15

Leu Thr Xaa Ile Trp
            20

(2) INFORMATION FOR SEQ ID NO:3:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:3:

Cys Ser Cys Ser Ser Leu Met Asp Lys Glu Cys Val Tyr Phe Cys His
1               5                  10                  15

Leu Thr Phe Ile Trp
            20

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(ix) FEATURE:
        (A) NAME/KEY: Modified-site
        (B) LOCATION: 19

(xi) SEQUENCE DESCRIPTION: SEQ ID NO:4:

Cys Ser Cys Ser Ser Leu Met Asp Lys Glu Cys Val Tyr Phe Cys His
1               5                  10                  15

Leu Thr Xaa Ile Trp
            20

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: linear

```
    (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:5:

Cys Ser Cys Ser Ser Leu Met Asp Lys Glu Cys Val Tyr Phe Cys His
1               5                   10                  15

Leu Thr Asn Ile Trp
            20

(2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:6:

Cys Ser Cys Ser Ser Leu Met Asp Lys Glu Cys Val Tyr Phe Cys His
1               5                   10                  15

Leu Ser Leu Ile Trp
            20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:7:

Cys Ser Cys Ser Ser Leu Met Asp Lys Glu Cys Val Tyr Phe Cys His
1               5                   10                  15

Leu Asn Leu Ile Trp
            20

(2) INFORMATION FOR SEQ ID NO:8:

(i) SEQUENCE CHARACTERISTICS:
        (A) LENGTH: 21 amino acids
        (B) TYPE: amino acid
        (D) TOPOLOGY: linear (ii) MOLECULE TYPE: peptide
```

(ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:8:

Cys Ser Cys Ser Ser Leu Met Asp Lys Glu Cys Val Tyr Phe Cys His
1               5                   10                  15

Leu Gly Leu Ile Trp
            20

(2) INFORMATION FOR SEQ ID NO:9:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:9:

Cys Thr Cys Phe Thr Tyr Lys Asp Lys Glu Cys Val Tyr Tyr Cys His
1               5                   10                  15

Leu Thr Leu Ile Trp
            20

(2) INFORMATION FOR SEQ ID NO:10:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:10:

Cys Ser Cys Ser Ser Leu Met Asp Ala Glu Cys Val Tyr Phe Cys His
1               5                   10                  15

Leu Thr Leu Ile Trp
            20

(2) INFORMATION FOR SEQ ID NO:11:

(i) SEQUENCE CHARACTERISTICS:
        (A) LENGTH: 21 amino acids
        (B) TYPE: amino acid
        (D) TOPOLOGY: linear (ii) MOLECULE TYPE: peptide

```
        (ix) FEATURE:
              (A) NAME/KEY: Disulfide-bond
              (B) LOCATION: 1..15

(ix) FEATURE:
              (A) NAME/KEY: Disulfide-bond
              (B) LOCATION: 3..11

(ix) FEATURE:
              (A) NAME/KEY: Modified-site
              (B) LOCATION: 1

(xi) SEQUENCE DESCRIPTION: SEQ ID NO:11:

Xaa Ser Cys Ser Ser Leu Met Asp Lys Glu Cys Val Tyr Phe Cys His
1               5                  10                  15

Leu Thr Leu Ile Trp
            20

(2) INFORMATION FOR SEQ ID NO:12:

(i) SEQUENCE CHARACTERISTICS:
              (A) LENGTH: 21 amino acids
              (B) TYPE: amino acid
              (D) TOPOLOGY: linear (ii) MOLECULE TYPE: peptide (ix) FEATURE:
              (A) NAME/KEY: Disulfide-bond
              (B) LOCATION: 1..15

(ix) FEATURE:
              (A) NAME/KEY: Disulfide-bond
              (B) LOCATION: 3..11

(xi) SEQUENCE DESCRIPTION: SEQ ID NO:12:

Cys Ala Cys Ser Ser Leu Met Asp Lys Glu Cys Val Tyr Phe Cys His
1               5                  10                  15

Leu Thr Leu Ile Trp
            20

(2) INFORMATION FOR SEQ ID NO:13:

(i) SEQUENCE CHARACTERISTICS:
              (A) LENGTH: 21 amino acids
              (B) TYPE: amino acid
              (D) TOPOLOGY: linear (ii) MOLECULE TYPE: peptide (ix) FEATURE:
              (A) NAME/KEY: Disulfide-bond
              (B) LOCATION: 1..15

(ix) FEATURE:
              (A) NAME/KEY: Disulfide-bond
              (B) LOCATION: 3..11

(xi) SEQUENCE DESCRIPTION: SEQ ID NO:13:

Cys Ser Cys Ala Ser Leu Met Asp Lys Glu Cys Val Tyr Phe Cys His
1               5                  10                  15

Leu Thr Leu Ile Trp
            20

(2) INFORMATION FOR SEQ ID NO:14:

(i) SEQUENCE CHARACTERISTICS:
              (A) LENGTH: 21 amino acids
              (B) TYPE: amino acid
              (D) TOPOLOGY: linear
```

(ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:14:

Cys Ser Cys Ser Ala Leu Met Asp Lys Glu Cys Val Tyr Phe Cys His
1               5                   10                  15

Leu Thr Leu Ile Trp
            20

(2) INFORMATION FOR SEQ ID NO:15:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:15:

Cys Ser Cys Ser Ser Ala Met Asp Lys Glu Cys Val Tyr Phe Cys His
1               5                   10                  15

Leu Thr Leu Ile Trp
            20

(2) INFORMATION FOR SEQ ID NO:16:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
        (A) NAME/KEY: Disulfide-bond
        (B) LOCATION: 1..15

(ix) FEATURE:
        (A) NAME/KEY: Disulfide-bond
        (B) LOCATION: 3..11

(xi) SEQUENCE DESCRIPTION: SEQ ID NO:16:

Cys Ser Cys Ser Ser Leu Ala Asp Lys Glu Cys Val Tyr Phe Cys His
1               5                   10                  15

Leu Thr Leu Ile Trp
            20

(2) INFORMATION FOR SEQ ID NO:17:

(i) SEQUENCE CHARACTERISTICS:
        (A) LENGTH: 21 amino acids
        (B) TYPE: amino acid
        (D) TOPOLOGY: linear (ii) MOLECULE TYPE: peptide -continued

```
    (ix) FEATURE:
         (A) NAME/KEY: Disulfide-bond
         (B) LOCATION: 1..15

(ix) FEATURE:
         (A) NAME/KEY: Disulfide-bond
         (B) LOCATION: 3..11

(xi) SEQUENCE DESCRIPTION: SEQ ID NO:17:

Cys Ser Cys Ser Ser Leu Xaa Asp Lys Glu Cys Val Tyr Phe Cys His
1               5                  10                  15

Leu Thr Leu Ile Trp
            20

(2) INFORMATION FOR SEQ ID NO:18:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
         (A) NAME/KEY: Disulfide-bond
         (B) LOCATION: 1..15

(ix) FEATURE:
         (A) NAME/KEY: Disulfide-bond
         (B) LOCATION: 3..11

(xi) SEQUENCE DESCRIPTION: SEQ ID NO:18:

Cys Ser Cys Ser Ser Trp Leu Asp Lys Glu Cys Val Tyr Phe Cys His
1               5                  10                  15

Leu Thr Leu Ile Trp
            20
```

METHODS AND COMPOSITIONS FOR THE PROPHYLACTIC AND/OR THERAPEUTIC TREATMENT OF ORGAN HYPOFUNCTION

This application is a continuation of copending application Ser. No. 08/231,017 filed on Apr. 21, 1994 now abandoned.

FIELD OF THE INVENTION

The present invention relates to prophylactic and/or therapeutic compositions for the treatment of hypofunction of organs, particularly hypofunction caused by surgery or on or transplant of the organ, the composition comprising a pharmacological carrier containing an effective amount of compounds having antagonistic activity on endothelin receptors.

DESCRIPTION OF THE PRIOR ART

Endothelin (ET) is a vasoconstrictive peptide composed of 21 amino acid residues. Endothelin was isolated from the culture supernatant of the endothelial cells of porcine aortas. Its structure was determined by M. Yanagisawa et al. in 1988 [M. Yanagisawa et al., *Nature* 332, 411–412 (1988)]. More recently, the research on genes coding for endothelin has revealed the presence of three kinds of peptides similar to endothelin in structure. These peptides are named endothelin-1 (ET-1), endothelin-2 (ET-2) and endothelin-3 (ET-3), respectively. Further, the research has revealed that the endothelin receptors in vivo include two types, A and B.

Since the discovery of endothelin, compounds having antagonistic activity on endothelin receptors have been intensively searched in order to develop drugs for treating the following diseases resulting from endothelin. As a result, the compounds having antagonistic activity on endothelin receptors are proposed in Japanese Patent Application Nos. 4-344252, 4-216019, 4-27785 and 3-503831, EP-A-436, 189, EP-A-457,195, EP-A-510,526, WO92/12991, Japanese Patent Unexamined Publication No. 4-288099, EP-A-496, 452, EP-A-526,708, EP-A-460,679 and WO92/20706. The compounds described in these patents are suggested to be effective as therapeutic drugs for hypertension, cardiac or cerebral circulatory diseases, renal diseases and asthma, anti-inflammatory drugs, antarthritics and the like.

On the other hand, the endothelin concentration in organs such as the liver is known to increase in surgery of the organs [*Nippon Ishoku Gakkai Zasshi* 27 (1992)]. The recent research has revealed that monoclonal antibodies to endothelin have the action of preventing hypofunction of organs on which operations are conducted. However, it is neither described at all nor suggested that the compounds having antagonistic activity on endothelin receptors are useful as prophylactic and/or therapeutic drugs for hypofunction of organs in their surgery or transplant.

SUMMARY OF THE INVENTION

It is therefore an object of the present invention to provide prophylactic and/or therapeutic drugs for hypofunction of organs in their surgery or transplant comprising compounds having antagonistic activity on endothelin receptors.

The present inventors intensively studied to solve the above-mentioned problem. As a result, the present inventors discovered that the compounds having antagonistic activity on endothelin receptors which had hitherto been considered to be effective as therapeutic drugs for hypertension, cardiac or cerebral circulatory diseases, renal diseases and asthma, anti-inflammatory drugs and antarthritics were discovered to be unexpectedly effective as prophylactic and/or therapeutic drugs for hypofunction of organs in their surgery or transplant, particularly as prophylactic and/or therapeutic drugs for decreased liver function, completing the present invention by further studies.

In the present specification, amino acids and peptides are indicated by the abbreviations adopted by the IUPAC-IUB Commission on Biochemical Nomenclature or commonly used in the art. When specifically identified amino acids are capable of existing as optical isomers, the L-forms are represented unless otherwise specified. When reference is made in this specification to amino acids generically the amino acids can be in either D- or L-forms. For example, the following abbreviations are used to represent the identified L-amino acid:

Ala: Alanine
Arg: Arginine
Asn: Asparagine
Asp: Aspartic acid
Cys: Cysteine
Glu: Glutamic acid
Gln: Glutamine
Gly: Glycine
His: Histidine
Ile: Isoleucine
Leu: Leucine
Lys: Lysine
Met: Methionine
Phe: Phenylalanine
Pro: Proline
Ser: Serine
Thr: Threonine
Trp: Tryptophan
Tyr: Tyrosine
Val: Valine
Abu: 2-Aminobutyric acid
α-Aba: L-α-Aminobutanoic acid
Ac3c: 1-Aminocyclopropanecarboxylic acid
Ac4c: 1-Aminocyclobutanecarboxylic acid
Ac5c: 1-Aminocyclopentanecarboxylic acid
Ac6c: 1-Aminocyclohexanecarboxylic acid
Ac7c: 1-Aminocycloheptanecarboxylic acid
Acpr: 1-Aminocyclopropane-1-carboxylic acid
Acbu: 1-Aminocyclobutane-1-carboxylic acid
Acpe: 1-Aminocyclopentane-1-carboxylic acid
Achx: 1-Aminocyclohexane-1-carboxylic acid
Achp: 1-Aminocycloheptane-1-carboxylic acid
εAhx: ε-Aminocaproic acid
Aib: 2-Aminoisobutyric acid
aIle: Alloisoleucine
βAla: β-Alanine
Alg: 2-Amino-4-pentenoic acid (allylglycine)
Arg($NO_2$): $N^G$-Nitroarginine
Arg(Tos): $N^G$-p-Toluenesulfonylarginine
Asn($CH_2Ph$): $N^4$-Benzylasparagine
Asn ($CH_2CH_2Ph$): $N^4$-Phenethylasparagine
Asn($CH_2CH_2$-Ind): $N^4$-(2-{Indole-3-yl}ethyl)asparagine
Asn(Me.$CH_2CH_2Ph$): $N^4$-Methyl-$N^4$-phenethylasparagine Asn(CH₂CHMePh): N⁴-({2-phenyl}propyl)asparagine
Asp(R1): Aspartic acid β-4-phenylpiperazineamide
Asp(R2): Aspartic acid β-4-phenylpiperidineamide
Asp(R3): Aspartic acid β-indolineamide
Asp(R4): Aspartic acid β-1-aminoindaneamide
Asp(R5): Aspartic acid β-1-aminotetrahydronaphthaleneamide
Asp(R6): Aspartic acid β-4-acetylpiperazineamide
Atm: 2-Amino-3-(2-amino-5-thiazole)propanoic acid
Azc: Azetidine-2-carboxylic acid
Bip: (p-Phenyl)phenylalanine
Cta: Cysteic acid
Cpg: Cyclopentylglycine
Cpn: 2-Amino-3-cyclopropanepropanoic acid (cyclopropylalanine)
Chx: Cyclohexylalanine (hexahydroxyphenylalanine)
Cha: Cyclohexylalanine
C3al: L-3-Cyclopropylalanine
C4al: L-3-Cyclobutylalanine
C5al: L-3-Cyclopentylalanine
C6al: L-3-Cyclohexylalanine
CmGly: N-(Carboxymethyl)glycine
CpGly: N-Cyclopentylglycine
Cys(O₃H): L-Cysteic acid
Cys(O₃Na): Sodium L-cysteate
DCpg: D-2-Cyclopentylglycine
DChg: D-2-Cyclohexylglycine
DCys(O₃H): D-Cysteic acid
DCys(O₃Na): Sodium D-cysteate
DCys(O₃Bu₄N): Tert-butylammonium D-cysteate
DDpg: D-2-(1,4-Cyclohexadienyl)glycine
DEtg: (2S)-2-Ethyl-2-(2-thienyl)glycine
DFug: D-2-(2-Furyl)glycine
DGlu: D-Glutamic acid
DαAba: D-α-Aminobutanoic acid
DAsp: D-Aspartic acid
DAsp(ONa): Sodium D-aspartate
DBta: D-3-(3-Benzo[b]thienyl)alanine
DPen: D-Penicillamine
DTha: D-3-(2-Thienyl)alanine
DThg: D-2-(2-Thienyl)glycine
DThr: D-Threonine
DIle: D-Isoleucine
DaIle: D-Alloisoleucine
DItg: D-2-(Isothiazole)glycine
DLeu: D-Leucine
DtertLeu: D-2-Amino-3,3-dimethylbutanoic acid
DTrp: D-Tryptophan
DTrp(CHO): N^in-Formyl-D-tryptophan
DTrp(O): D-3-(2,3-Dihydro-2-oxoindole-3-yl)alanine
DTrp((CH₂)ₘCOR¹): D-Tryptophan substituted by —(CH₂)ₘ— COR¹ at the 1-position of the indole ring
DTyr: D-Tyrosine
DNal: D-3-(1-Naphthyl)alanine
DNva: D-Norvaline
DTza: D-3-(2-Thiazole)alanine
DTzg: D-2-(Thiazolyl)glycine
DVal: D-Valine
Dip: 3,3-Diphenylalanine
DAla: D-Alanine
DPhe: D-Phenylalanine
DPhg: D-Phenylglycine
Emg: 2-Amino-4,5(RS)-epoxy-4-pentenoic acid
GABA: γ-Aminobutyric acid
Gln(CH₂Ph): N⁵-Benzylglutamine
Gln (CH₂CH₂Ph): N⁵-Phenethylglutamine
Gln(CH₂CH₂-Ind): N⁵-(2-{Indole-3-yl}ethyl)glutamine
Glu(R3): Glutamic acid γ-indolineamide
Glu(R4): Glutamic acid γ-1-aminoindanamide
Glu(R5): Glutamic acid γ-1-aminotetrahydronaphthaleneamide
His(Bom): N(π)-Benzyloxymethylhistidine
His(Bzl): N(τ)-Benzylhistidine
3Hyp: 3-Hydroxyproline
Hyp: 4-Hydroxyproline
His(Dnp): N^im-2,4-Dinitrophenylhistidine
HomoPhe: 2-Amino-5-phenylpentanoic acid
Hyp(Bzl): 4-Benzyloxyproline
iPrGly: N-Isopropylglycine
IeGly: N-[2-(4-Imidazole)ethyl]glycine
Lys(CHO): N⁶-Formyl-L-lysine
Lys(Mtr): N(ε)-(4-Methoxy-2,3,6-trimethyl-benzenesulfonyl)lysine
tLeu: tert-Leucine
γLeu: γ-Methylleucine
MeAla: N-Methyl-L-alanine
MeLeu: N-Methyl-L-leucine
MeMet: N-Methyl-L-methionine
Met(O): Methionine sulfoxide
Met(O₂): Methionine sulfone
γMeLeu: γ-Methylleucine
Mpr: 3-Mercaptopropionic acid
Nva: Norvaline
Nle: Norleucine
Nal(1): 3-(1-Naphthyl)alanine
Nal(2): 3-(2-Naphthyl)alanine
N-MePhe: N-Methylphenylalanine
N-MeAsp: N-Methylaspartic acid
1-Nal: 3-(1'-Naphthyl)alanine
2-Nal: 3-(2'-Naphthyl)alanine
Nia: 2-Amino-3-cyanopropanoic acid (cyanoalanine)
N-MeLeu: N-Methylleucine
N-MeTrp: N(α)-Methyltryptophan
Orn: Ornithine
Orn(CHO): N⁵-Formyl-L-ornithine
Orn(COPh): N(δ)-Benzoylornithine
Orn(COCH₂Ph): N(δ)-Phenylacetylornitine
Orn(COCH₂CH₂Ph): N(δ)-(3-Phenylpropionyl)ornithine
Orn(COCH₂-Ind): N(δ)-({Indole-3-yl}acetyl)ornithine
Phe(4F): 4-Fluorophenylalanine
Phg: Phenylglycine
Pip: Pipecolic acid (piperidine-2-carboxylic acid)
Pgl: Phenylglycine
Pgy: 2-Aminopentanoic acid (propylglycine)

Pha: 2-Amino-6-(1-pyrrole)hexanoic acid
Pyr: 2-Amino-3-(3-pyridyl)propanoic acid (3-pyridylalanine)
(p-F)Phe: p-Fluorophenylalanine
Pya(2): 2-Pyridylalanine
Pya(3): 3-Pyridylalanine
Sar: Sarcosine (N-methylglycine)
Ser(Bzl): O-Benzylserine
(m-F)Tyr: m-Fluorotyrosine
Trp(Me): $N^{in}$-Metyltryptophan
Trp(CH$_2$OH): $N^{in}$-Hydroxymethyltryptophan
Trp(CHO): $N^{in}$-Formyltryptophan
Trp(For): $N^{in}$-Formyltryptophan
mTrp: 5-Methyltryptophan
Trp(Ac): $N^{in}$-Acethyltryptophan
(I)Tyr: 3-Iodotyrosine
Tyr(Et): O-Ethyltyrosine
Tyr(OEt): O-Ethyltyrosine
Tyr(Ot-Bu): O-t-Butyltyrosine
Tyr(OMe): O-Methyltyrosine
Thg(2): 2-(2-Thienyl)glycine
Thg(3): 2-(3-Thienyl)glycine
Thi: 3-(2-Thienyl)alanine
tLeu: t-Leucine
Thr(Bzl): O-Benzylthreonine
Tpr: Thioproline
Tic: Tetrahydroisoquinoline-2-carboxylic acid
Tic: 1,2,3,4-Tetrahydro-3-isoquinolinecarboxylic acid
Tza: L-3-(2-Thiazole)alanine
Tza: 2-Amino-3-(4-thiazolyl)-propanoic acid
Tha: L-3-(2-Thienyl)alanine
Thz: L-Thiazolidine-4-carboxylic acid Substituent groups, protective groups and reagents frequently used in the present specification are indicated by the following abbreviations:

AcOEt: Ethyl acetate
Ac: Acetyl
Ada: 1-Adamantylacetic acid
Adoc: Adamantyloxycarbonyl
Bzl: Benzyl
Boc: tert-Butoxycarbonyl
BrZ: 2-Bromobenzyloxycarbonyl
2-Br-Z: O-Bromobenzyloxycarbonyl
Bom: Benzyloxycarbonyl
Boc: t-Butoxycarbonyl
2-Cl-Z: O-Chlorobenzyloxycarbonyl
ClZ: 2-Chlorobenzyloxycarbonyl
CH$_3$CN: Acetonitrile
DMAP: 4-Dimethylaminopyridine
DMF: N,N-Dimethylformamide
DCC: N,N'-Dicyclohexylcarbodiimide
DCU: N,N'-Dicyclohexylurea
DCM: Dichloromethane
DIEA: N,N-Diisopropylethylamine
DCHA: N,N'-Dicyclohexylamine
Dba: 10,11-Dihydro-5H-dibenz(b,f)azepine-5-yl
DIPC: N,N'-Diisopropylcarbodiimide
DMSO: Dimethyl sulfoxide
Dnp: 2,4-Dinitrophenyl
EDCl.HCl: 1-Ethyl-3-(3-dimethylaminopropyl) carbodiimide hydrochloride
EDT: 1,2-Ethanedithiol
For: Formyl
Fmoc: 9-Fluorenylmethyloxycarbonyl
HOBt: 1-Hydroxybenzotriazole
HONB: N-Hydroxy-5-norbornene-2,3-dicarboxyimide
HOAC: Acetic acid
HCl: Hydrochloric acid
HF: Hydrogen fluoride
HOBT.H$_2$O: 1-Hydroxy-1H-benzotriazole monohydrate
HEPES: 2-[4-(2-Hydroxyethyl)-1-piperazinyl]-ethanesulfonic acid
IBCF: Isobutyl chloroformate
Ind: 1-Carboxyindane-2-yl
Iqu: 3-Carboxy-1,2,3,4-tetrahydroisoquinoline-2-yl
KOH: Potassium hydroxide
MBHA resin: p-Methylbenzhydrylamine resin
MOPS: 3-Morpholinopropanesulfonic acid
MeBzl: 4-Methylbenzyl
NO$_2$: Nitro
OPac: Phenacyl ester
OBzl: Benzyl ester
ONB: HONB ester
Pym: Pyrimidyl
Pip: Piperazyl
Pac: Phenacyl
Pfp: Pentafluorophenyl
p-TosOH: p-Toluenesulfonic acid
Pd/C: Palladium-carbon
PMSF: Phenylmethanesulfonyl fluoride
PAM resin: 4-(Oxymethyl)phenylacetamidemethyl resin
Ph: Phenyl
Tos: p-Toluenesulfonyl
TFA: Trifluoroacetic acid
TEA: Triethylamine
THF: Tetrahydrofuran
tBu: tert-Butyl
TBS: t-Butyldimethylsilyl
Tris: Tris(hydroxymethyl)aminomethane
Tos: 4-Toluenesulfonyl (tosyl)
Trt: Triphenylmethyl (trityl)
WSCD: 1-Ethyl-3-(3-dimethylaminopropyl)carbodiimide
Z: Benzyloxycarbonyl R1 to R16 represent the following groups:

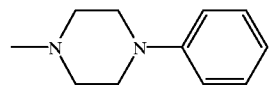

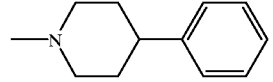

-continued

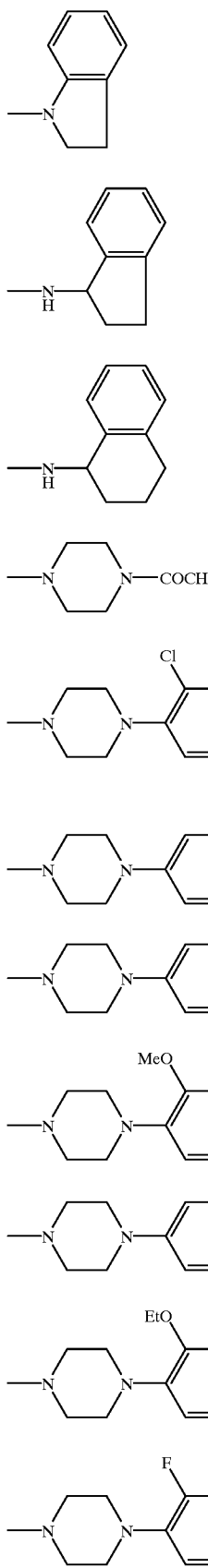

-continued

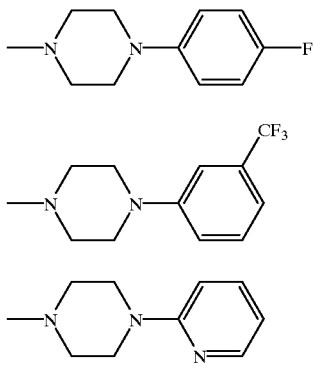

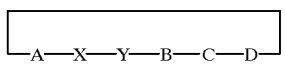

According to the present invention, there are provided (1) a prophylactic and/or therapeutic composition for the treatment of organ hypofunction, particularly hypofunction caused by surgery on or transplant of said organ, the composition comprising a pharmaceutically acceptable carrier containing an organ hypofunction treatment effective amount of a compound having antagonistic activity on an endothelin receptor;

(2) the composition described in (1), wherein the organ is a liver;

(3) the composition of (1) wherein the compound having antagonistic activity on the endothelin receptor is a cyclic peptide represented by the following formula [A] or a pharmaceutically acceptable salt thereof:

$$\boxed{\text{—A—X—Y—B—C—D—}} \qquad [A]$$

wherein X and Y each represent α-amino acid residues having D- or L-form, A represents a D-acidic-α-amino acid residue, B represents a neutral-α-amino acid residue having D- or L-form, C represents an L-α-amino acid residue and D represents a D-α-amino acid residue having an aromatic ring group;

(4) the composition of (3), wherein the cyclic peptide is
  (i) a peptide in which A is a $C_{3-5}$-D-acidic-α-amino acid residue, preferably a $C_{3-5}$-D-α-aminodicarboxylic acid residue,
  (ii) a peptide in which X is a $C_{3-11}$-L-α-amino acid residue which may be substituted, preferably a $C_{3-5}$-L-α-aminodicarboxylic acid which may be substituted by a heterocyclic group which may have a substituent group,
  (iii) a peptide in which Y is an L-acidic-α-amino acid residue, preferably a $C_{3-5}$-L-α-aminodicarboxylic acid residue,
  (iv) a peptide in which B is a $C_{2-6}$-D-neutral-α-amino acid residue which may have a heterocyclic group, preferably a $C_{2-6}$-D-α-aminomonocarboxylic acid residue which may be substituted by a sulfur-containing heterocyclic group,
  (v) a peptide in which C is an L-neutral-α-amino acid residue, preferably a $C_{5-6}$-L-α-aminomonocarboxylic acid residue, or
  (vi) a peptide in which D is a D-neutral-α-amino acid residue having an aromatic heterocyclic group, which may be acylated, preferably a D-neutral-α- amino acid residue having a nitrogen-containing aromatic heterocyclic group;
(5) the composition of (3) wherein the cyclic peptide is
Cyclo[-D-Asp-Asn(CH$_2$CH$_2$-Ind)-Asp-D-Leu-Leu-D-Trp-],
Cyclo[-D-Asp-Trp-Asp-D-Leu-Leu-D-Trp(For)-],
Cyclo[-D-Asp-Trp-Asp-D-Thg(3)-Leu-D-Trp-],
Cyclo[-D-Asp-Trp-Asp-D-γMeLeu-Leu-D-Trp-],
Cyclo[-D-Asp-Trp-Asp-D-Thg(2)-Leu-D-Trp-],
Cyclo[D-Asp-Gln(CH$_2$Ph)-Asp-D-Leu-Leu-D-Trp-],
Cyclo[-D-Asp-Asp(R1)-Asp-D-Leu-Leu-D-Trp-],
Cyclo[-D-Asp-Asp(R2)-Asp-D-Leu-Leu-D-Trp-],
Cyclo[-D-Asp-Orn(COCH$_2$Ph)-Asp-D-Leu-Leu-D-Trp-],
Cyclo[-D-Asp-Orn(COCH$_2$-Ind)-Asp-D-Leu-Leu-D-Trp-],
Cyclo[-D-Asp-Hyp(Bzl)-Asp-D-Thg(2)-Leu-D-Trp-],
Cyclo[-D-Asp-Gln(Bzl)-Asp-D-Thg(2)-Leu-D-Trp-],
Cyclo[-D-Asp-Asn(CH$_2$CH$_2$-Ind)-Asp-D-Thg(2)-Leu-D-Trp-],
Cyclo[-D-Asp-Asp(R1)-Asp-D-Thg(2)-Leu-D-Trp-],
Cyclo[-D-Asp-Asp(R7)-Asp-D-Thg(2)-Leu-D-Trp-],
Cyclo[-D-Asp-Asp(R10)-Asp-D-Thg(2)-Leu-D-Trp-],
Cyclo[-D-Asp-Asp(R12)-Asp-D-Thg(2)-Leu-D-Trp-],
Cyclo[-D-Asp-Asp(R13)-Asp-D-Thg(2)-Leu-D-Trp-],
Cyclo[-D-Cta-Asp(R1)-Asp-D-Thg(2)-Leu-D-Trp-],
Cyclo[-D-Cta-Asp(R7)-Asp-D-Thg(2)-Leu-D-Trp-],
Cyclo[-D-Cta-Asp(R10)-Asp-D-Thg(2)-Leu-D-Trp-],
Cyclo[-D-Cta-Asp(R12)-Asp-D-Thg(2)-Leu-D-Trp-],
Cyclo[-D-Cta-Asp(R13)-Asp-D-Thg(2)-Leu-D-Trp-],
Cyclo[-D-Asp-Asp(R1)-Asp-D-Cpg-Leu-D-Trp-], or
Cyclo[-D-Cta-Asp(R1)-Asp-D-Cpg-Leu-D-Trp-];
(6) the composition of (1), wherein the compound having antagonistic activity on the endothelin receptor is a peptide represented by formula [B] or a salt thereof:

[B]

$$R_1-CO-N(R_2)-CH(R_3)-CO-NH-CH(R_4)-CO-N(R_5)-CH(R_6)-(CH_2)_n-CO-NH-(CH_2)_m-CO-X$$
(L)         (D)

wherein R$_1$ represents a fat-soluble group, R$_2$ and R$_5$ each represent hydrogen atoms or lower alkyl groups, R$_3$ represents an aliphatic group which may contain an oxygen atom or a sulfur atom, R$_4$ represents a heterocyclic-lower alkyl group which may be substituted, R$_6$ represents a hydrogen atom, a lower alkyl group which may be substituted, or an aromatic ring group which may be substituted, X represents a group having an aromatic ring, n represents an integer of 0, 1 or more, and m represents an integer of 2 or more;
(7) the composition of (6), wherein the peptide or the salt thereof is hexamethylene-imino-CO-Leu-(D)Trp-(D)Ala-βAla-Tyr-(D)Phe-OH or salts thereof, hexamethyleneimino-CO-Leu-(D)Trp-(D)Ala-βAla-Tyr(I)-(D)Phe-OH or salts thereof, or hexamethyleneimino-CO-Leu-(D)Trp-(D)Ala-βAla-Try-NH-Ind-OH or salts thereof;
(8) the composition of (1), wherein the compound having antagonistic activity on the endothelin receptor is a peptide represented by formula [C] or pharmaceutically acceptable salts thereof:

[C]

M-P-Cys-Q-R-S-T-Asp-U-Glu-Cys-Val-Tyr-V-Cys-His-W-X-Y-Ile-Z-OH wherein M represents a mercaptoacyl group; P, Q, R, S, T, U, V, W, X, Y and Z each represent amino acid residues which may be any of the L-, D- and DL-forms, wherein an amino acid side chain of Y is either a substituted saturated aliphatic hydrocarbon group having 1 to 15 carbon atoms or an unsubstituted saturated aliphatic hydrocarbon group having 4 to 15 carbon atoms other than (1S)-1-methylpropyl;
(9) the composition of (8), wherein the peptide is
CysSerCysSerSerLeuMetAspLys-GluCysValTyrPheCysHisLeuThrLeuIleTrp (Abbreviation (Thr$^{18}$, Leu$^{19}$]-ET-1; SEQ ID NO:1),
CysSerCysSerSerLeuMetAspLys-GluCysValTyrPheCysHisLeuThrChaIleTrp (Abbreviation [Thr$^{18}$, Cha$^{19}$]-ET-1; SEQ ID NO:2),
CysSerCysSerSerLeuMetAspLys-GluCysValTyrPheCysHisLeuThrPheIleTrp (Abbreviation [Thr$^{18}$, Phe$^{19}$]-ET-1; SEQ ID NO:3),
CysSerCysSerSerLeuMetAspLysGluCysValTyrPheCysHisLeuThrγLeuIleTrp (Abbreviation [Thr$^{18}$, γLeu$^{19}$]-ET-1;SEQ ID NO:4),
CysSerCysSerSerLeuMetAspLys-GluCysValTyrPheCysHisLeuThrAsnIleTrp (Abbreviation [Thr$^{18}$, Asn$^{19}$]-ET-1; SEQ ID NO:5),
CysSerCysSerSerLeuMetAspLys-GluCysValTyrPheCysHisLeuSerLeuIleTrp (Abbreviation [Ser$^{18}$, Leu$^{19}$]-ET-1; SEQ ID NO:6),
CysSerCysSerSerLeuMetAspLys-GluCysValTyrPheCysHisLeuAsnLeuIleTrp (Abbreviation [Asn$^{18}$, Leu$^{19}$]-ET-1; SEQ ID NO:7),
CysSerCysSerSerLeuMetAspLys-GluCysValTyrPheCysHisLeuGlyLeuIleTrp (Abbreviation [Gly$^{18}$, Leu$^{19}$]-ET-1; SEQ ID NO:8),
CysThrCysPheThrTyrLysAspLys-GluCysValTyrTyrCysHisLeuThrLeuIleTrp (Abbreviation [Thr$^{18}$, Leu$^{19}$]-ET-3; SEQ ID NO:9),
CysSerCysSerSerLeuMetAspAla-GluCysValTyrPheCysHisLeuThrLeuIleTrp (Abbreviation [Ala$^9$Thr$^{18}$, Leu$^{19}$]-ET-1; SEQ ID NO:10),
MprSerCysSerSerLeuMetAspLysGluCysValTyrPheCysHisLeuThrLeu-IleTrp (Abbreviation [Mpr$^1$, Thr$^{18}$, Leu$^{19}$]-ET-1; SEQ ID NO:11),
CysAlaCysSerSerLeuMetAspLys-GluCysvalTyrPheCysHisLeuThrLeuIleTrp (Abbreviation [Ala$^2$, Thr$^{18}$, Leu$^{19}$]-ET-1; SEQ ID NO:12)
CysSerCysAlaSerLeuMetAspLys-GluCysValTyrPheCysHisLeuThrLeuIleTrp (Abbreviation [Ala$^4$, Thr$^{18}$, Leu$^{19}$]-ET-1; SEQ ID NO:13)
CysSerCysSerAlaLeuMetAspLys-GluCysValTyrPheCysHisLeuThrLeuIleTrp (Abbreviation [Ala$^5$, Thr$^{18}$, Leu$^{19}$]-ET-1; SEQ ID NO:14)

CysSerCysSerSerAlaMetAspLys-
GluCysValTyrPheCysHisLeuThrLeuIleTrp
(Abbreviation [Ala⁶, Thr¹⁸, Leu¹⁹]-ET-1; SEQ ID
NO:15)

CysSerCysSerSerLeuAlaAspLys-
GluCysValTyrPheCysHisLeuThrLeuIleTrp
(Abbreviation [Ala⁷, Thr¹⁸, Leu¹⁹]-ET-1; SEQ ID
NO:16)

CysSerCysSerSerLeuNleAspLys-
GluCysValTyrPheCysHisLeuThrLeuIleTrp
(Abbreviation [Nle⁷, Thr¹⁸, Leu¹⁹]-ET-1; SEQ ID
NO:17), or CysSerCysSerSerTrpLeuAspLys-
GluCysvalTyrPheCysHisLeuThrLeuIleTrp
(Abbreviation [Thr¹⁸, Leu¹⁹]-ET-2; SEQ ID NO:18);

(10) the composition of (1), wherein the compound having antagonistic activity on the endothelin receptor is a peptide represented by formula [D] or salts thereof:

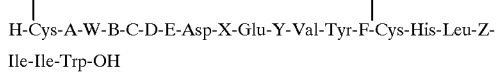

[D]

wherein A, B, C, D, E and F each represent amino acid residues which are L-form, and satisfy any one condition of (i) A=Ser, C=ser, D=Leu, E=Met and F=Phe, (ii) A=Ser, B=Ser, C=Ser, D=Trp, E=Leu and F=Phe, and (iii) A=Thr, B=Phe, C=Thr, D=Tyr, E=Lys and F=Tyr; and W, X, Y and Z each represent amino acid residues which may be any of the L-, D- and DL-forms, and at least one of W and Y is an amino acid residue other than an L-alanine residue or other than an L-cysteine residue, or X is an amino acid residue other than an L-lysine residue, or Z is an amino acid residue other than an L-aspartic acid residue;

(11) the composition of (1), wherein the compound having antagonistic activity on the endothelin receptor is a cyclic pentapeptide represented by formula [E] or pharmaceutically acceptable salts thereof:

[E]

wherein $X^n$ represents an amino acid residue (wherein n represents an integer of 1 to 5); $X^1$ represents D-Phe, D-Tyr, D-Tha, D-Tza, D-Nal, D-Bta, D-Trp, D-Trp(O), D-Trp(CHO) or D-Trp[(CH₂)ₘCOR¹] (wherein m represents an integer of 0 to 6, and $R^1$ represents a hydroxyl group, a $C_{1-6}$ alkoxyl group, an amino group or a $C_{1-6}$ monoalkylamino group); $X^2$ represents D-Asp, D-Glu or D-Cys(O₃H); $X^3$ represents Pro, Hys, Pip, Thz, β-Ala, Gly, Ala, α-Aba, Aib, Val, Nva, Leu, Ile, alle, Nle, Met, Met(O), Met(O₂), Phe, Tza, Tha, Tyr, Trp, His, Arg, Lys, Lys(CHO), Orn, Orn(CHO), Asn, Gln, Asp, Glu, Cys(O₃H), Cys, Ser or Thr, and a hydrogen atom on an α-amino group may be substituted by a $C_{1-6}$ alkyl or $C_{3-7}$ cycloalkyl group which may have a group selected from the group consisting of a imidazolyl group, a carboxyl group and a hydroxyl group; $X^4$ represents D-Ala, D-Thr, D-αAba, D-Val, D-Nva, D-Leu, D-Ile, D-alle, D-Nle, D-tertLeu, D-Cpg, D-Chg, D-Cpg, D-Pen, Aib, Ac3c, Ac4c, Ac5c, Ac6c, Ac7c (Aib to Ac7c may be any of the L-, D- and DL-forms), D-Phg, D-Thg, D-Fug, D-Tzg or D-Itg, and a hydrogen atom on an α-amino group may be substituted by a $C_{1-3}$ alkyl group; and $X^5$ represents Pro, Pip, Thz, His, Ala, αAba, Val, Nva, Leu, Ile, alle, Nle, Met, C₃al, C4al, C5al or C6al, and a hydrogen atom on an α-amino group may be substituted by a $C_{1-6}$ alkyl group;

(12) the composition of (11), wherein the peptide or the salt thereof is
Cyclo(-D-Asp-Pro-D-Val-Leu-D-Trp-),
Cyclo(-D-Cys(O₃H)-Pro-D-Val-Leu-D-Trp-),
Cyclo(-D-Asp-Pro-D-Thg(2)-Leu-D-Trp-), or
Cyclo(-D-Asp-Pro-D-Cpg-Leu-D-Trp-);

(13) the composition of (1), wherein the compound having antagonistic activity on the endothelin receptor is a peptide represented by formula [F] or salts thereof:

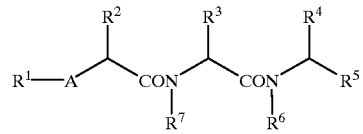

[F]

wherein $R^1$ represents a hydrogen atom or an acyl group; $R^2$ represents a lower alkyl group, an ar(lower) alkyl group which may be substituted, a cyclo(lower) alkyl(lower)alkyl group or a heterocyclic (lower) alkyl group which may be substituted; $R^3$ represents a heterocyclic (lower) alkyl group or an ar(lower)alkyl group which may be substituted; $R^4$ represents a hydrogen atom or a lower alkyl group which may be substituted; $R^5$ represents a carboxyl group, a protected carboxyl group, a carboxyl(lower)alkyl group or a protected carboxyl(lower)alkyl group; $R^6$ represents a hydrogen atom or a lower alkyl group which may be substituted; $R^7$ represents a hydrogen atom or a lower alkyl group; and A represents —O—, —NH—, a lower alkylamino group or a lower alkylene group; with the proviso that the peptide of formula [F] has an absolute configuration represented by the following partial formulae:

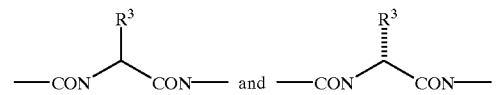

when $R^2$ is an (S)-isobutyl group, $R^3$ is an N-(dichlorobenzyloxycarbonyl)indole-3-ylmethylene group, $R^4$ is a methyl group, $R^5$ is a methoxycarbonyl group, $R^6$ is a hydrogen atom, $R^7$ is a hydrogen atom, and A is —NH—;

(14) the composition of (1), wherein the compound having antagonistic activity on the endothelin receptor is a compound represented by formula [G] or salts thereof:

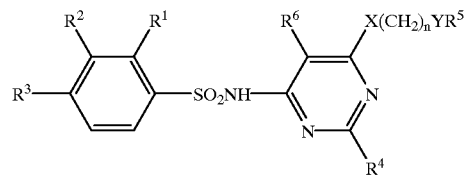

[G]

wherein $R^1$ represents a lower alkyl group, a lower alkoxyl group, a lower alkylthio group, a halogen atom or a trifluoromethyl group; R² represents a halogen atom, a lower alkoxyl group, a hydroxy-lower alkoxyl group or a trifluoromethyl group; R³ represents a hydroxyl group, a halogen atom, an alkylthio group, a cycloalkyl group, a hydroxy-lower alkyl group, a hydroxy-lower alkoxyl group, a hydroxyimino-lower alkyl group, a lower alkenyl group, an oxy-lower alkyl group, a trifluoromethyl group, a trifluoromethoxyl group, a lower alkoxyl group, a lower alkoxy-lower alkoxyl group or an aryl-lower alkoxyl group, and R² and R³ may form butadienyl; R⁴ represents a lower alkyl group, an aryl group or heterocyclic aryl group; R⁵ represents a lower alkanoyl group, a benzoyl group, a heterocyclic carbonyl group or a tetrahydropyran-2-yl group; R⁶ represents

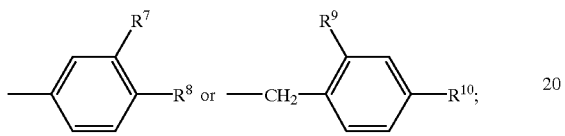

R⁷ represents a lower alkoxyl group or a nitro group; R⁸ represents a halogen atom, a lower alkyl group, a lower alkoxyl group, a lower alkylthio group, a nitro group, a hydroxyl group, an amino group or a trifluoromethyl group, and R⁷ and R⁸ may form butadienyl; R⁹ represents a halogen atom, a lower alkyl group, a lower alkoxyl group, a lower alkylthio group or a trifluoromethyl group; R¹⁰ represents a halogen atom, a lower alkyl group, a lower alkoxyl group or a lower alkylthio group; X and Y each represent O, S or NH; and n represents 2, 3 or 4;

(15) the composition of (1), wherein the compound having antagonistic activity on the endothelin receptor is a tritylpen derivative represented by formula [H]:

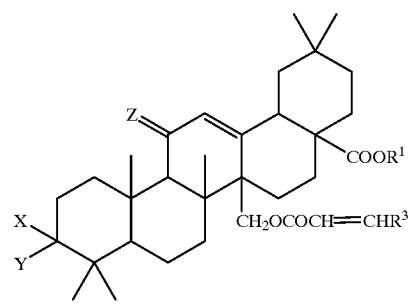

wherein R¹ represents a hydrogen atom or a metabolic ester residue; R³ represents an aryl group which may be substituted or an aromatic heterocycle which may be substituted; one of X and Y is hydroxyl and the other is hydrogen, or both X and Y are combined to form oxo; and Z represents an oxygen atom or two hydrogen atoms;

(16) the composition of (1), wherein the compound having antagonistic activity on the endothelin receptor is a Endothelin derivative represented by formula [I]:

[I]

Cys-Val-Xaa1-Phe-Cys-His-Leu-Xaa2-Ile-Ile-Xaa3 wherein Xaa1 represents Tyr, Phe or Ala; Xaa2 represents Asp or Gly; and Xaa3 represents Trp or Phe;

(17) the composition of (1), wherein the compound having antagonistic activity on the endothelin receptor is a peptide represented by formula [J]:

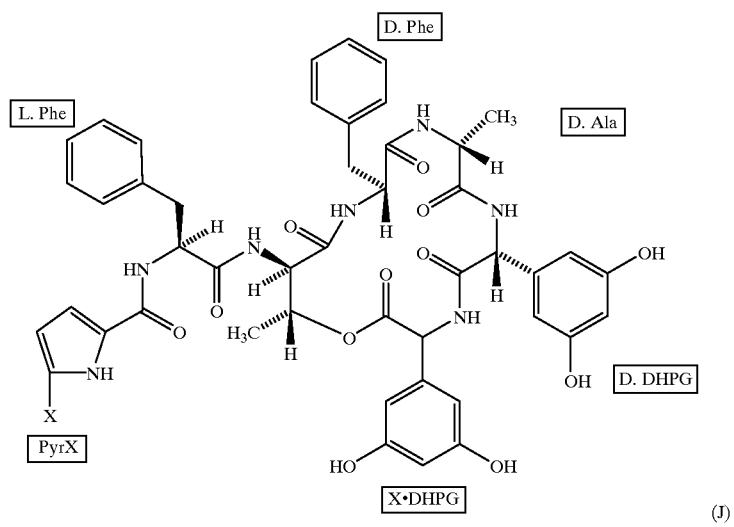

|  | PyrX | X. DHPG |
|---|---|---|
| Component I | X = H | D. DHPG |
| Component II | X = Cl | L. DHPG |
| Component III | X = Cl | D. DHPG |

(J)

(18) the composition of (1), wherein the compound having antagonistic activity on the endothelin receptor is a compound represented by formula [K]:

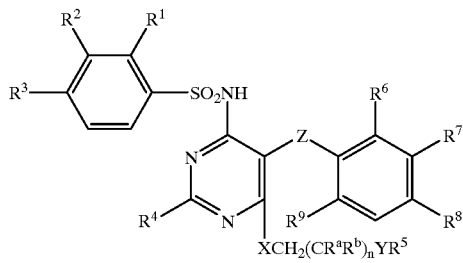

wherein $R^1$ represents a hydrogen atom, a lower alkyl group, a lower alkoxyl group, a lower alkylthio group, a halogen atom or a trifluoromethyl group; $R^2$ represents a hydrogen atom, a halogen atom, a lower alkoxyl group, a trifluoromethyl group or —$OCH_2COOR^a$; $R^3$ represents a hydrogen atom, a halogen atom, a lower alkyl group, a lower alkylthio group, a trifluoromethyl group, a cycloalkyl group or a lower alkoxyl group, and $R^2$ and $R^3$ may form butadienyl, methylenedioxy, ethylenedioxy or isopropylidene; $R^4$ represents a hydrogen atom, a lower alkyl group, a cycloalkyl group, a trifluoromethyl group, a lower alkoxyl group, a lower alkylthio group, a lower alkylthio-lower alkyl group, a hydroxy-lower alkyl group, a hydroxy-lower alkoxyl group, a lower alkoxy-lower alkyl group, hydroxy-lower alkoxy-lower alkyl group, hydroxy-lower alkoxy-lower alkoxyl group, a lower alkylslufinyl group, a lower alkylsulfonyl group, a 2-methoxy-3-hydroxypropoxyl group, a 2-hydroxy-3-phenylpropyl group, an amino-lower alkyl group, a lower alkylamino-lower alkyl group, a di-lower alkylamino-lower alkylamino group, a lower alkylamino group, a di-lower alkylamino group, an arylamino group, an aryl group, an arylthio, an aryloxy group, an aryl-lower alkyl group or a heterocycle; $R^5$ represents a hydrogen atom, a lower alkyl group, a lower alkanoyl group, a benzoyl group, a heterocyclic carbonyl group, a heterocyclic methyl group or a tetrahydropyran-2-yl group; $R^6$ to $R^9$ each represent hydrogen atoms, halogen atoms, trifluoromethyl groups, lower alkyl groups, lower alkoxyl groups, lower alkylthio groups, hydroxyl groups, hydroxymethyl groups, cyano groups, carboxyl groups, formyl groups, methylsulfinyl groups, methylsulfonyl groups, methylsulfonyloxy groups or lower alkoxycarbonyloxy groups; $R^7$ may combine with $R^6$ or $R^8$ to form butadienyl, methylenedioxy, ethylenedioxy or isopropylidenedioxy; Z represents —O—, —S—, ethylene, vinylene, —CO—, —$OCHR^{10}$— or —$SCHR^{10}$—, wherein $R^{10}$ represents a hydrogen atom or a lower alkyl group; X and Y each represent O, S or NH; $YR^5$ represents a lower alkylslufinyl group or —$OCH_2CH(OR^c)CH_2$— $OR^d$; $R^a$, $R^b$, $R^c$ and $R^d$ each represent hydrogen atoms or lower alkyl groups; $R^c$ and $R^d$ each represent methylene, ethylene or isopropylidene; and n represents 1, 2 or 3;

(19) the composition of (1), wherein the compound having antagonistic activity on the endothelin receptor is a compound represented by formula [L] or a pharmaceutically acceptable salt thereof:

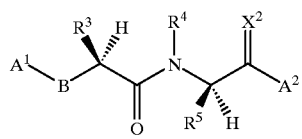

wherein $A^1$ is a group represented by formula (1), $R^{11}$—CO—, [wherein $R^{11}$ represents a lower alkyl group, a cycloalkyl group, a cycloalkyl-lower alkyl group, a group represented by $Ar^1$—$(CH_2)_p$— (wherein $Ar^1$ represents a phenyl group, a furyl group or a thienyl group, and p represents 0, 1 or 2), a 1,3-dithio-2-iridenemethyl group or 1,3-dithiol-2-iridene(lower alkoxycarbonyl)methyl group], a group represented by formula (2), $R^{12}O$—CO—, (wherein $R^{12}$ represents a lower alkyl group, a cycloalkyl group, a cycloalkyl-lower alkyl group or a phenyl group), a group represented by formula (3), $R^{13}R^{14}N$—C(=$X^1$)— [wherein $X^1$ represents an oxygen atom or a sulfur atom; $R^{13}$ represents a lower alkoxycarbonyl group, a cycloalkyl group, a lower alkynyl group, a 1-adamantyl group, a pyrrolidino group, a piperidino group, a perhydroazepine-1-yl group, a perhydroazocine-1-yl group, a perhydroazonine-1-yl, a group represented by $Ar^2$—$(CH_2)_q$— [wherein $Ar^2$ represents a phenyl group (a hydrogen atom or each of two hydrogen atoms on the benzene ring may be substituted by a halogen atom, a lower alkyl group or a lower alkoxyl group), a furyl group or thienyl group, and q represents 0, 1 or 2]; $R^{14}$ represents a hydrogen atom, a hydroxyl group, a cycloalkyl group or a group represented by $Ar^3$—$(CH_2)_r$— (wherein $Ar^3$ represents a phenyl group, a furyl group or thienyl group, and r represents 1 or 2), $R^{13}$ and $R^{14}$ may form a 5- to 9-membered nitrogen-containing saturated heterocycle having 4 to 8 carbon atoms together with the adjacent nitrogen atom, one methylene group not adjacent to a nitrogen atom in a methylene group forming the heterocycle may be substituted by an oxy group, a thio group or —$NR^{15}$— (wherein $R^{15}$ represents a lower alkyl group), 1 to 4 hydrogen atoms on a carbon atom or carbon atoms of the heterocycle may each be substituted by hydroxyl groups or lower alkyl groups which may be substituted by hydroxyl groups, two adjacent carbon atoms of the heterocycle may form a double bond or a benzo condensed ring, and $R^{13}$ and $R^{14}$ may form a group represented by formula (LII) together with B:

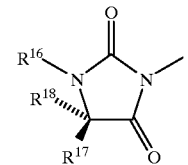

wherein $R^{16}$ represents a hydrogen atom, a lower alkyl group or a cycloalkyl group, and $R^{17}$ and $R^{18}$ each represents hydrogen atoms or lower alkyl groups, independently;

B represents an oxygen atom or a group represented by —$NR^2$— (wherein $R^2$ represents a hydrogen atom or a methyl group), and forms the group represented by the above-mentioned formula (LII) together with $A^1$;

R³ represents a lower alkyl group having 3 to 5 carbon atoms;

R⁴ represents a hydrogen atom or a methyl group;

R⁵ represents (1) a 3-indolylmethyl group, (2) a (2,3-dihydro-2-oxo-3-indolyl)methyl group, (3) a 3-indolylmethyl group in which the indole ring is substituted at the 1-position by a group represented by $R^{51}$-CO—(CH$_2$)$_s$— (wherein $R^{51}$ represents a hydrogen atom, a lower alkyl group, a hydroxyl group, a lower alkoxyl group, a benzyloxy group, an amino group or a mono-lower alkylamino group, s represents an integer of 0 to 6, and when s is 0, $R^{51}$ represents a group other than a hydroxyl group) or a group represented by $(R^{52}O)_2P(=O)$—(CH$_2$)$_t$— (wherein $R^{52}$ represents a hydrogen atom, a lower alkyl group or a benzyl group, and t represents an integer of 0 to 6), (4) a benzyl group in which any hydrogen atom on the benzene ring may be substituted by a group represented by $R^{53}O$—CO—(CH$_2$)$_u$— (wherein $R^{53}$ represents a hydrogen atom or a lower alkyl group, and u represents an integer of 0 to 6), (5) a benzyl group in which one or two hydrogen atoms on the benzene ring are substituted by hydroxyl groups, or two hydrogen atoms on the benzene ring are substituted by a hydroxyl group and a sulfo group, (6) a 3-benzothienylmethyl group, a (1-oxo-3-benzo-thienyl)methyl group or (7) a (1,1-dioxo-3-benzothienyl)-methyl group;

X² represents an oxygen atom or a sulfur atom; and

A² represents a group selected from the group consisting of groups represented by formulae (LIII), (LIV), (LV), (LVI) (LVII) and (LVIII):

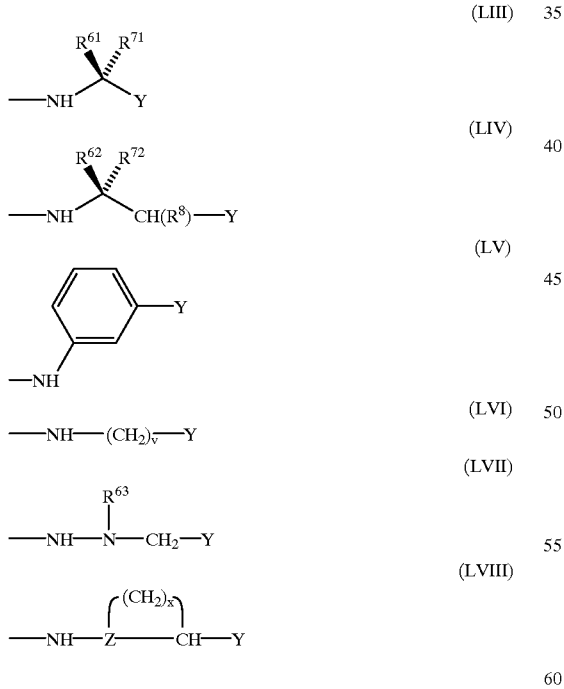

wherein Y represents a sulfo group, a group represented by —CO$_2$R$^{91}$ (wherein R$^{91}$ represents a hydrogen atom, a lower alkyl group or a benzyl group) or a group represented by —CONR$^{92}$R$^{93}$ (wherein R$^{92}$ represents a hydrogen atom, a lower alkyl group, a lower alkylsulfonyl group, a phenylsulfonyl group in which 1 to 5 arbitrary hydrogen atoms on the benzene ring may each be substituted by lower alkyl groups or halogen atoms, or a carboxymethyl group, and R$^{93}$ represents a hydrogen atom or a lower alkyl group); R$^{61}$ represents a hydrogen atom or a lower alkyl group, or represents a methylene group together with R$^{71}$; R$^{71}$ represents a hydrogen atom, a lower alkyl group which may be substituted by a hydroxyl group, a phenyl group, a thienyl group, a phenyl-lower alkyl group in which any hydrogen atom on the benzene ring may be substituted by a hydroxyl group or a benzyloxy group, a thienyl-lower alkyl group, a thiazolyl-lower alkyl group, a 4-imidazolylmethyl group, a (lower alkyl-substituted 4-imidazolyl)methylthiomethyl group, a 3-indolylmethyl group, a carbamoyl-lower alkyl group or an N-benzyloxycarbonyl-ω-amino-lower straight chain alkyl group, or represents a methylene group together with R$^{61}$, with the proviso that when R$^{61}$ is a lower alkyl group, R$^{71}$ represents a group other than a hydrogen atom; R$^{62}$ represents a hydrogen atom, a phenyl group, a benzyl group, a carboxyl group, a carbamoyl group or an N-phenylcarbamoyl group, or represents a single bond together with R$^8$; R$^{72}$ represents a hydrogen atom, a lower alkyl group, a phenyl group, a benzyl group, a 3-indolylmethyl group, a carbamoyl group or an N-phenylcarbamoyl group, with the proviso that when R$^{62}$ is a group other than a hydrogen atom, R$^{72}$ represents a hydrogen atom or a lower alkyl group; R$^8$ represents a hydrogen atom, a lower alkyl group, a lower alkoxyl group or a hydroxyl group, or represents a single bond together with R$^{62}$; V represents 3, 4 or 5; R$^{63}$ represents a hydrogen atom, a lower alkyl group, a carboxy-lower alkyl group or a group represented by Ar$^4$—(CH$_2$)$_w$— (wherein Ar$^4$ represents a phenyl group, a furyl group or a thienyl group, and w represents 1 or 2; Z represents CH or N; and X represents 1, 2 or 3;

(20) the composition of (1), wherein the compound having antagonistic activity on the endothelin receptor is a peptide represented by formula [M] or a pharmaceutically acceptable salt thereof:

AA¹-AA²-AA³-AA⁴-AA⁵-AA⁶ [M]

wherein AA¹ represents D-Dip, D-Bip, D-His, D-His (Dnp), D-2-Nal, D-1-Nal, D-Phe, D-Pgl, D-Tyr, D-Tyr (OMe), D-Tyr(OEt), D-Tyr(OtBu), D-Trp, D-Trp(For), D-Tic, D-Tza, D-Pyr, Ac-D-Dip, Ac-D-Bip, Ac-D-His, Ac-D-His(Dnp), Ac-D-2-Nal, Ac-D-1-Nal, Ac-D-Phe, Ac-D-Pgl, Ac-D-Tyr, Ac-D-Tyr(OMe), Ac-D-Tyr (OEt), Ac-D-Tyr(OtBu), Ac-D-Trp, Ac-D-Trp(For), Ac-D-Tic, Ac-D-Tza, Ac-D-Pyr, Ada-D-Dip, Ada-D-Bip, Ada-D-His, Ada-D-His(Dnp), Ada-D-2-Nal, Ada-D-1-Nal, Ada-D-Phe, Ada-D-Phe, Ada-D-Pgl, Ada-D-Tyr, Ada-D-Tyr(OMe), Ada-D-Tyr(OEt), Ada-D-Tyr (OtBu), Ada-D-Trp, Ada-D-Trp(For), Ada-D-Tic, Ada-D-Tza, Ada-D-Pyr, Adoc-D-Dip, Adoc-D-Bip, Adoc-D-His, Adoc-D-His(Dnp), Adoc-D-2-Nal, Adoc-D-1-Nal, Adoc-D-Phe, Adoc-D-Pgl, Adoc-D-Tyr, Adoc-D-Tyr(OMe), Adoc-D-Tyr(OEt), Adoc-D-Tyr(OtBu), Adoc-D-Trp, Adoc-D-Trp(For), Adoc-D-Tic, Adoc-D-Tza, Adoc-D-Pyr, Boc-D-Dip, Boc-D-Bip, Boc-D-His, Boc-D-His(Dnp), Boc-D-2-Nal, Boc-D-1-Nal, Boc-D-Phe, Boc-D-Pgl, Boc-D-Tyr, Boc-D-Tyr(OMe), Boc- D-Tyr(OEt), Boc-D-Tyr(OtBu), Boc-D-Trp, Boc-D-Trp(For), Boc-D-Tic, Boc-D-Tza, Boc-D-Pyr, Z-D-Dip, Z-D-Bip, Z-D-His, Z-D-His(Dnp), Z-D-2-Nal, Z-D-1-Nal, Z-D-Phe, Z-D-Pgl, Z-D-Tyr, Z-D-Tyr (OMe), Z-D-Tyr(OEt), Z-D-Tyr(OtBu), Z-D-Trp, Z-D-Trp(For), Z-D-Tic, Z-D-Tza, Z-D-Pyr, Fmoc-D-Dip, Fmoc-D-Bip, Fmoc-D-His, Fmoc-D-His(Dnp), Fmoc-D-2-Nal, Fmoc-D-1-Nal, Fmoc-D-Phe, Fmoc-D-Pgl, Fmoc-D-Tyr, Fmoc-D-Tyr(OMe), Fmoc-D-Tyr(OEt), Fmoc-D-Tyr(OtBu), Fmoc-D-Trp, Fmoc-D-Trp(For), Fmoc-D-Tic, Fmoc-D-Tza or Fmoc-D-Pyr;

$AA^2$ represents Ala, Alg, Arg, Asn, Asp, Dab, Glu, Gln, Gly, homoArg, homoGlu, homoLys, Ile, Leu, D-Leu, Lys, Met, Met(O), Met(O$_2$), Nva, Nle, Orn, Phe, Tyr or Val, or $AA^2$ is lacking;

$AA^3$ represents Ans, D-Ans, N-MeAns, Glu, Gln, homophe, Phe or Tyr, or $AA^3$ is lacking;

$AA^4$ represents Ala, Chx, Gly, Glu, Ile, D-Ile, Leu, Nle, Nva or Val, or $AA^4$ is lacking;

$AA^5$ represents Ala, Chx, Gly, Ile, D-Ile, Leu, Nle, Nva or Val, or $AA^5$ is lacking; and $AA^6$ represents 2-Nal, 1-Nal, Pyr, Trp, Tyr(OMe), Tyr(OEt), Tyr(OtBu), Tyr, Trp-Gly, Trp-Asp, Trp (For), Dip, Phe, Bza or

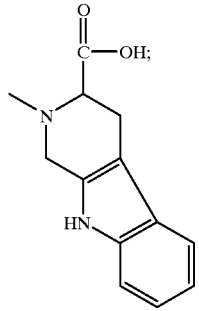

(21) the composition of (1), wherein the compound having antagonistic activity on the endothelin receptor is a compound represented by formula [N] or a pharmaceutically acceptable salt thereof:

[N]

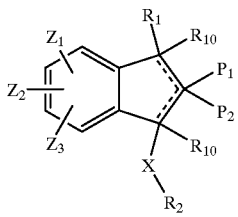

wherein:
$R_1$ is —X(CH$_2$)$_n$Ar or —X(CH$_2$)$_n$R$_8$ or (c)

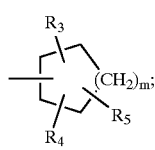

$R_2$ is hydrogen, Ar or (c);
$P_1$ is —X(CH$_2$)$_n$R$_8$;

$P_2$ is —X(CH$_2$)$_n$R$_8$, or —XR$_9$Y;

$R_3$ and $R_5$ are independently hydrogen, $R_{11}$, OH, $C_{1-8}$alkoxy, S(O)$_q$R$_{11}$, N(R$_6$)$_2$, Br, F, I, Cl, CF$_3$, NHCOR$_6$, —XR$_9$—Y or —X(CH$_2$)nR$_8$ wherein the methylene groups of —X(CH$_2$)$_n$R$_8$ may be unsubstituted or substituted by one or more —(CH$_2$)$_n$Ar groups;

$R_4$ is hydrogen, $R_{11}$, OH, $C_{1-5}$alkoxy, S(O)$_q$R$_{11}$, N(R$_6$)$_2$, —(R$_{11}$), Br, F, I, Cl or NHCOR$_6$ wherein the $C_{1-5}$alkoxy may be unsubstituted or substituted by OH, methoxy or halogen;

$R_6$ is independently hydrogen or $C_{1-4}$alkyl;

$R_7$ is independently hydrogen or $C_{1-6}$alkyl or (CH$_2$)$_n$Ar;

$R_8$ is hydrogen, $R^{11}$, COOH, PO$_3$H$_2$, P(O)(OH)R$_7$ or tetrazole;

$R_9$ is $C_{1-10}$alkyl, $C_{2-10}$alkenyl or phenyl all of which may be unsubstituted or substituted by one or more OH, N(R$_6$)$_2$, COOH, halogen or XC$_{1-5}$alkyl;

$R_{10}$ is $R_3$ or $R_4$;

$R_{11}$ is $C_{1-8}$alkyl, $C_{2-8}$alkenyl, $C_{2-8}$alkynyl all of which may be unsubstituted or substituted by one or more OH, CH$_2$OH, N(R$_6$)$_2$ or halogen;

X is (CH$_2$)$_n$, O, NR$_6$ or S(O)$_q$;

Y is CH$_3$ or —CH$_2$X(CH$_2$)$_n$Ar;

Ar is:

(a)

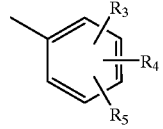

(b)

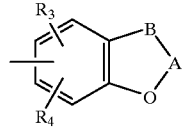

naphthyl, indolyl, pyridyl or thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is C=O, or [C(R$_6$)$_2$]$_m$;

B is —CH$_2$— or —O—;

$Z_1$ and $Z_2$ are independently hydrogen, $C_{1-8}$alkyl, $C_{2-8}$alkenyl, $C_{2-8}$alkynyl, OH, $C_{1-8}$alkoxy, S(O)$_q$ $C_{1-8}$alkyl, N(R$_6$)$_2$, Br, F, I, Cl, CF$_3$, NHCOR$_6$, —X(CH$_2$)$_n$R$_8$, phenyl, benzyl or $C_{3-6}$cycloalkyl wherein the $C_{1-8}$alkyl, $C_{2-8}$alkenyl, $C_{2-8}$alkynyl may be optionally substituted by COOH, OH, CO(CH$_2$)$_n$CH$_3$, CO(CH$_2$)$_n$CH$_2$N(R$_6$)$_2$ or halogen; or $Z_1$ and $Z_2$ together may be —O—A—O— on contiguous carbons;

$Z_3$ is $Z_1$ or XR$_9$Y;

q is zero, one or two;

n is an integer from 0 to six;

m is 1, 2 or 3;

and the dotted line indicates the optional presence of a double bond; or a pharmaceutically acceptable salt thereof; provided that $R_2$ is not hydrogen when X is S(O)$_q$;

when the optional double bond is present there is only one $R_{10}$ and there is no $P_1$;

the compound Formula I is not (1RS)-1,3-diphenylylindene-2-carboxylic acid; (cis,cis)-(1RS,3SR)-1,3-diphenylidindane-2-carboxylic acid; (1RS)-3-[3-Methyl-1-pheyl-(1H)-ind-2-en-1-yl]propionic acid; or (1RS)-2-[1,3-dipheyl-(1H)-ind-2-en-2-yl]ethanoic acid;

(22) the composition of (1), wherein the compound having antagonistic activity on the endothelin receptor is a compound represented by formula [O] or a pharmaceutically acceptable salt thereof:

$$AA^1\text{-}AA^2\text{-}A^3\text{-}AA^4\text{-}AA^5\text{-}AA^6 \qquad [O]$$

wherein $AA^1$ is

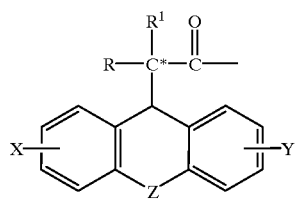

wherein R is hydrogen,
alkyl,
alkenyl,
alkynyl,
cycloalkyl,
cycloalkylalkyl,
aryl,
heteroaryl,
fluorenylmethyl,

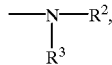

wherein $R^2$ and $R^3$ are each the same or different and each is
hydrogen,
alkyl,
alkenyl,
alkynyl,
cycloalkyl,
cycloalkylalkyl,
aryl,
arylalkyl,
heteroaryl, or
fluorenylmethyl,

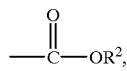

wherein $R^2$ is as defined above,
—$OR^2$, wherein $R^2$ is as defined above,

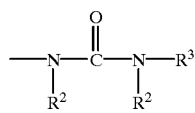

wherein $R^2$ and $R^3$ are as defined above,

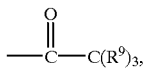

wherein $R^9$ is F, Cl, Br, or I,
—$CH_2$—$OR^2$, wherein $R^2$ is as defined above,

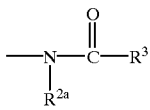

wherein $R^{2a}$ is hydrogen or alkyl and $R^3$ is defined above,

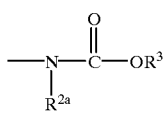

wherein $R^{2a}$ and $R^3$ are as defined above excluding $R^3$ is hydrogen, or

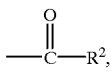

wherein $R^2$ is defined above,
$R^1$ is hydrogen or alkyl,
Z is —O—,
—$S(O)_m$—, wherein m is zero or an integer of 1 or 2,

wherein $R^2$ is as defined above,
—$(CH_2)_n$— wherein n is zero or an integer of 1, 2, 3, or 4,
—$(CH_2)_n$—CH=CH—$(CH_2)_n$— wherein n is as defined above, —CO—,

wherein $R^1$ and $R^2$ are as defined above, or

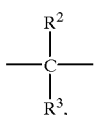

wherein $R^2$ and $R^3$ are each the same or different and each is as defined above,
X and Y are the same and each represent substituents located at the same position on the aromatic ring and each may be one, two, three, or four substituents selected from the group consisting of hydrogen,
halogen,
alkyl,
—CO$_2$R$^2$, wherein R$^2$ is as defined above,

wherein R$^2$ and R$^3$ are as defined above,

wherein R$^2$ and R$^3$ are as defined above, nitro or

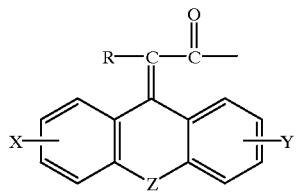

wherein R, Z, X, and Y are as defined above;
AA$^2$ is

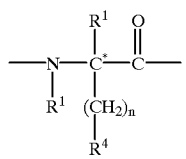

wherein R$^4$ is
hydrogen,
alkyl,
alkenyl,
alkynyl,
cycloalkyl,
aryl,
heteroaryl,

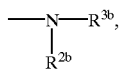

wherein R$^{2b}$ and R$^{3b}$ are each the same or different
and each is
hydrogen,
alkyl,
cycloalkyl,
aryl, or
heteroaryl,
—OR$^{2b}$, wherein R$^{2b}$ is as defined above,

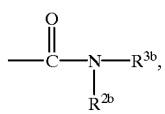

wherein R$^{2b}$ and R$^{3b}$ are each the same or different
and each is as defined above for R$^{2b}$ and R$^{3b}$,

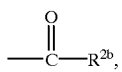

wherein R$^{2b}$ is as defined above,

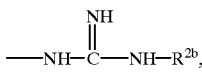

wherein R$^{2b}$ is as defined above, or

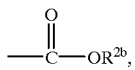

wherein R$^{2b}$ is as defined above, and R$^1$ and n are
as defined above,
AA$^2$ can be absent;
AA$^3$ is

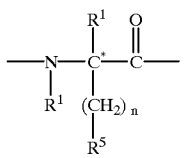

wherein R$^5$ is
hydrogen,
alkyl,
aryl,
heteroaryl,

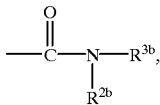

wherein R$^{2b}$ and R$^{3b}$ are each the same or different
and each is as defined above,

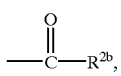

wherein R$^{2b}$ is as defined above, or

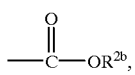

wherein R$^{2b}$ is as defined above, and R$^1$ and n are
as defined above,
AA$^3$ can be absent;
AA$^4$ and AA$^5$ are each independently absent or each is
independently

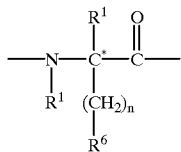

wherein R⁶ is
hydrogen,
alkyl,
alkenyl,
alkynyl,
cycloalkyl,
aryl, or
heteroaryl, and
R¹ and n are as defined above,
AA⁶ is

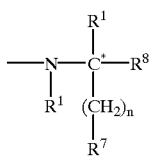

wherein R⁷ is
aryl or
heteroaryl,
R⁸ is

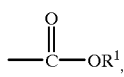

wherein R¹ is as defined above,
—OR¹, wherein R¹ is as defined above,

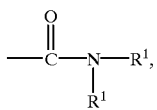

wherein R¹ is as defined above, or
—CH₂—OR¹, wherein R¹ is as defined above, and
R¹ and n are as defined above;
wherein the stereochemistry at C* in AA¹, AA², AA³, AA⁴, or AA⁵ is D, L, or DL and
wherein the stereochemistry at C* in AA⁶ is L; or a pharmaceutically acceptable salt thereof;

(23) the composition of (1), wherein the compound having antagonistic activity on the endothelin receptor is a peptide represented by formula [P] or pharmaceutically acceptable salts thereof:

X-A-Trp-B-Gly-Thr-E-G-Y (P)

wherein A represents Asn or Asp; B represents His or Lys; E represents Ala or Ser; G represents Ala or Pro; X represents X¹-Gly or

X³-Cys;

Y represents hydroxyl, lower alkoxyl, amino,

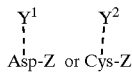
Asp-Z or Cys-Z

[wherein X¹ and X³ each represent hydrogen, benzyloxycarbonyl, t-butyloxycarbonyl, 9-fluorenylmethyloxycarbonyl, or carbonyl-substituted or unsubstituted lower alkanoyl; X² and Y² each represent hydrogen; Y¹ represents hydroxyl, lower alkoxyl or amino, or X¹ and Y¹, and X² and Y² each combine to form X¹-Y¹ and X²-Y², respectively, which represent single bonds; Z represents hydroxyl, lower alkoxyl, benzyloxy or benzhydryloxy, Gly-Z¹ (wherein Z¹ represents hydroxyl, lower alkoxyl, benzyloxy or benzhydryloxy, or forms X¹-Z¹ together with X¹, which represents a single bond), Ala-Z¹ (wherein Z¹ has the same meaning as given above), Val-Z¹ (wherein Z¹ has the same meaning as given above), Trp-Z¹ (wherein Z¹ has the same meaning as given above), Trp-Gly-Z¹ (wherein Z¹ has the same meaning as given above), Trp-Asn-Tyr-Tyr-Trp-Z¹ (wherein Z¹ has the same meaning as given above), Trp-Phe-Phe-Asn-Tyr-Tyr-7Hyt-Z¹ (wherein Z¹ has the same meaning as given above, and 7Hyt represents 7-hydroxytryptophan), Trp-Ile-Ile-Trp-Z¹ (wherein Z¹ has the same meaning as given above), Trp-Val-Tyr-Phe-W-His-Leu-Asp-Ile-Ile-Trp-Z¹ (wherein Z¹ has the same meaning as given above; and W represents Ala, Ser or Cys), Trp-W-His-Leu-Asp-Ile-Ile-Trp-Z¹ (wherein Z¹ and W have the same meanings as given above), Trp-Val-Tyr-Tyr-W-His-Leu-Asp-Ile-Ile-Trp-Z¹ (wherein Z¹ and W have the same meanings as given above), Trp-Leu-Tyr-Phe-W-His-Gln-Asp-Val-Ile-Trp-Z¹ (wherein Z¹ and W have the same meanings as given above), Trp-Val-Tyr-Phe-W-Phe-Phe-Asn-Tyr-Tyr-Trp-Z¹ (wherein Z¹ and W have the same meanings as given above), Trp-Phe-Phe-Asn-Tyr-Tyr-W-His-Leu-Asp-Ile-Ile-Trp-Z¹ (wherein Z¹ and W have the same meanings as given above), Trp-Phe-Phe-Asn-Tyr-Tyr-Asn-Ile-Ile-Trp-Z¹ (wherein Z¹ has the same meaning as given above), or J-Phe-M-Q-Tyr-R-T-Z¹ (wherein J represents Trp or a single bond; M represents Phe a single bond; Q represents Asn or a single bond; R represents Tyr or a single bond; T represents Trp, Ala, Phe, Tyr, Trp-Trp, Asn-Tyr-Tyr-Trp, Trp-Asn-Tyr-Tyr-Trp, Trp-Val-Tyr-Phe-W-His-Leu-Asp-Ile-Ile-Trp (wherein W has the same meaning as given above) or a single bond; at least two or more of J, M, Q, R and T do not concurrently form a single bond; and Z¹ has the same meaning as given above];

(24) the composition of (1) wherein the compound having antagonistic activity on the endothelin receptor is a compound represented by formula [Q] or a pharmaceutically acceptable salt thereof:

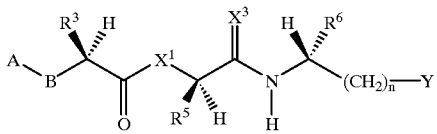

[Q]

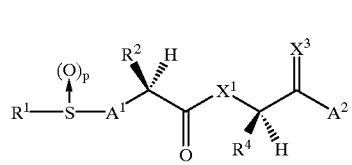

[R]

wherein A is a group of the formula $R^{11}OCO-$ (wherein $R^{11}$ is a lower alkyl group or a phenyl group), or a group of the formula $R^{12}R^{13}N-C(=O)-$ (wherein $R^{12}$ is a lower alkyl group, a cycloalkyl group, a 1-adamantyl group, a phenyl group wherein one or two optional hydrogen atoms on the benzene ring may independently be replaced by a halogen atom, a trifluoromethyl group, a nitro group, an amino group or a formylamino group, a pyridyl group, or a thienyl group, $R^{13}$ is a hydrogen atom, a lower alkyl group or a cycloalkyl group, or $R^{12}$ and $R^{13}$ form, together with the adjacent nitrogen atom, a 5- to 9-membered nitrogen-containing saturated heterocyclic ring having 4 to 8 carbon atoms, wherein among methylene groups forming the ring, one optional methylene group not adjacent to the above nitrogen atom may be replaced by a thio group, and one to four optional hydrogen atoms on the carbon atoms of the heterocyclic ring may independently be replaced by a lower alkyl group, and further two adjacent carbon atoms in the heterocyclic ring may form a benzo-fused ring); B is an oxygen atom or a group of the formula $-NR^{2}-$ (wherein $R^{2}$ is a hydrogen atom or a lower alkyl group); $R^{3}$ is a lower alkyl group, a cycloalkyl group, an anyl group, a heterocyclic group, a cycloalkyl lower alkyl group, an aryl lower alkyl group or a heterocyclic lower alkyl group; $X^{1}$ is an oxygen atom or a group of the formula $-NR^{4}-$ (wherein $R^{4}$ is a hydrogen atom or a lower alkyl group); $R^{5}$ is a 3-indolylmenthyl, 3-benzothienylmethyl, 1-naphthylmethyl or benzyl group wherein one or two optional hydrogen atoms on the ring may be replaced by a hydroxyl group, a halogen atom, a formyl group, a lower alkyl group, a lower alkoxy group, a lower alkylthio group, a lower alkylsulfinyl group, a lower alkylsulfonyl group, a lower alkoxycarbonyl group, a nitro group or a group of the formula $R^{51}-CO-X^{2}$ (wherein $R^{51}$ is a lower alkyl group, a lower alkoxy group, or an amino group which may be substituted by a lower alkyl group, and $X^{2}$ is an oxygen atom or a group of the formula $-NR^{52}-$ (wherein $R^{52}$ is a hydrogen atom or a lower alkyl group)); $X^{3}$ is an oxygen atom or a sulfur atom; $R^{6}$ is a hydrogen atom, or a lower alkyl or lower alkenyl group which may have a substituent selected from the group consisting of a hydroxyl group, a lower alkoxy group, a lower alkylthio group and a heterocyclic group; n is 0 or 1; Y is a hydroxymethyl group, a group of the formula $CO_{2}R^{71}$ (wherein $R^{71}$ is a hydrogen atom or a lower alkyl group), a group of the formula $CONHR^{72}$ (wherein $R^{72}$ is a hydrogen atom or a lower alkyl group which may have a substituent selected from the group consisting of a hydroxyl group, a carboxyl group and a sulfo group), a 1H-tetrazol-5-yl group, a sulfo group and a phosphono group; or a pharmaceutically acceptable salt thereof;

(25) the composition of (1), wherein the compound having antagonistic activity on the endothelin receptor is a compound represented by formula [R] or a pharmaceutically acceptable salt thereof:

wherein $R^{1}$ is a lower alkyl group, a cycloalkyl group, a cycloalkyl lower alkyl group, an aralkyl group, an aryl group, a 5- to 10-membered heterocyclic ring, a 5- to 10-membered heterocyclic lower alkyl group, in which on the chain and/or the ring, the lower alkyl group, the cycloalkyl group, the cycloalkyl lower alkyl group, the aralkyl group, the aryl group, the 5- to 10-membered heterocyclic ring, the 5- to 10-membered heterocyclic lower alkyl group may be each independently substituted by a lower aklyl, halogen, OH, a lower alkoxy, nitro, trifluoromethyl, cyano, formyl, a lower alkanoyl, carboxyl, a lower alkoxy carbonyl group, amino, monoloweralkylamino, diloweralkylamino, formylamino, alkanoylamino, aroylamino, carbamoyl, N-mono-loweralkylcarbamoyl or N,N-diloweralkylcarbamoyl, mercapto, loweralkylthio or loweralkanoylthio;

p is an integer of 0 to 2;

$A^{1}$ is a single bond or a divalent lower alkylene group which may be substituted with a lower alkyl;

$R^{2}$ is a lower alkyl group, a cycloalkyl group, a cycloalkyl lower alkyl group, an aralkyl group, an aryl group, a 5- to 10-membered heterocyclic ring, a 5- to 10-membered heterocyclic lower alkyl group;

$X^{1}$ is an oxygen atom or $-NR^{3}-$ wherein $R^{3}$ is hydrogen or a lower alkyl group;

$R^{4}$ is a 5- to 10-membered heterocyclic lower alkyl group which may have on the ring a lower alkyl group; $R^{41}-CO-(CH_{2})_{q}$ wherein $R^{41}$ represents hydrogen, a lower alkyl group, OH, a lower alkoxy group, aralkyloxy, amino, a monolower alkylamino group or a dilower alkylamino group; q is an integer of 0 to 6; an aryl lower aklyl group which may have on the ring nitro, $R^{42}-CO-(CH_{2})_{r}-$ wherein $R^{42}$ represents a lower alkyl group, a lower alkoxy group, amino, a mono lower alkylamino group or a dilower alkylamino group; r is an integer of 0 to 6; $R^{42}-CO-X^{2}-$ wherein $R^{42}$ has the same meaning as above, $X^{2}$ is an oxygen atom or $-NR^{43}-$ wherein $R^{43}$ is hydrogen or a lower alkyl group; or $R^{44}O-(CH_{2})_{s}-$ wherein $R^{44}$ is hydrogen or a lower alkyl group and s is an integer of 0 to 6;

$X^{3}$ represents an oxygen or sulfur atom;

$A^{2}$ represents any group selected from a group consisting of the following [RII] to [RVII]:

[RII]

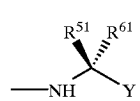

-continued

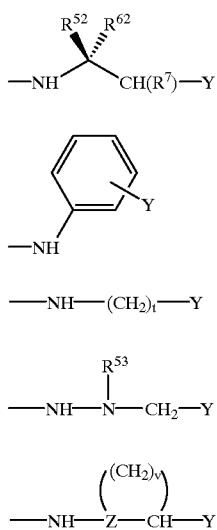

wherein Y represents a hydroxy loweralkyl group, a sulfo group, a phosphono group, —CO$_2$R$^{81}$ wherein R$^{81}$ is hydrogen or a carboxyl protective group, or —CONR$^{82}$R$^{83}$ wherein R$^{82}$ and R$^{83}$ each independently represents hydrogen, a lower alkyl group, a lower alkyl sulfonyl group, a phenyl sulfonyl group in which 1 to 5 hydrogen atoms on the benzene ring may be independently substituted by a lower alkyl group or halogen, or a carboxy lower alkyl group;

R$^{51}$ is hydrogen or a lower alkyl group, or forms a methylene group together with R$^{61}$ described below;

R$^{53}$, R$^{61}$ and R$^{62}$ each independently represents a lower alkyl group, a lower alkenyl group, an aryl group, an aryl lower alkyl group, a 5- to 10-membered heterocyclic ring, a 5- to 10-membered heterocyclic lower alkyl group; in which, on the chain and/or the ring, the lower alkyl group, the lower alkenyl group, the aryl group, the aryl lower alkyl group, the 5- to 10-membered heterocyclic ring, the 5- to 10-membered heterocyclic lower alkyl group may be each independently substituted by OH, a lower aklyl group, halogen, a lower alkoxy group, an aryloxy group, an acyloxy group, a carboxyl group, a protected carboxyl group, an amino group, a monoalkylamino group, a diloweralkylamino group, a carbamoyl group, an N-mono-loweralkylcarbamoyl group, an N,N-diloweralkylcarbamoyl group, a loweralkoxy carbonylamino group or an aryloxy carbonylamino group; further R$^{61}$ and R$^{51}$ may form together a methylene group in the proviso that R$^{61}$ is other than hydrogen when R$^{51}$ is a lower alkyl, and R$^{62}$ is hydrogen or a lower alkyl group when R$^{52}$ is other than hydrogen;

R$^{52}$ represents hydrogen, an aryl group, an aralkyl group, a carboxyl group, a carbamoyl group, an N-monoloweralkyl carbamoyl group, an N,N-diloweralkyl carbamoyl group or an N-arylcarbamoyl group; or forms a single bond with R$^{7}$;

R$^{7}$ represents hrdrogen, a lower alkyl group, a lower alkoxy group or OH, or forms a single bond with R$^{52}$;

t is an integer of 2 to 6;
Z is CH or N;
v is an integer of 1 to 3;

(26) the composition of (25), wherein the compound is represented by the formula:

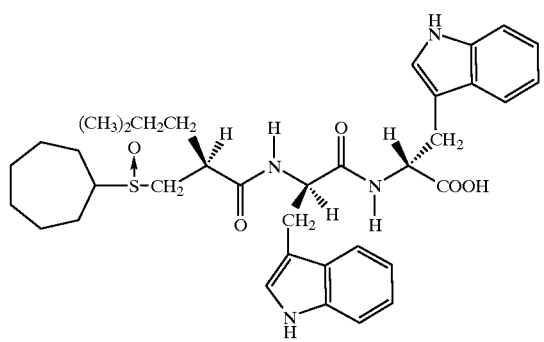

(27) the composition of (1), wherein the compound having antagonistic activity on the endothelin receptor is a cyclic pentapeptide represented by formula [S] or a pharmaceutically acceptable salt thereof:

cyclo(-Dtrp(COOCH$_3$)-Dasp-Pro-DtertLeu-γMeLeu-)   [S];

(28) the composition of (1), wherein the compound having antagonistic activity on the endothelin receptor is a compound represented by formula [T] or a pharmaceutically acceptable salt thereof:

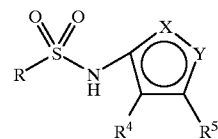

wherein one of X and Y is N and the other is O; R is naphthyl or naphthyl substituted with R$^1$, R$^2$ and R$^3$; R$^1$, R$^2$ and R$^3$ are each independently hydrogen; alkyl, alkenyl, alkynyl, alkoxy, cycloalkyl, cycloalkylalkyl, cycloalkenyl, cycloalkenylalkyl, aryl or aralkyl, any of which may be substituted with Z$^1$, Z$^2$ and Z$^3$; halo; hydroxyl; cyano; nitro; —C(O)H; —C(O)R$^6$; COOH; COOR$^6$; —SH; —S(O)nR$^6$; —S(O)$_m$—OH; —S(O)$_m$—OR$^6$; —O—S(O)$_m$—R$^6$; —O—S(O)$_m$—OH; —O—S(O)$_m$OR$^6$; —Z$^4$—NR$^7$R$^8$; or —Z$^4$—N.R$^{11}$)—Z$^5$—NR$^9$R$^{10}$;

R$^4$ and R$^5$ are each independently hydrogen; alkyl, alkenyl, alkynyl, alkoxy, cycloalkyl, cycloalkylalkyl, cycloalkenyl, cycloalkenylalkyl, aryl, or aralkyl, any of which may be substituted with Z$^1$, Z$^2$ and Z$^3$; halo; hydroxyl; cyano; nitro; —C(O)H; —C(O)R$^6$; COOH; COOR$^6$; —SH; —S(O)$_n$R$^6$; —S(O)$_m$— OH; —S(O)$_m$—OR$^6$; —O—S(O)$_m$—R$^6$; —O—S(O)$_m$OH; —O—S(O)$_m$—OR$^6$; —Z$^4$— NR$^7$R$^8$; or —Z$^4$—N.R$^{11}$)—Z$^5$—NR$^9$R$^{10}$; or R$^4$ and R$^5$ together are alkylene or alkenylene (either of which may be substituted with Z$^1$, Z$^2$ and Z$^3$), completing a 4- to 8-membered saturated, unsaturated or aromatic ring together with the carbon atoms to which they are attached;

R$^6$ is alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ or $Z^3$;

$R^7$ is as defined for $R^6$ or is H, CN, OH, COH, $COR^6$, $CO_2R^6$; or in Z is not $SO_n$, $R^7$ can be SH, $COR^6$, $SO_mOH$, $SO_mOR^6$ $OSO_mR^6$, $OSO_mOH$ or $OSO_mOR^6$;

$R^8$ is as defined for $R^6$ or H or if $Z^4$ is not CO and $R^7$ is not COH, $COR^6$ or $CO_2R^6$, $R^8$ can be COH or $COR^6$; or $NR^7R^8$ is alkylene or alkenylene (each opt. substituted with $Z^1$, $Z^2$ or $Z^3$) completing a 3–8 membered optionally saturated, unsaturated, or aromatic ring;

$R^9$ is as defined for $R^6$ or H, OH, COH or $COR^6$, $CO_2R^6$, SH, $SO_nR^6$, $SO_mOH$, $SO_mOR^6$, $OSO_mR^6$, $OSO_mOH$ or $OSO_mOR^6$;

$R^{10}$ is as defined for $R^6$ or H or if $Z^5$ is not CO and $R^9$ is not COH, $COR^6$ or $CO_2R^6$, $R^{10}$ can be COH or $COR^6$;

$R^{11}$ is as defined for $R^6$ or H, OH, COH, $COR^6$ or $CO_2R^6$; or any 2 of $R^9$, $R^{10}$ and $R^{11}$ together form alkylene or alkenylene (each opt. substituted with $Z^1$, $Z^2$ or $Z^3$) completing a 3–8 membered optionally saturated, unsaturated, or aromatic ring, with the atoms to which they are attached;

$Z^1$, $Z^2$ and $Z^3$ are H, halogen, OH, alkyl, alkenyl, aralkyl, alkoxy, aryloxy, aralkyloxy, SH, $SO_nZ^6$, $SO_mOH$, $SO_mOZ^6$, $OSO_mOH$, $OSO_mOZ^6$, oxo, $NO_2$, CN, COH, $COZ^6$, $CO_2H$, $CO_2Z^6$, $Z^4NZ^7Z^8$, $Z^4NZ^{11}Z^5Z^6$, $Z^4NZ^{11}Z^5NZ^7Z^8$;

$Z^4$,$Z^5$ are a vinyl bond, $Z^9SO_nZ^{10}$, $Z^9COZ^{10}$, $Z^9CSZ^{10}$, $Z^9OZ^{10}$, $Z^9SZ^{10}$ or $Z^9OCOZ^{10}$;

$Z^6$, $Z^7$, $Z^8$ are H, alkyl, alkenyl, alkynyl, cycloalkyl, cycloalkylalkyl, cycloalkenyl, cycloalkenylalkyl, aryl, aralkyl; or $NZ^7Z^8$ is alkylene or alkenylene completing a 3–8 membered optionally saturated, unsaturated, or aromatic ring;

$Z^9$, $Z^{10}$ are a single bond, alkylene, alkenylene or alkynylene;

$Z^{11}$ is as defined for $R^6$ or H, OH, COH, $COZ^6$ or $CO_2Z^6$; or any 2 of $Z^7$, $Z^8$ and $Z^{11}$ together form alkylene or alkenylene completing a 3–8 membered optionally saturated, unsaturated, or aromatic ring, with the atoms to which they are attached;

m is 1 or 2, n is 0, 1 or 2;

(29) the composition of (28), wherein the compound is

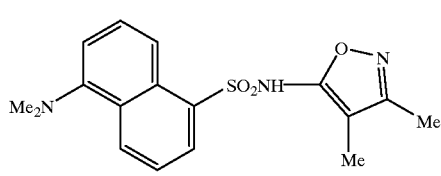

(30) the composition of (1), wherein the compound having antagonistic activity on the endothelin receptor is a compound represented by formula [U] or pharmaceutically acceptable salts thereof:

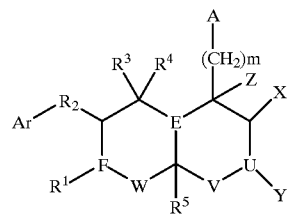

wherein Ar is a substituted or unsubstituted aromatic or heterocyclic group; R is H or a substituted or unsubstituted straight or branched chain, cyclic or mixture of straight, branched and cyclic alkyl, alkenyl, alkynyl, aryl, arylalkyl, alkoxyalkyl or alkoxycarbonyl group having from 1–20 carbon atoms; A is a functional group that bears a polar moiety, and is preferably COOH or RNH; $R_1$ is R, R—C=O, R substituted with one or more heteroatoms, a substituted or unsubstituted aryl group, or is aryl-$(CH_2)_n$; $R_2$ is $(CH_2)_n$, CHR, $C(R)_2$, COO, OCO, NHCO, CONH, SO, $SO_2$ or NR; $R_3$ and $R_4$, which are the same or different or each may be absent, and are =O, H, O-aryl, OR, O-alkyl or alkyl, aryl, SR, S-aryl, NHR, NH-aryl, NR, or are other heteroaromatic groups; $R_5$ is H, OH or R; E and F. which are the same or are different, are either N or $(CH_2)_p$; p is an integer or 0 between 0 and 5; m and n are integers or 0 between 0 and 10; T is O, S, NCOR or NR; U and V, which may be the same or different, are $(CH_2)_n$; W is CO, $(CH_2)_n$, $(CH_2)_n$—CHR or CHR—$(CH_2)_n$; X and Y, which may be the same or different, are H, alkyl or aryl or X and Y form a saturated or unsaturated homocyclic or heterocyclic ring containing 3–15 members; and Z is H, SR, NHR or $N(R)_2$;

(31) the composition of (30), wherein the compound is represented by the formula:

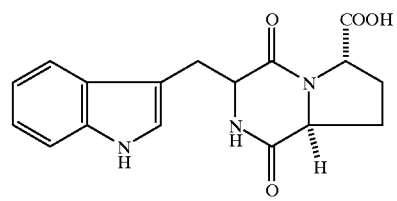

(32) the composition of (1), wherein the compound having antagonistic activity on the endothelin receptor is a compound represented by formula [V] or pharmaceutically acceptable salt thereof:

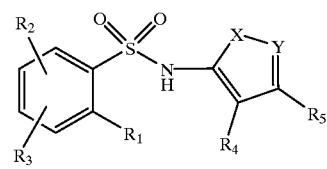

One of X, Y is N and the other is O;

$R_1$, $R_2$, $R_3$=independently H ($R_1$ is not H); alkyl, alkenyl, alkynyl, alkoxy, cycloalkyl(alkyl), cycloalkenyl(alkyl), aryl, aryloxy, aralkyl or aralkoxy; halo, hydroxyl; cyano; nitro; —C(O)H;

—C(O)R$_6$; COOH; COOR$_6$; —SH; —S(O)$_n$R$_6$; —S(O)$_m$— OH; —S(O)$_m$—OR$_6$; —O—S(O)$_m$—R$_6$; —O—S(O)$_m$—OH; —O—S(O)$_m$—OR$_6$; —Z$_4$—NR$_7$R$_8$; or —Z$_4$—N(R$^{11}$)—Z$_5$—NR$_9$R$^{10}$;

R$_4$, R$_5$=as defined for R$^1$–R$_3$ or together form a 4-8 membered saturated, unsaturated or aromatic ring;

R$_6$ is alkyl, alkenyl, alkynyl, alkoxy, cycloalkyl, cycloalkylalkyl, cycloalkenyl, cylcoalkenylalkyl, aryl or aralkyl, any of which may be substituted with Z$_1$, Z$_2$ and Z$_3$, R$_7$ is H; alkyl, alkenyl, alkynyl, alkoxy, cycloalkyl, cycloalkylalkyl, cycloalkenyl, cylcoalkenylalkyl, aryl or aralkyl, any of which may be substituted with Z$_1$, Z$_2$ and Z$_3$; cyano; hydroxyl; —C(O)H; —C(O)R$_6$; COOH; COOR$_6$; —SH; —S(O)$_n$R$_6$; —S(O)$_m$—OH; —S(O)$_m$—OR$_6$; —O—S(O)$_m$—R$_6$; —O—S(O)$_m$—OH; —O—S(O)$_m$—OR$_6$ except when Z$_4$ is —S(O)$_n$—;

R$_8$ is H; —C(O)H or —C(O)R$_6$ except when Z$_4$ is —C(O)— and R$_7$ is —C(O)H, —C(O)R$_6$, COOH or COOR$_6$; alkyl, alkenyl, alkynyl, alkoxy, cycloalkyl, cycloalkylalkyl, cycloalkenyl, cylcoalkenylalkyl, aryl or aralkyl, any of which may be substituted with Z$_1$, Z$_2$ and Z$_3$; or R$_7$ and R$_8$ together are alkylene or alkenylene (either of which may be substituted with Z$^1$, Z$_2$ and Z$_3$), completing a 3- to 8-membered saturated, unsaturated or aromatic ring together with the nitrogen atom to which they are attached;

R$_9$ is H; hydroxyl; —C(O)H or —C(O)R$_6$; COOH or COOR$_6$; —SH; —S(O)$_n$R$_6$; —S(O)$_m$—OH; —S(O)$_m$—OR$_6$; —O—S(O)$_m$—R$_6$; —O—S(O)$_m$—OH; —O—S(O)$_m$—OR$_6$; alkyl, alkenyl, alkynyl, alkoxy, cycloalkyl, cycloalkylalkyl, cycloalkenyl, cylcoalkenylalkyl, aryl or aralkyl, any of which may be substituted with Z$^1$, Z$_2$ and Z$_3$;

R$_{10}$ is H; —C(O)H or —C(O)R$_6$ except when Z$_5$ is —C(O)— and R$_9$ is —C(O)H, —C(O)R$_6$, COOH or COOR$_6$; alkyl, alkenyl, alkynyl, alkoxy, cycloalkyl, cycloalkylalkyl, cycloalkenyl, cylcoalkenylalkyl, aryl or aralkyl, any of which may be substituted with Z$^1$, Z$_2$ and Z$_3$;

R$^{11}$ is H; hydroxyl, —CO$_2$R$_6$ or COOH, except when one of R$_9$ and R$_{10}$ is hydroxyl, —CO$_2$R$_6$ or COOH; —C(O)H, —C(O)R$_6$; or alkyl, alkenyl, alkynyl, alkoxy, cycloalkyl, cycloalkylalkyl, cycloalkenyl, cylcoalkenylalkyl, aryl or aralkyl, any of which may be substituted with Z$_1$, Z$_2$ and Z$_3$;

any 2 of R$_9$, R$_{10}$ and R$_{11}$ together form alkylene or alkenylene (each opt. substituted with Z$^1$, Z$_2$ and Z$_3$) completing a 3–8 membered optionally saturated, unsaturated, or aromatic ring, with the atoms to which they are attached;

Z$_1$, Z$_2$ and Z$_3$ are each independently H; halogen; OH; alkoxy, SH, SO$_n$Z$_6$, SO$_m$OH, SO$_m$Z$_6$, OSO$_m$Z$_6$, OSO$_m$OH or OSO$_m$OZ$^6$; oxo; NO$_2$, CN, COH, COZ$_4$, CO$_2$H, CO$_2$Z$_4$, NZ$_7$Z$_8$, CONZ$_7$Z$_8$ or S(O)$_n$Z$_7$Z$_8$;

Z$_4$ and Z$_5$ are each independently a single bond; —S(O)$_n$; —C(O)—; —C(S)—; or alkyl, alkenyl, alkynyl, alkoxy, cycloalkyl, cycloalkylalkyl, cycloalkenyl, cylcoalkenylalkyl, aryl or aralkyl, any of which may be substituted with Z$_1$, Z$_2$ and Z$_3$;

Z$_6$, Z$_7$ and Z$_8$ are each independently hydrogen, alkyl, alkenyl, alkynyl, alkoxy, cycloalkyl, cycloalkylalkyl, cycloalkenyl, cylcoalkenylalkyl, aryl or aralkyl, or Z$_7$ and Z$_8$ together form alkylene or alkenylene completing a 3–8 membered saturated, unsaturated, or aromatic ring, with the nitrogen atom to which they are attached;

m is 1 or 2; and n is 0, 1, or 2.

(33) the composition of (32), wherein the compound is represented by the formula:

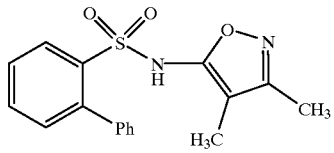

(34) the composition of (1), wherein the compound having antagonistic activity on the endothelin receptor is a cyclic pentapeptide represented by formula [W1], [W2] or [W3] or a pharmaceutically acceptable salt thereof:

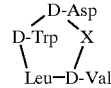

[W1]

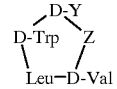

[W2]

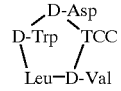

[W3]

X=an α-amino acid with a conformationally restricted 4-16C side chain.

Y=Ser, Z=an α-amino acid with a conformationally restricted side chain.

The side chain, C-amino and N-amino groups of X form 1–3 separate or fused rings with the amino groups being members of one of the rings.

TCC is 1,2,3,4-tetrahydro-2-carboline-3-caroxylic acid;

(35) the composition of (1), wherein the compound having antagonistic activity on the endothelin receptor is a compound represented by formula [X1], [X2] or [X3] or a pharmaceutically acceptable salt thereof:

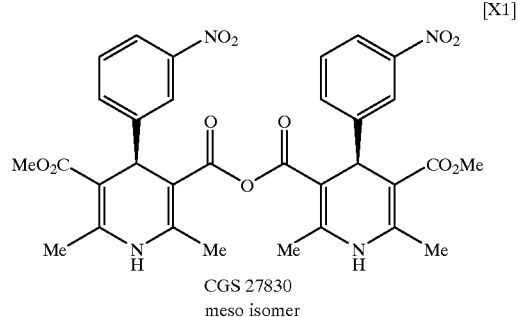

[X1]

CGS 27830
meso isomer

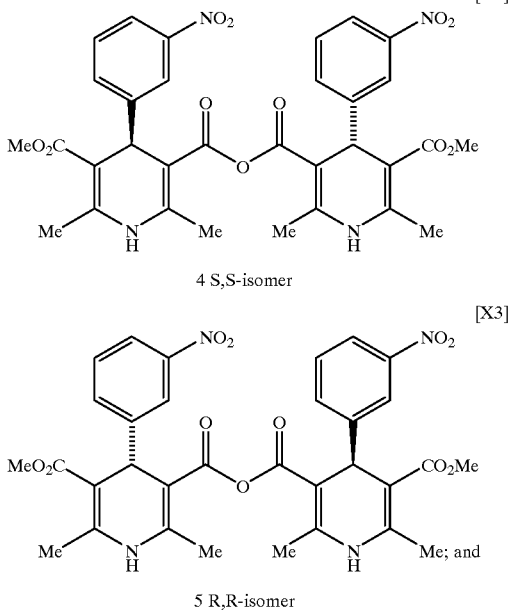

4 S,S-isomer

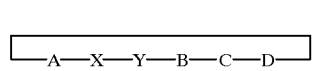

5 R,R-isomer

(36) The disodium salt of a compound cyclo(D-Asp-Asp (R1)-Asp-D-Thg(2)-Leu-D-Trp-).

This invention further provides a method for the prophylactic and/or therapeutic treatment of a mammal having organ hypofunction caused by surgery on or transplant of said organ, the method comprising a pharmaceutically acceptable carrier containing an organ hypofunction treatment effective amount of a compound of any of formula [A] to [X] which are described in the above (1) to (36) having antagonistic activity on an endothelin receptor.

The compounds having antagonistic activity on endothelin receptors used in the present invention may be any compounds having antagonistic activity on endothelin receptors, which may be known compounds or compounds having antagonistic activity on endothelin receptors which will be discovered or reported after the filing date of the invention. The compounds may be any types, peptides, proteins or chemically synthesized compounds, as long as they have antagonistic activity on endothelin receptors. Further, the compounds having antagonistic activity on endothelin receptors may be any compounds having antagonistic activity on endothelin-1 receptors, endothelin-2 receptors and endothelin-3 receptors. In particular, the compounds having antagonistic activity on endothelin-1 receptors are preferred. In the present invention, the compounds having antagonistic activity on endothelin receptors include compounds called endothelin antagonists in the field of the present invention. Furthermore, although the endothelin receptors include type A ($ET_A$ receptor) and type B ($ET_B$ receptor), the term "endothelin receptors" as used in the present invention is used to refer to either or both the types.

Examples of the compounds having antagonistic activity on endothelin receptors used in the present invention include compounds described in EP-A-528,312, EP-A-552,489, EP-A-499,266, WO91/13089, EP-A-436,189, EP-A-457,195, EP-A-510,526, WO92/12991, Japanese Patent Unexamined Publication No. 4-288099, EP-A-496,452, EP-A-526,708, EP-A-460,679 and WO92/20706, the disclosure of which are hereby incorporated by reference. Furthermore, the compounds having antagonistic activity on endothelin receptors used in the present invention include compounds described in WO93/08799, WO93/13218, WO93/21219, EP-A-555,537, Japanese Patent Unexamined Publication Nos. 5-178890 and 5-279390, EP-A-558,258, WO93/23404, EP-A-569193, WO93/17701 and Bioorganic & Medicinal Chemistry Letters, Vol.10, pp.2099–2104 (1993), the disclosure of which are hereby incorporated by reference. Among them, the compounds described in EP-A-552489, EP-A-528,312, EP-A-499,266, WO91/13089, EP-A-436, 189, EP-A-457,195, EP-A-510,526, WO92/12991, EP-A-526,708 and WO93/08799 are preferable, and the compounds described in EP-A-528,312 is most preferable.

The compounds which have antagonistic activity on endothelin receptor of the present invention include the salts of the above-described compounds. Preferable Examples of the salts include the pharmaceutically acceptable salts of the compounds having antagonistic activity on endothelin receptor.

The pharmaceutically acceptable salts of the compounds having antagonistic activity on endothelin receptors include alkali metal salts (such as sodium salts and potassium salts), alkaline earth metal salts (such as calcium salts and magnesium salts), ammonium salts, organic base salts (such as pyridine salts and triethylamine salts), inorganic acid salts (such as hydrochlorides, sulfates and nitrates) and organic acid salts (such as acetates, oxalates and p-toluenesulfonates).

The compounds and salts of the compounds which have antagonistic activity on endothelin receptor can be produced by conventional methods well known to those skilled in the art as illustrated in the cited reference.

These compounds are described below. [Japanese Patent Application No. 4-216019 (EP-A-0,528,312)]

Cyclic peptides represented by formula [A] or salts thereof:

$$\boxed{\text{—A—X—Y—B—C—D—}} \qquad [A]$$

wherein X and Y each represent α-amino acid residues, A represents a D-acidic-α-amino acid residue, B represents a neutral-α-amino acid residue, C represents an L-α-amino acid residue and D represents a D-α-amino acid residue having an aromatic ring group.

The above-mentioned compounds represented by formula [B] include (1) compounds in which A is a $C_{3-5}$-D-acidic-α-amino acid residue, preferably a $C_{3-5}$-D-α-aminodicarboxylic acid residue, (2) compounds in which X is a $C_{3-11}$-L-α-amino acid residue which may be substituted, preferably a $C_{3-5}$-L-α-aminodicarboxylic acid which may be substituted by a heterocyclic group which may have a substituent group, (3) compounds in which Y is an L-acidic-α-amino acid residue, preferably a $C_{3-5}$-L-α-aminodicarboxylic acid residue, (4) compounds in which B is a $C_{2-6}$-D-neutral-α-amino acid residue which may have a heterocyclic group, preferably a $C_{2-6}$-D-α-aminomonocarboxylic acid residue which may be substituted by a sulfur-containing heterocyclic group, (5) compounds in which C is an L-neutral-α-amino acid residue, preferably a $C_{5-6}$-L-α-aminomonocarboxylic acid residue, and (6) compounds in which D is a D-neutral-α-amino acid residue having an aromatic heterocyclic group, which may be acylated, preferably a D-neutral-α-amino acid residue having a nitrogen-containing aromatic heterocyclic group.

Preferred examples of the $C_{3-11}$-L-α-amino acids substituted in the above-mentioned $C_{3-11}$-L-α-amino acid residues which may be substituted include $C_{3-11}$-L-α-amino acids having functional groups (for example, hydroxyl, mercapto, amino, imino and carboxyl groups) substituted. The functional groups substituted include the above-mentioned hydroxyl, thiol, amino (or imino) and carboxyl groups substituted.

The above-mentioned heterocyclic groups which may have substituent groups include, for example, 5- and 6-membered ring groups each having 1 to 4 heteroatoms selected from oxygen, sulfur and nitrogen atoms in addition to carbon atoms (for example, 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isooxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, 2-, 4- or 5-pyrimidinyl, thiomorpholinyl, morpholinyl, oxoimidazinyl, dioxotriazinyl, pyrrolidinyl, piperidinyl, pyranyl, thiopyranyl, 1,4-oxazinyl, 1,4-thiazinyl, 1,3-thiazinyl, piperazinyl, triazinyl, oxotriazinyl, 3- or 4-pyridazinyl, and pyrazinyl). Examples of the substituent groups include $C_{1-4}$ alkyl groups (for example, methyl, ethyl, propyl, isopropyl, butyl, isobutyl, sec-butyl and tert-butyl), $C_{5-7}$ cycloalkenyl groups (for example, cyclopentenyl and cyclohexenyl), $C_{7-11}$ aralkyl groups (for example, benzyl, α-methylbenzyl and phenethyl), $C_{6-10}$ aryl group (for example, phenyl, naphthyl and anthracenyl), $C_{1-6}$ alkoxyl groups (for example, methoxy, ethoxy, propoxy, iso-propoxy, n-butoxy, iso-butoxy, sec-butoxy and tert-butoxy) and $C_{1-6}$ alkanoyl groups (for example, formyl, acetyl, propionyl, n-butyryl and iso-butyryl). Each of these substituent groups may have 1 to 3 substituent groups such as halogen atoms (for example, fluorine, chlorine, bromine and iodine), mono-, di- or tri-halogeno-$C_{1-4}$ alkyl groups (for example, chloromethyl, dichloromethyl, trifluoromethyl and trifluoroethyl) and $C_{1-6}$ alkoxyl groups (for example, methoxy, ethoxy, propoxy, iso-propoxy, n-butoxy, iso-butoxy, sec-butoxy and tert-butoxy).

The above-mentioned sulfur-containing heterocyclic groups include, for example, 5- and 6-membered ring groups containing 1 or 2 sulfur atoms in addition to carbon atoms (for example, 2- or 3-thienyl, thiomorpholinyl, dithianyl and thiopyranyl).

Examples of the acyl groups in the above-mentioned acylation include acyl groups derived from organic carboxylic acids. Preferred examples of the acyl groups include formyl, $C_{1-6}$ alkyl-carbonyl groups (such as acetyl, ethylcarbonyl and hexylcarbonyl), $C_{6-10}$ aryl-carbonyl groups (such as phenylcarbonyl and naphthylcarbonyl) and $C_{7-11}$ aralkyl-carbonyl groups (such as benzylcarbonyl).

The above-mentioned aromatic heterocyclic groups include, for example, 5- and 6-membered aromatic heterocyclic groups each having 1 to 4 heteroatoms selected from oxygen, sulfur and nitrogen atoms in addition to carbon atoms, which may be condensed with benzene rings, (for example, 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isooxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, 2-, 4- or 5-pyrimidinyl, 2- or 3-indolyl, 1-, 2- or 3-indolizinyl, 2- or 3-quinolyl, phthalazinyl, quinoxalinyl quinazolinyl, cinnolinyl and 2-benzimidazolyl).

The above-mentioned nitrogen-containing heterocyclic groups include, for example, 5- and 6-membered aromatic heterocyclic groups each having 1 to 3 nitrogen atoms in addition to carbon atoms, which may be condensed with benzene rings, (for example, 2- or 3-pyrrolyl, 2-, 3- or 4-pyridyl, 3-, 4- or 5-pyrazolyl, 2-, 4- or 5-imidazolyl, 1,2,3-triazolyl, 1,2,4-triazolyl, 1H- or 2H-tetrazolyl, 2-, 4- or 5-pyrimidinyl, 2- or 3-indolyl, 1-, 2- or 3-indolizinyl, 2- or 3-quinolyl, phthalazinyl, quinoxalinyl quinazolinyl, cynolinyl and 2-benzimidazolyl).

Specifically, cyclic peptides or salts thereof shown in Examples of Japanese Patent Application No. 4-216019 (EP-A-0,528,312) are used. In particular, the following compounds are preferably used:

Cyclo[-D-Asp-Asn (CH$_2$CH$_2$-Ind)-Asp-D-Leu-Leu-D-Trp-]: Example 12

Cyclo[-D-Asp-Trp-Asp-D-Leu-Leu-D-Trp(For)-]: Example 42

Cyclo[-D-Asp-Trp-Asp-D-Thg(3)-Leu-D-Trp-]: Example 49

Cyclo[-D-Asp-Trp-Asp-D-γMeLeu-Leu-D-Trp-]: Example 54

Cyclo[-D-Asp-Trp-Asp-D-Thg(2)-Leu-D-Trp-]: Example 55

Cyclo[D-Asp-Gln(CH$_2$Ph)-Asp-D-Leu-Leu-D-Trp-]: Example 62

Cyclo[-D-Asp-AspR1)-Asp-D-Leu-Leu-D-Trp-]: Example 70

Cyclo[-D-Asp-AspR2)-Asp-D-Leu-Leu-D-Trp-]: Example 71

Cyclo[-D-Asp-Orn(COCH$_2$Ph)-Asp-D-Leu-Leu-D-Trp-]: Example 80

Cyclo[-D-Asp-Orn(COCH$_2$-Ind)-Asp-D-Leu-Leu-D-Trp-]: Example 82

Cyclo[-D-Asp-Hyp(Bzl)-Asp-D-Thg(2)-Leu-D-Trp-]: Example 88

Cyclo[-D-Asp-Gln(Bzl)-Asp-D-Thg(2)-Leu-D-Trp-]: Example 89

Cyclo[-D-Asp-Asn(CH$_2$CH$_2$-Ind)-Asp-D-Thg(2)-Leu-D-Trp-]: Example 90

Cyclo[-D-Asp-AspR1)-Asp-D-Thg(2)-Leu-D-Trp-]: Example 96

Cyclo[-D-Asp-AspR7)-Asp-D-Thg(2)-Leu-D-Trp-]: Example 136

Cyclo[-D-Asp-AspR10)-Asp-D-Thg(2)-Leu-D-Trp-]: Example 139

Cyclo[-D-Asp-AspR12)-Asp-D-Thg(2)-Leu-D-Trp-]: Example 141

Cyclo[-D-Asp-AspR13)-Asp-D-Thg(2)-Leu-D-Trp-]: Example 142

Cyclo[-D-Cta-AspR1)-Asp-D-Thg(2)-Leu-D-Trp-]: Example 146

Cyclo[-D-Cta-AspR7)-Asp-D-Thg(2)-Leu-D-Trp-]: Example 147

Cyclo[-D-Cta-AspR10)-Asp-D-Thg(2)-Leu-D-Trp-]: Example 150

Cyclo[-D-Cta-AspR12)-Asp-D-Thg(2)-Leu-D-Trp-]: Example 152

Cyclo[-D-Cta-AspR13)-Asp-D-Thg(2)-Leu-D-Trp-]: Example 153

Cyclo[-D-Asp-AspR1)-Asp-D-Cpg-Leu-D-Trp-]: Example 157

Cyclo[-D-Cta-AspR1)-Asp-D-Cpg-Leu-D-Trp-]: Example 168

The cyclic peptide represented by formula [A] has 6 amide bonds including a bond between A and D, thereby showing that the molecule forms a ring as a whole. This peptide is sometimes referred to as cyclo[-A-X-Y-B-C-D-].

In formula [A], an amino acid which forms the α-amino acid residue represented by X or Y may be any amino acid as long as it is an α-amino acid. Examples thereof include alanine, arginine, asparagine, aspartic acid, cysteine, glutamine, glutamic acid, 2-aminomalonic acid, 2-aminoadipic acid, glycine, histidine, isoleucine, leucine, lysine, ornithine, 2,4-diaminobutyric acid, methionine, phenylalanine, proline, 4-hydroxyproline, thioproline, azetidine-2-carboxylic acid, pipecolic acid (piperidine-2-carboxylic acid), indoline-2-carboxylic acid, tetrahydroisoquinoline-3-carboxylic acid, serine, threonine, tryptophan, 5-methyltryptophan, tyrosine, valine, alloisoleucine, norvaline, norleucine, tertiary leucine, γ-methylleucine, phenylglycine, 2-aminobutyric acid, cysteic acid, homocysteic acid, 3-(1-naphthyl)alanine, 3-(2-naphthyl)alanine, 2-(2-thienyl)glycine, 2-(3-thienyl)glycine, 3-(3-benzothienyl)alanine, 3-(4-biphenyl)alanine, pentamethylphenylalanine, 1-aminocyclopropane-1-carboxylic acid, 1-aminocyclobutane-1-carboxylic acid, 1-aminocyclopentane-1-carboxylic acid, 1-aminocyclohexane-1-carboxylic acid and 1-aminocycloheptane-1-carboxylic acid. When these α-amino acids have functional groups such as hydroxyl, thiol, amino, imino and carboxyl, these functional groups may be substituted.

The substituted hydroxyl groups include esters such as $C_{1-6}$ fatty acid esters (for example, formates, acetates and propionates), $C_{4-9}$ alicyclic carboxylic acid esters (for example, cyclopentanecarboxylates and cyclohexanecarboxylates), $C_{7-15}$ arylcarboxylic acid esters (for example, benzoates and 4-methylbenzoates), $C_{8-16}$ aralkylcarboxylic acid esters (for example, phenylacetates, 2-phenylpropionates, 3-phenylpropionates and diphenylacetates) and aromatic heterocycle-alkylcarboxylic acid esters (for example, indole-2-ylacetates and indole-3-ylacetates); and ethers such as $C_{1-6}$ alkyl ethers (for example, methyl ethers, ethyl ethers, n-propyl ethers and tert-butyl ethers), $C_{3-8}$ cycloalkyl ethers (for example, cyclopentyl ethers and cyclohexyl ethers), $C_{6-12}$ aryl ethers (for example, phenyl ethers and 4-methylphenyl ethers) and $C_{7-15}$ aralkyl ethers (for example, benzyl ethers, phenethyl ethers and diphenylmethyl ethers). Examples of the α-amino acids whose hydroxyl groups are substituted include O-acetylserine, O-acetylthreonine, 4-acetoxyproline, O-benzoylserine, O-benzoylthreonine, 4-benzoyloxyproline, O-phenylacetylserine, O-phenylacetylthreonine, 4-phenyl-acetoxyproline, O-ethylserine, O-ethylthreonine, 4-ethoxy-proline, O-cyclohexylserine, O-cyclohexylthreonine, 4-cyclohexyloxyproline, O-phenylserine, O-phenylthreonine, 4-phenoxyproline, O-benzylserine, O-benzylthreonine, 4-benzyloxyproline, O-diphenylmethylserine, O-diphenylmethylthreonine and 4-diphenylmethoxyproline.

The substituted thiol groups include thiol esters such as $C_{1-6}$ fatty acid thiol esters (for example, formic acid thiol esters, acetic acid thiol esters and propionic acid thiol esters), $C_{4-9}$ alicyclic carboxylic acid thiol esters (for example, cyclopentanecarboxylic acid thiol esters and cyclohexanecarboxylic acid thiol esters), $C_{7-15}$ arylcarboxylic acid thiol esters (for example, benzoic acid thiol esters and 4-methylbenzoic acid thiol esters) and $C_{8-16}$ aralkylcarboxylic acid thiol esters (for example, phenylacetic acid thiol ester, 2-phenylpropionic acid thiol esters, 3-phenylpropionic acid thiol esters and diphenylacetic acid thiol esters); and thioether forms such as $C_{1-6}$ alkyl thioethers (for example, methyl thioethers, ethyl thioethers, n-propyl thioethers and tert-butyl thioethers), $C_{3-8}$ cycloalkyl thioethers (for example, cyclopentyl thioethers and cyclohexyl thioethers), $C_{6-12}$ aryl thioethers (for example, phenyl thioethers and 4-methylphenyl thioethers) and $C_{7-15}$ aralkyl thioethers (for example, benzyl thioethers, phenethyl thioethers and diphenylmethyl thioethers). Examples of the α-amino acids whose thiol groups are substituted include S-acetylcysteine, S-benzoylcysteine, S-phenylacetylcysteine, S-ethylcysteine, S-cyclohexylcysteine, S-phenylcysteine and S-benzylcysteine.

The substituted amino groups (or imino groups) include substituted amino or imino groups such as $C_{1-6}$ alkylamino (or imino) [for example, N-methylamino (or imino), N-ethylamino (or imino) and N-t-butylamino (or imino)], $C_{3-8}$ cycloalkylamino (or imino) [for example, N-cyclopentylamino (or imino) and N-cyclohexylamino (or imino)], $C_{6-12}$ arylamino (or imino) [for example, N-phenylamino (or imino) and N-{4-methylphenyl}amino (or imino)], $C_{7-15}$ aralkylamino (or imino) [for example, N-benzylamino (or imino), N-phenethylamino (or imino), N-{2-chlorobenzyl}amino (or imino), N-{3-chlorobenzyl}amino (or imino), N-{4-chlorobenzyl}amino (or imino), N-{2-methylbenzyl}amino (or imino), N-{3-methylbenzyl}amino (or imino), N-{4-methylbenzyl}amino (or imino), N-{2-methoxybenzyl}amino (or imino), N-{3-methoxybenzyl}amino (or imino) and N-{4-methoxybenzyl}amino (or imino)] and aromatic heterocycle-$C_{1-6}$ alkylamino (or imino) [for example, 2-furylmethylamino (or imino), 3-furylmethylamino (or imino), 2-thienylmethylamino (or imino), 3-thienylmethylamino (or imino), indole-2-ylmethylamino (or imino) and indole-3-ylmethylamino (or imino)]; and substituted amido (or imido) groups such as $C_{1-6}$ aliphatic acylamido (or imido) [for example, formamido (or imido), acetamido (or imido) and propionamido (or imido)], $C_{4-9}$ alicyclic acylamido (or imido) [for example, cyclopentanecarbonylamido (or imido) and cyclohexanecarbonylamido (or imido)], $C_{7-15}$ arylacylamido (or imido) [for example, benzamido (or imido) and 4-methylbenzamido (or imido)], $C_{8-16}$ aralkylacylamido (or imido) [for example, phenylacetamido (or imido), 2-phenylpropionamido (or imido), 3-phenylpropionamido (or imido), diphenylacetamido (or imido), 1-naphthylacetamido (or imido) and 2-naphthylacetamido (or imido)], aromatic heterocyclecarbonylamido (or imido) [for example, indole-2-ylcarbonylamido (or imido) and indole-3-ylcarbonylamido (or imido)], aromatic heterocycle-alkylcarbonylamido (or imido) (for example, indole-2-ylacetamido (or imido) and indole-3-ylacetamido (or imido)], and sulfonylamido (or imido) [for example, benzenesulfonylamido (or imido), p-toluenesulfonylamido (or imido) and 4-methoxy-2,3,6-trimethylbenzenesulfonylamido (or imido)]. Examples of the α-amino acids whose amino (or imino) groups are substituted include N-methylglycine (sarcosine), N-ethylglycine, N-methylleucine, N-ethylleucine, N-methylphenylalanine, N-ethylphenylalanine, N(α)- methyltryptophan, N(α)-ethyltryptophan, N-cyclopentylglycine, N-cyclohexylglycine, N-phenylglycine, N-phenylleucine, N-benzylglycine, N-benzylleucine, N(π)-benzylhistidine, N(τ)-benzylhistidine, N(π)-phenacylhistidine, N(π)-benzyloxymethylhistidine, $N^g$-benzenesulfonylarginine, $N^g$-p-toluenesulfonylarginine, $N^g$-(4-methoxy-2,3,6-trimethylbenzenesulfonyl)arginine, N(ε)-benzenesulfonyllysine, N(ε)-p-toluenesulfonyllysine, N(ε)-(4-methoxy-2,3,6-trimethylbenzenesulfonyl)lysine, $N^{in}$-methyltryptophan, $N^{in}$-ethyltryptophan, $N^{in}$-formyltryptophan, $N^{in}$-acetyltryptophan, N(ε)-benzyllysine, N(ε)-(2-furylmethyl)lysine, N(ε)-(2-thienylmethyl)lysine, N(ε)-(indole-3-ylmethyl)lysine, N(ε)-phenylacetyllysine, N(ε)-({2-furyl}acetyl)lysine, N(ε)-({2-thienyl}acetyl)lysine, N(ε)-({indole-3-yl}acetyl)lysine, N(ε)-benzoyllysine, N(ε)-(3-phenylpropionyl)lysine, N(δ)-benzylornithine, N(δ)-(2-furylmethyl)ornithine, N(δ)-(2-thienylmethyl)ornithine, N(δ)-(indole-3-ylmethyl)ornithine, N(δ)-benzoylornithine, N(δ)-phenylacetylornithine, N(δ)-(3-phenylpropionyl)ornithine, N(δ)-({2-methylphenyl}acetyl)ornithine, N(δ)-({3-methylphenyl}acetyl)ornithine, N(δ)-({4-methylphenyl}acetyl)ornithine, N(δ)-({2-chlorophenyl}acetyl)ornithine, N(δ)-({3-chlorophenyl}acetyl)ornithine, N(δ)-({4-chlorophenyl}acetyl)ornithine, N(δ)-({2-methoxyphenyl}acetyl)ornithine, N(δ)-({3-methoxyphenyl}acetyl)ornithine, N(δ)-({4-methoxyphenyl}acetyl)ornithine, N(δ)-(4-biphenylacetyl)ornithine, N(γ)-benzyl-2,4-diaminobutyric acid, N(γ)-(2-furylmethyl)-2,4-diaminobutyric acid, N(γ)-(2-thienylmethyl)-2,4-diaminobutyric acid, N(γ)-(indole-3-ylmethyl)-2,4-diaminobutyric acid, N(γ)-benzoyl-2,4-diaminobutyric acid, N(γ)-phenylacetyl-2,4-diaminobutyric acid, N(γ)-(3-phenylpropionyl)-2,4-diaminobutyric acid, N(γ)-(2-furylacetyl)-2,4-diaminobutyric acid, N(γ)-(2-thienylacetyl)-2,4-diaminobutyric acid and N(γ)-({indole-3-yl}acetyl)-2,4-diaminobutyric acid.

The substituted carboxyl groups include amido groups such as carboxylic acid amido (—$CONH_2$), N-$C_{1-6}$ alkylamido (for example, N-methylamido, N-ethylamido, N-{n-propyl}-amido and N-t-butylamido), N-$C_{3-8}$ cycloalkylamido (for example, N-cyclopentylamido and N-cyclohexylamido), N-$C_{6-12}$ arylamido (for example, N-phenylamido and N-{4-methylphenyl}amido), N-$C_{7-15}$ aralkylamido (for example, N-benzylamido, N-phenethylamido, N-{1,2-diphenylethyl}amido), N-{aromatic heterocycle-$C_{1-6}$ alkyl}amido (for example, N-[2-{indole-2-yl}ethyl]amido and N-[2-{indole-3-yl}ethyl]amido), piperidineamido, piperazineamido, $N^4$-$C_{1-6}$ alkylpiperazineamido (for example, $N^4$-methylpiperazineamido and $N^4$-ethylpiperazineamido), $N^4$-$C_{3-8}$ cycloalkylpiperazineamido (for example, $N^4$-cyclopentylpiperazineamido and $N^4$-cyclohexylpiperazineamido), $N^4$-$C_{6-12}$ arylpiperazineamido (for example, $N^4$-phenylpiperazineamido and $N^4$-{4-methylphenyl}piperazineamido), $N^4$-$C_{7-15}$ aralkylpiperazineamido (for example, $N^4$-benzylpiperazineamido, $N^4$-phenetylpiperazineamido, $N^4$-{1,2-diphenylethyl}piperazineamido), $N^4$-{aromatic heterocycle-$C_{1-6}$ alkyl}piperazineamido (for example, $N^4$-[2-{indole-2-yl}ethyl]piperazineamido and $N^4$-[2-{indole-3-yl}ethyl]piperazineamido), $N^4$-$C_{1-6}$ aliphatic acylpiperazineamido (for example, $N^4$-acetylpiperazineamido and $N^4$-propionylpiperazineamido), $N^4$-$C_{4-9}$ alicyclic acylpiperazineamido (for example, $N^4$-cyclopentanecarbonylpiperazineamido and $N^4$-cyclohexanecarbonylpiperazineamido), $N^4$-$C_{7-15}$ arylacylpiperazineamido (for example, $N^4$-benzoylpiperazineamido and $N^4$-{4-methylbenzoyl}piperazineamido), $N^4$-$C_{8-16}$ aralkylacylpiperazineamido (for example, $N^4$-phenylacetylpiperazineamido $N^4$-{2-phenylpropion}piperazineamido, $N^4$-{3-phenylpropionyl}piperazineamido, $N^4$-diphenylacetylpiperazineamido), $N^4$-{1-naphthylacetyl}piperazineamido and $N^4$-{2-naphthylacetyl}piperazineamido), $N^4$-{aromatic heterocycle-carbonyl}piperazineamido (for example, $N^4$-{indole-2-ylcarbonyl}piperazineamido and $N^4$-{indole-3-ylcarbonyl}piperazineamido), and $N^4$-{aromatic heterocyclicalkylcarbonyl}piperazineamido (for example, $N^4$-{indole-2-ylacetyl}piperazineamido and $N^4$-{indole-3-ylacetyl}piperazineamido); and esters such as $C_{1-6}$ alkyl esters (for example, methyl esters, ethyl esters and n-propyl esters), $C_{3-8}$ cycloalkyl esters (for example, cyclopentyl esters and cyclohexyl esters) and $C_{7-15}$ aralkyl esters (for example, benzyl esters, phenetyl esters, 1-phenylethyl esters and diphenylmethyl esters). The above-mentioned amido forms also include amido groups with α-amino acids and amido groups with oligopeptides (for example, dipeptides, tripeptides and tetrapeptides). The α-amino acids whose carboxyl groups are substituted include, for example, $N^4$-methylasparagine, $N^4$-phenylasparagine, $N^4$-benzylasparagine, $N^4$-phenethylasparagine, $N^4$-(2-{indole-3-yl}ethyl)asparagine, $N^5$-methylglutamine, $N^5$-phenylglutamine, $N^5$-benzylglutamine, $N^5$-phenethylglutamine, $N^5$-(2-{indole-3-yl}ethyl) glutamine, aspartic acid β-methyl ester, aspartic acid β-cyclopropyl ester, aspartic acid β-benzyl ester, aspartic acid β-phenethyl ester, aspartic acid β-$N^4$-phenylpiperazineamide, aspartic acid β-$N^4$-(2-methylphenyl)piperazineamide, aspartic acid β-$N^4$-(3-methylphenyl)piperazineamide, aspartic acid β-$N^4$-(4-methylphenyl)piperazineamide, aspartic acid β-$N^4$-(2-methoxyphenyl)piperazineamide, aspartic acid β-$N^4$-(3-methoxyphenyl)piperazineamide, aspartic acid β-$N^4$-(4-methoxyphenyl)piperazineamide, aspartic acid β-$N^4$-(2-chlorophenyl)piperazineamide, aspartic acid β-$N^4$-(3-chlorophenyl)piperazineamide, aspartic acid β-$N^4$-(4-chlorophenyl)piperazineamide, aspartic acid β-$N^4$-(4-nitrophenyl)piperazineamide, aspartic acid β-$N^4$-(4-fluorophenyl)piperazineamide, aspartic acid β-$N^4$-(3-trifluoromethylphenyl)piperazineamide, aspartic acid β-$N^4$-(2,3-dimethylphenyl)piperazineamide, aspartic acid β-$N^4$-(2-pyridyl)piperazineamide, aspartic acid β-$N^4$-(2-pyrimidyl)piperazineamide, glutamic acid γ-methyl ester, glutamic acid γ-cyclopropyl ester, glutamic acid γ-benzyl ester and glutamic acid γ-phenethyl ester.

The α-amino acid which forms the amino acid residue represented by X or Y in formula [A] may be any of the L-, D- and DL-forms. The L-form is, however, more preferred in each case.

An amino acid which forms the D-acidic-α-amino acid residue represented by A in formula [A] is, for example, an amino acid with an acidic group such as carboxyl, sulfonyl or tetrazolyl as a side chain. Examples of such amino acids include D-glutamic acid, D-aspartic acid, D-cysteic acid, D-homocysteic acid, D-β-(5-tetrazolyl)alanine and D-2-amino-4-(5-tetrazolyl)butyric acid. In particular, D-glutamic acid, D-aspartic acid and D-cysteic acid are preferred.

An amino acid which forms the neutral-α-amino acid residue represented by B in formula [A] is an α-amino acid.

Examples of such α-amino acids include alanine, valine, norvaline, leucine, isoleucine, alloisoleucine, norleucine, tertiary leucine, γ-methylleucine, phenylglycine, phenylalanine, 3-(1-naphthyl)alanine, 3-(2-naphthyl)alanine, proline, 4-hydroxyproline, azetidine-2-carboxylic acid, pipecolic acid (piperidine-2-carboxylic acid), 3-(2-thienyl)alanine, 2-(2-thienyl)glycine, 2-(3-thienyl)glycine, 1-aminocyclopropane-1-carboxylic acid, 1-aminocyclobutane-1-carboxylic acid, 1-aminocyclopentane-1-carboxylic acid, 1-aminocyclohexane-1-carboxylic acid, 1-aminocycloheptane-1-carboxylic acid, 2-cyclopentylglycine and 2-cyclohexylglycine. When the above-mentioned neutral-α-amino acid exists in the L- and D-forms, the D-form is preferred. D-Leucine, D-alloisoleucine, D-tertiary leucine, D-γ-methylleucine, D-phenylglycine, D-3-(2-thienyl)alanine, D-2-(2-thienyl) glycine, D-2-(3-thienyl)glycine and D-2-(2-cyclopentyl) glycine are preferred among others. α-Imino groups of these neutral-α-amino acids may be substituted by $C_{1-6}$ alkyl groups (for example, methyl, ethyl, n-propyl and tert-butyl). Examples of such α-amino acids include N-methylleucine, N-methylalloisoleucine, N-methyl tertiary leucine, N-methyl γ-methylleucine and N-methylphenylglycine. Also for these α-amino acids, the D-form is preferred.

As an amino acid which forms the L-α-amino acid residue represented by C in formula [A], used is an L-α-amino acid usually known in the art. Examples of such L-α-amino acids include glycine, L-alanine, L-valine, L-norvaline, L-leucine, L-isoleucine, L-tertiary leucine, L-norleucine, L-methionine, L-2-aminobutyric acid, L-serine, L-threonine, L-phenylalanine, L-aspartic acid, L-glutamic acid, L-asparagine, L-glutamine, L-lysine, L-tryptophan, L-arginine, L-tyrosine and L-proline. In particular, L-leucine, L-norleucine and L-tryptophan are preferred. α-Imino groups of these L-α-amino acids may be substituted by $C_{1-6}$ alkyl groups (for example, methyl, ethyl, n-propyl and tert-butyl). Examples of such L-α-amino acids include L-N-methylleucine, L-N-methylnorleucine and L-N(α)-methyltryptophan.

As an amino acid which forms the D-α-amino acid residue with the aromatic ring group represented by D in formula [A], used is a D-α-amino acid having an aromatic ring group as a side chain. Examples thereof include D-tryptophan, D-5-methyltryptophan, D-phenylalanine, D-tyrosine, D-3-(1-naphthyl)alanine, D-3-(2-naphthyl) alanine, D-3-(3-benzothienyl)alanine, D-3-(4-biphenyl) alanine and D-pentamethylphenylalanine. D-Tryptophan and D-5-methyltryptophan are preferred, and particularly, D-tryptophan is more preferred. α-Imino groups of the D-α-amino acids having aromatic rings may be substituted by $C_{1-6}$ alkyl groups (for example, methyl, ethyl, n-propyl and tert-butyl). Further, the imino group of the indole ring of D-tryptophan may be substituted by a hydrocarbon group such as a $C_{1-6}$ alkyl group (for example, methyl, ethyl, n-propyl or tert-butyl), a $C_{3-8}$ cycloalkyl group (for example, cyclopentyl or cyclohexyl), a $C_{6-12}$ aryl group (for example, phenyl, or 4-methylphenyl) or $C_{7-15}$ aralkyl (for example, benzyl or phenethyl), or an acyl group such as a $C_{1-6}$ aliphatic acyl group (for example, formyl, acetyl or propionyl), a $C_{4-9}$ alicyclic acyl group (for example, cyclopentanecarbonyl or cyclohexanecarbonyl), a $C_{7-15}$ arylacyl group (for example, benzoyl or 4-methylbenzoyl), a $C_{8-16}$ aralkylacyl group (for example, phenylacetyl, 2-phenylpropionyl, 3-phenylpropionyl or diphenylacetyl) or a $C_{1-6}$ alkoxycarbonyl group (for example, methoxycarbonyl or ethoxycarbonyl). Examples of such α-amino acids include D-N(α)-methyltryptophan, D-N-methylphenylalanine, D-N-methyltyrosine, D-$N^{in}$-methyltryptophan, D-$N^{in}$-ethyltryptophan, D-$N^{in}$-formyltryptophan and D-$N^{in}$-acetyltryptophan. D-$N^{in}$-methyltryptophan, D-$N^{in}$-formyltryptophan and D-$N^{in}$-acetyltryptophan are preferred among others.

The salts of the cyclic peptides represented by formula [A] include metal salts (for example, sodium salts, potassium salts, calcium salts and magnesium salts), salts of bases or basic compounds (for example, ammonium salts and arginine salts), addition salts of inorganic acids (for example, hydrochlorides, sulfates and phosphates), and salts of organic acids (for example, acetates, propionates, citrates, tartarates, malates and oxalates).

[EP-A-552,489]

Peptides represented by formula [B] or salts thereof:

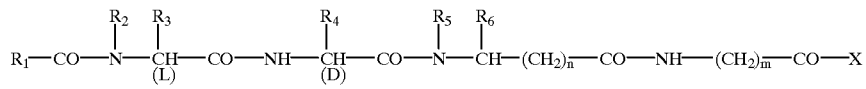

[B]

wherein $R_1$ represents a fat-soluble group, $R_2$ and $R_5$ each represent hydrogen atoms or lower alkyl groups, $R_3$ represents an aliphatic group which may contain an oxygen atom or a sulfur atom, $R_4$ represents a heterocyclic-lower alkyl group which may be substituted, $R_6$ represents a hydrogen atom, a lower alkyl group which may be substituted, or an aromatic ring group which may be substituted, X represents a group having an aromatic ring, n represents an integer of 0, 1 or more, and m represents an integer of 2 or more.

Specifically, the peptides or the salts thereof described in Examples of EP-A-552,489 are used. In particular, hexamethylene-imino-CO-Leu-(D)Trp-(D)Ala-βAla-Tyr-(D)Phe-OH or salts thereof, hexamethyleneimino-CO-Leu-(D)Trp-(D)Ala-βAla-Tyr(I)-(D)Phe-OH or salts thereof, hexamethyleneimino-CO-Leu-(D)Trp-(D)Ala-βAla-Try-NH-Ind-OH or salts thereof and the like are preferred.

In the above-mentioned formula [B], $R_1$ represents a fat-soluble group. The fat-soluble group may be any, as long as it is a group enhancing fat solubility of a compound by attaching it to the compound. Examples of the fat-soluble groups include alkyl, cycloalkyl, alkoxyl, aromatic and substituted amino groups. These groups may be further substituted.

The alkyl group represented by $R_1$ is preferably a straight chain or branched chain alkyl group having 1 to 10 carbon atoms. Examples thereof include methyl, ethyl, n-propyl, isopropyl, n-butyl, isobutyl, sec-butyl, tert-butyl, n-pentyl, isoamyl, tert-amyl, neopentyl, n-hexyl, n-heptyl, n-octyl, n-nonyl and n-decyl. Lower alkyl groups each having 1 to 6 carbon atoms (for example, methyl, ethyl, n-propyl, isopropyl, n-butyl, isobutyl, sec-butyl, tert-butyl, n-pentyl, isoamyl, tert-amyl, neopentyl and n-hexyl) are preferred among others. These alkyl groups may be substituted. Examples of the substituent groups which are used herein include $C_{3-8}$ cycloalkyl groups (such as cyclopentyl and cyclohexyl), halogen atoms (such as fluorine, chlorine, bromine and iodine), $C_{1-6}$ alkoxyl groups (such as methoxy, ethoxy, n-propoxy, isopropoxy, n-butoxy and tert-butoxy), $C_{1-6}$ alkylthio groups (such as methylthio, ethylthio, n-propylthio, isopropylthio, n-butylthio and tert-butylthio), $C_{1-6}$ alkoxy-carbonyl groups (such as methoxycarbonyl, ethoxycarbonyl, isopropoxycarbonyl and tert-butoxycarbonyl), and aromatic ring groups [such as $C_{6-12}$ aromatic hydrocarbon groups which may be substituted by halogen atoms, hydroxyl groups, $C_{1-3}$ alkoxyl groups or $C_{1-3}$ alkyl groups (for example, phenyl, fluorophenyl, chlorophenyl, bromophenyl, hydroxyphenyl, methoxyphenyl, methylphenyl, 1-naphthyl and 2-naphthyl); and 5- to 10-membered aromatic heterocyclic groups each having 1 to 4 heteroatoms such as O, S and N (for example, furyl, thienyl, thiazolyl, indolyl, pyridyl, pyranyl, imidazolyl, pyrimidyl and quinolyl)]. The number of the substituent groups for these alkyl group is preferably 1 to 3.

The cycloalkyl group represented by $R_1$ is preferably a cycloalkyl group having 3 to 10 carbon atoms. Examples thereof include cyclopropyl, cyclobutyl, cyclopentyl, cyclohexyl, cycloheptyl, cyclooctyl, adamantyl, bornyl and norbornyl). These cycloalkyl groups may be substituted, and the substituent groups include $C_{1-6}$ alkyl groups (such as methyl, ethyl, n-propyl and n-butyl), halogen atoms (such as fluorine, chlorine, bromine and iodine), $C_{1-6}$ alkoxyl groups (such as methoxy, ethoxy, n-propoxy, iso-propoxy, n-butoxy and tert-butoxy), $C_{1-6}$ alkylthio groups (such as methylthio, ethylthio, n-propylthio, isopropylthio, n-butylthio and tert-butylthio), and $C_{1-6}$ alkoxycarbonyl groups (such as methoxycarbonyl, ethoxycarbonyl, isopropoxycarbonyl and tert-butoxycarbonyl). The number of the substituent groups for these cycloalkyl groups is preferably 1 to 3. Condensed groups of the above-mentioned cycloalkyl groups with other rings (for example, benzene rings) are also included. Examples of such groups include indane-1-yl, indane-2-yl, 1,2,3,4-tetrahydronaphthalene-1-yl and 1,2,3,4-tetrahydronaphthalene-2-yl.

The alkoxyl group represented by $R_1$ is preferably a straight chain or branched chain alkoxyl group having 1 to 8 carbon atoms. Examples thereof include methoxy, ethoxy, n-propoxy, isopropoxy, n-butoxy, isobutoxy, sec-butoxy, tert-butoxy, n-pentyloxy, isoamyloxy, tert-amyloxy, neopentyloxy, n-hexyloxy, n-heptyloxy and n-octyloxy. These alkoxyl groups may be substituted, and the substituent groups include $C_{3-8}$ cycloalkyl groups (such as cyclopentyl and cyclohexyl), $C_{1-6}$ alkoxyl groups (such as methoxy, ethoxy, n-propoxy, iso-propoxy, n-butoxy and tert-butoxy), and $C_{1-6}$ alkoxycarbonyl groups (such as methoxycarbonyl, ethoxycarbonyl, isopropoxycarbonyl and tert-butoxycarbonyl). The number of the substituent groups for these alkoxyl groups is preferably 1 to 3. The above-mentioned alkyl and alkoxyl groups represented by $R_1$ are preferably branched.

The aromatic ring group represented by $R_1$ may be either an aromatic hydrocarbon group or an aromatic heterocyclic group is usable. As the aromatic hydrocarbon groups, those each having 6 to 15 carbon atoms (for example, phenyl and α-naphthyl) are employed. Each of these aromatic hydrocarbon groups may further contain 1 to 3 substituent groups selected from halogen atoms (for example, fluorine, chlorine and bromine), hydroxyl, $C_{1-6}$ alkyl groups (for example, methyl and ethyl), $C_{1-6}$ alkoxyl groups (for example, methoxy and ethoxy), carboxyl, $C_{1-6}$ alkylcarbonyl groups (for example, formyl and acetyl), $C_{1-6}$ alkoxycarbonyl groups (for example, acetoxy) and the like. As the aromatic hydrocarbon groups which may be substituted, for example, phenyl, 4-fluorophenyl, 4-chlorophenyl, 4-bromophenyl, 4-hydroxyphenyl, 4-methoxyphenyl, 4-methylphenyl, 1-naphthyl and 2-naphthyl are frequently used. Examples of the aromatic heterocyclic groups include 5- and 6-membered heterocyclic groups each having 1 to 4 heteroatoms such as O, S and N (for example, 2-furyl, 3-furyl, 2-thienyl, 3-thienyl, thiazole-4-yl, 2-pyridyl, 3-pyridyl, 4-pyridyl and 2-pyranyl), and condensed groups of these heterocyclic groups with other aromatic rings such as benzene rings (for example, indole-3-yl, N-methylindole-3-yl, 2-quinolyl and quinoxaline-2-yl). These aromatic heterocyclic groups may each have 1 to 3 substituent groups similar to those which the above-mentioned aromatic hydrocarbon groups may contain.

The substituted amino group represented by $R_1$ is preferably a monosubstituted amino group ($R_7NH—$) or a disubstituted amino group ($R_8R_9N—$), wherein $R_7$, $R_8$, and $R_9$ are groups capable of imparting fat solubility to the substituted amino group. As such $R_7$, $R_8$ and $R_9$, alkyl groups each having 4 or more carbon atoms, cycloalkyl groups each having 5 or more carbon atoms and aromatic groups are used. The alkyl groups each having 4 or more carbon atoms are more preferably alkyl groups each having 4 to 10 carbon atoms, which include, for example, n-butyl, isobutyl, sec-butyl, tert-butyl, n-pentyl, isoamyl, tert-amyl, neopentyl, n-hexyl, n-heptyl, n-octyl, n-nonyl and n-decyl. The cycloalkyl groups each having 5 or more carbon atoms are more preferably cycloalkyl groups each having 5 to 10 carbon atoms, which include, for example, cyclopentyl, cyclohexyl, cycloheptyl, cyclooctyl, adamantyl, bornyl and norbornyl. The aromatic ring groups represented by $R_7$, $R_8$ and $R_9$ include, for example, $C_{6-12}$ aromatic hydrocarbon groups such as phenyl, 1-naphthyl and 2-naphthyl; 5- to 10-membered aromatic heterocyclic groups each having 1 to 4 heteroatoms such as O, S and N, (for example, furyl, thienyl, thiazolyl, pyridyl and pyranyl); and condensed groups products of these groups with other aromatic rings (for example, benzene rings) such as indolyl, quinolyl and quinoxalyl. Each of these alkyl, cycloalkyl and aromatic ring groups may further contain 1 to 3 substituent groups. The substituent groups for the alkyl groups include, for example, $C_{3-8}$ cycloalkyl groups (such as cyclopentyl and cyclohexyl), $C_{1-6}$ alkoxyl groups (such as methoxy, ethoxy, n-propoxy, isopropoxy, n-butoxy and tert-butoxy), $C_{1-6}$ alkylthio groups (such as methylthio, ethylthio, n-propylthio, iso-propylthio, n-butylthio and tert-butylthio), hydroxyl, carboxyl, and $C_{1-6}$ alkylcarbonyl groups (such as formyl and acetyl). The substituent groups on the carbon atoms of the aromatic ring groups include $C_{1-6}$ alkyl groups (such as methyl, ethyl, n-propyl and n-butyl), $C_{1-6}$ alkoxyl groups (such as methoxy, ethoxy, n-propoxy and n-butoxy), hydroxyl, carboxyl, and $C_{1-6}$ alkylcarbonyl groups (such as formyl and acetyl). The disubstituted amino group ($R_8R_9N—$) includes a group in which $R_8$ and $R_9$ form a ring together with the adjacent nitrogen atom.

As the ring formed by both $R_8$ and $R_9$, a 5- to 13-membered nitrogen-containing heterocycle which may contain 1 or 2 heteroatoms such as oxygen and sulfur atoms besides the nitrogen atom is employed. Examples of the nitrogen-containing heterocyclic groups include pyrrolinidino, piperidinino, hexamethyleneimino, heptamethyleneimino, oxazolidino, morpholino, thiazolidino, thiomorpholino, imidazolidino, piperazino, pyrrolino, 1,2-dihydropyridino, 1,4-dihydropyridino, 1,2,3, 6-tetrahydropyridino, 2-oxazolidonino, 2-thiazolidonino, imidazolino, pyrazolino, 1,4,5,6-tetrahydropyrimidino, 2,3- dihydro-1H-indolino, 1,2,3,4-tetrahydroquinolino, 2,3,4,5-tetrahydro-1H-1-benzazepinino, 2,3-dihydro-1H-isoindolino, 1,2,3,4-tetrahydroisoquinolino, 2,3,4,5-tetrahydro-1H-2-benzazepinino, 2,3,4,5-tetrahydro-1H-3-benzazepinino, 1,2,3,4,5,6-hexahydro-1-benzazocino, 1,2,3,4,5,6-hexahydro-2-benzazocino, 1,2,3,4,5,6-hexahydro-3-benzazocino, 2,3,4,5,6,7-hexahydro-1H-1-benzazonino, 2,3,4,5,6,7-hexahydro-1H-2-benzazonino, 2,3,4,5,6,7-hexahydro-1H-3-benzazonino, 2,3,4,5,6,7-hexahydro-1H-4-benzazonino, β-carbolino, phenoxazino, phenothienyl, 3H-3-benzazepino, 3,4-dihydroquinolino, benzimidano, 1,4-benzodiazepino and 10,11-dihydro-5H-dibenz(b,f)azepine-5-yl.

These heterocycles may further contain 1 to 3 substituent groups, which include, for example, $C_{1-6}$ alkyl groups (for example, methyl, ethyl, n-propyl and isopropyl), phenyl, halogen atoms (for example, fluorine, chlorine and iodine), nitro, cyano, hydroxyl, $C_{1-4}$ alkoxyl groups (for example, methoxy, ethoxy, n-propoxy, n-butoxy and isopropoxy), $C_{1-4}$ alkylthio groups (for example, methylthio, ethylthio, propylthio and isopropylthio), amino, mono- or di-$C_{1-4}$ alkylamino groups (for example, methylamino, ethylamino, propylamino, dimethylamino and diethylamino), $C_{1-4}$ alkylcarbonylamino groups (for example, formylamino, acetylamino, propionylamino and butyrylamino), $C_{1-4}$ alkylsulfonylamino groups (for example, methylsulfonylamino and ethylsulfonylamino), $C_{1-4}$ alkoxycarbonyl groups (for example, methoxycarbonyl, ethoxycarbonyl and propoxycarbonyl), carboxyl, $C_{1-6}$ alkylcarbonyl groups (for example, formyl, methylcarbonyl, ethylcarbonyl and propylcarbonyl), $C_{1-4}$ alkylcarbonyloxy groups (for example, acetyl and ethylcarbonyloxy), and 5- and 6-membered heterocyclic groups each having 1 to 4 heteroatoms such as O, S and N (for example, pyridinyl, furyl and thiophenyl). The monosubstituted amino groups ($R_7NH$—) are more preferably cyclohexylamino, phenylamino (anilino) and benzylamino. The disubstituted amino groups ($R_8R_9N$—) are more preferably dicyclohexylamino, diphenylamino, hexamethyleneimino (homopiperidinyl), 10,11-dihydro-5H-dibenz(b,f)azepin-5-yl (Dba), morpholino, piperidino, methylpiperazino and 1-(2-pyrimidyl)piperazino.

In formula [B], $R_2$ and $R_5$ each represent hydrogen atoms or lower alkyl groups. The lower alkyl groups are preferably straight chain or branched chain alkyl groups each having 1 to 6 carbon atoms, which include, for example, methyl, ethyl, n-propyl, isopropyl, n-butyl, isobutyl, sec-butyl, tert-butyl, n-pentyl, isoamyl, tert-amyl, neopentyl and n-hexyl. As $R_2$ and $R_5$, hydrogen atoms and $C_{1-3}$ alkyl groups such as methyl are preferred among others.

In formula [B], $R_3$ represents an aliphatic group which may contain an oxygen atom or a sulfur atom. The aliphatic groups are preferably alkyl groups, cycloalkyl groups and cycloalkylalkyl groups, and methylene groups ($CH_2$) at any positions other than the α-positions of these aliphatic groups may be replaced by oxygen or sulfur atoms. The alkyl groups are preferably straight chain or branched chain alkyl groups each having 1 to 8 carbon atoms, which include, for example, methyl, ethyl, n-propyl, isopropyl, n-butyl, isobutyl, sec-butyl, tert-butyl, n-pentyl, isoamyl, tert-amyl, neopentyl, n-hexyl, n-heptyl, n-octyl, methoxymethyl, ethoxymethyl, 2-methoxyethyl, 2-ethoxyethyl, 3-methoxypropyl, 3-ethoxypropyl, methylthiomethyl, ethylthiomethyl, 2-methylthioethyl, 2-ethylthioethyl, 3-methylthiopropyl and 3-ethylthiopropyl. Alkyl groups each having 1 to 6 carbon atoms (for example, methyl, ethyl, n-propyl, isopropyl, n-butyl, isobutyl, sec-butyl, tert-butyl, n-pentyl, isoamyl, tert-amyl, neopentyl and n-hexyl) are preferred among others. The cycloalkyl groups are preferably cycloalkyl groups each having 3 to 8 carbon atoms, which include, for example, cyclopropyl, cyclobutyl, cyclopentyl, cyclohexyl, cycloheptyl, cyclooctyl, tetrahydrofuran-2-yl and tetrahydrothiophen-2-yl. The cycloalkylalkyl groups are preferably straight chain or branched chain alkyl groups each having 1 to 8 carbon atoms which are substituted by cycloalkyl groups each having 3 to 8 carbon atoms. Examples thereof include cyclopentylmethyl, cyclohexylmethyl, 2-(cyclopentyl)ethyl, 2-(cyclohexyl)ethyl, cyclopentylthiomethyl and cyclohexylthiomethyl. As $R_3$, $C_{1-6}$ alkyl groups are more preferably used, and butyl groups (n-butyl, isobutyl, sec-butyl and tert-butyl) are most preferable among others. The carbon atom to which $R_3$ is attached is an asymmetric carbon atom, and the compounds represented by formula [B] of the present invention shows a significant antagonistic activity on endotherin receptors because $R_3$ is arranged in the L-configuration.

In formula [B], $R_4$ represents a heterocycle-lower alkyl group which may be substituted. The heterocycle-lower alkyl group means a lower alkyl group substituted by a heterocyclic group. The heterocyclic groups are preferably 5- and 6-membered heterocyclic groups each containing 1 to 4 heteroatoms such as O, S and N (for example, pyrrolyl, pyrrolinyl, pyrrolidinyl, imidazolyl, imidazolidinyl, piperidinyl, pyrazolyl, pyrazolidinyl, pyridyl, pyrimidyl, pyrazinyl, piperazinyl, pyridazinyl, triazolyl, tetrazolyl, dihydrotriazinyl, pyridyl, oxazolyl, isoxazolyl, oxadiazolyl, morpholinyl, furyl, thienyl, thiazolyl, isothiazolyl, thiazolinyl, thiadiazolyl and triazolidinyl), and condensed groups thereof with other rings such as benzene rings (for example, indolyl, isoindolyl, indolizinyl, benzimidazolyl, quinolyl, isoquinolyl, indazolyl, benzotriazolyl, tetrazopyridyl, tetrazopyridazinyl, benzoxazolyl, benzoxadiazolyl, benzothiazolyl and benzothiadiazolyl). These heterocyclic groups may each have 1 to 3 substituent groups, and the substituent groups on the carbon atoms include $C_{1-6}$ alkyl groups (such as methyl, ethyl, n-propyl and n-butyl), halogen atoms (such as fluorine, chlorine, bromine and iodine), hydroxyl, carboxyl, $C_{1-6}$ alkoxyl groups (such as methoxy, ethoxy, n-propoxy and n-butoxy), $C_{1-6}$ alkylcarbonyl groups (such as formyl and acetyl). Further, the substituent groups on the nitrogen atoms include $C_{1-6}$ alkyl groups (such as methyl, ethyl, n-propyl and n-butyl), $C_{1-6}$ alkylcarbonyl groups (such as formyl and acetyl) and hydroxy-$C_{1-6}$ alkyl groups (such as hydroxymethyl and 2-hydroxyethyl). On the other hand, the lower alkyl groups are preferably straight chain or branched chain alkyl groups each having 1 to 6 carbon atoms, which include, for example, methyl, ethyl, n-propyl, isopropyl, n-butyl, isobutyl, sec-butyl, tert-butyl, n-pentyl, isoamyl, tert-amyl, neopentyl and n-hexyl. Accordingly, heterocycle-$C_{1-6}$ alkyl groups are more preferable as the heterocycle-lower alkyl groups. Examples of such groups include 2-pyridyl-$C_{1-6}$ alkyl groups [for example, 2-pyridylmethyl and 2-(2-pyridyl)ethyl], 3-pyridyl-$C_{1-6}$ alkyl groups [for example, 3-pyridylmethyl and 2-(3-pyridyl)ethyl], 4-pyridyl-$C_{1-6}$ alkyl groups [for example, 4-pyridylmethyl and 2-(4-pyridyl)ethyl], imidazole-2-yl-$C_{1-6}$ alkyl groups [for example, imidazole-2-ylmethyl and 2-(imidazole-2-yl)ethyl], imidazole-4-yl-$C_{1-6}$ alkyl groups [for example, imidazole-4-ylmethyl and 2-(imidazole-4-yl)ethyl], indole-3-yl-$C_{1-6}$ alkyl groups [for example, indole-3-ylmethyl and 2-(indole-3-yl)ethyl], N-methylindole-3-yl-$C_{1-6}$ alkyl groups [for example, N-methylindole-3-ylmethyl and 2-(N- methylindole-3-yl)ethyl], N-ethylindole-3-yl-$C_{1-6}$ alkyl groups [for example, N-ethylindole-3-ylmethyl and 2-(N-ethylindole-3-yl)ethyl], N-hydroxymethylindole-3-yl-$C_{1-6}$ alkyl groups [for example, N-hydroxymethylindole-3-ylmethyl and 2-(N-hydroxymethylindole-3-yl)ethyl], N-formylindole-3-yl-$C_{1-6}$ alkyl groups [for example, N-formylindole-3-ylmethyl and 2-(N-formylindole-3-yl) ethyl], thiazole-4-yl-$C_{1-6}$ alkyl groups [for example, thiazole-4-ylmethyl and 2-(thiazole-4-yl)ethyl], and 5-fluoroindole-3-yl-$C_{1-6}$ alkyl groups [for example, 5-fluoroindole-3-ylmethyl and 2-(5-fluoroindole-3-yl) ethyl]. As $R_4$, indole-3-yl-$C_{1-6}$alkyl groups which may be substituted are preferred, and indole-3-ylmethyl, N-methylindole-3-ylmethyl, N-hydroxymethylindole-3-ylmethyl and the like are most preferred among others.

The carbon atom to which $R_4$ is attached is an asymmetric carbon atom, and the D-configuration of $R_4$ results in exhibition of significant antagonistic activity on endotherin receptors in the present invention.

In formula [B], X represents a group containing an aromatic ring. The groups containing aromatic rings include groups each formed by removing one hydrogen atom of an α-amino group from the α-amino acid containing at least one aromatic ring group, and alkylamino groups substituted by aromatic ring groups. That is, CO is preferably linked by an amide bond to X. The above-mentioned aromatic ring groups include aromatic hydrocarbon groups and aromatic heterocyclic groups which may be substituted. As the aromatic hydrocarbon groups, $C_{6-15}$ aromatic hydrocarbon groups such as phenyl and α-naphthyl are used. These hydrocarbon groups may contain 1 to 3 substituent groups selected from, for example, halogen atoms (for example, fluorine, chlorine, bromine and iodine), hydroxyl, $C_{1-6}$ alkyl groups (for example, methyl and ethyl), $C_{1-6}$ alkoxyl groups (for example, methoxy and ethoxy), carboxyl, $C_{1-6}$ alkyl-carbonyl groups (for example, formyl and acetyl) and $C_{1-6}$ alkoxycarbonyl groups (for example, acetoxyl). As the aromatic hydrocarbon groups which may be substituted, for example, phenyl, 4-fluorophenyl, 4-chlorophenyl, 4-bromophenyl, 4-hydroxyphenyl, 4-methoxyphenyl, 4-methylphenyl, 1-naphthyl and 2-naphthyl are frequently used. The aromatic heterocyclic groups are preferably 5- and 6-membered aromatic heterocyclic groups containing 1 to 4 heteroatoms such as O, S and N, and condensed groups thereof with other aromatic rings such as benzene rings (for example, 2-furyl, 3-furyl, 2-thienyl, 3-thienyl, thiazole-4-yl, 2-pyridyl, 3-pyridyl, 4-pyridyl, 2-pyranyl, indole-3-yl, N-methylindole-3-yl, 2-quinolyl and quinoxaline-2-yl). These aromatic heterocyclic groups may have 1 to 3 substituent groups, for example, similar to those which the above-mentioned aromatic hydrocarbon groups may contain.

In the α-amino acids each having at least one aromatic ring group include acids protected with protective groups and acids in each of which at least one aromatic ring group present in the α-amino acid is an aromatic ring contained in the substituent or protective group, as well as acids substituted by the substituent groups as described above. The α-amino acids may be natural α-amino acids [for example, Gly, Ala, Val, Leu, Ile, Ser, Thr, Glu, Asn, Phe, Trp, Met, His, Cys, Arg, Asn, Gln, Tyr, (I)Tyr and diiodo-Tyr] or nonnatural α-amino acids [for example, Phg, Cha, Nva, Nle, Pya(2), Pya(3) and Thi]. They may also be any of the L-, D- and DL-forms. The substituent or protective groups of the α-amino acids mainly include substituent or protective groups for the carboxyl group at the 1-position, which are preferably esters of the carboxyl group (for example, benzyl ester, diphenylmethyl ester and trityl ester) or amides thereof (for example, phenylamide, benzylamide, diphenylamide, dibenzylamide, 2-phenylethylamide, 2,2-diphenylethylamide, 1,2-diphenylethylamide, indole-3-ylmethylamide and 2-(indole-3-yl)ethylamide. The amides of the carboxyl group at the 1-position in the present invention also include amides with another α-amino acid. When the α-amino acid has a carboxyl group at a position other than the 1-position, the substituent or protective groups are preferably esters of the carboxyl group (for example, phenyl ester, benzyl ester, diphenylmethyl ester and trityl ester) or amides thereof [for example, phenylamide, benzylamide, diphenylmethylamide, diphenylamide, dibenzylamide, 2-phenylethylamide, 2,2-diphenylethylamide, 1,2-diphenylethylamide, indole-3-ylmethylamide and 2-(indole-3-yl)ethylamide]. Further, they may be substituent or protective groups for functional groups (for example, hydroxyl, thiol and amino) other than the carboxyl group and substituent groups on carbon atoms.

Examples of the "groups each formed by removing one hydrogen atom of an α-amino group from the α-amino acid containing at least one aromatic ring" in X include, for example, -Phe—OH, -Tyr—OH, -Trp—OH, -Phg—OH, -(m-F)Tyr—OH, -(p-F)Phe—OH, -(p-Cl)Phe—OH, -(p-Me)Phe—OH, -Trp(Me)—OH, -Trp(CHO)—OH, -Phe-Trp—OH, -Trp-Phe—OH, -Tyr-Trp—OH, -Trp-Phe—OH, -(m-F)Tyr-(p-F)Phe—OH, -Glu(OBzl)—OH, -Glu-OBzl, -Asp(OBzl)—OH, -Asp-OBzl, -Asp-Asp(OBzl)—OH, -Glu-(NBzl$_2$)—OH, -Glu(NHBzl)—OH, -Asp(NBzl$_2$)—OH, -Asp(NHBzl)—OH, -Glu-NBzl$_2$l -Glu-NHBzl, -Asp-NBzl$_2$, -Asp-NHBzl, -Glu-NHCHPhCH$_2$Ph, -Asp-NHCHPhCH$_2$Ph, -Glu-NHCH$_2$CHPh$_2$, -Asp-NHCH$_2$CHPh$_2$l -Glu(NHCHPhCH$_2$Ph) —OH, -Asp (NHCHPhCH$_2$Ph) —OH, -Glu(NHCH$_2$CHPh$_2$)—OH, -Asp (NHCH$_2$CHPh$_2$)—OH, -Glu(NHCH$_2$CH$_2$-Ind)—OH, -Asp (NHCH$_2$CH$_2$-Ind)—OH, -Glu-NHCH$_2$CH$_2$-Ind, -Asp-NHCH$_2$CH$_2$-Ind, -Trp-NH-Ind(OH), -Tyr-Iqu(OH), -(I)Tyr-Phe—OH, -Trp-Trp—OH, -Tyr(Bzl)-Phe—OH, -Tyr(Bzl)-Trp—OH, -(I)Tyr-Trp—OH, -(I)Tyr-Tyr—OH, -Trp-His—OH, -His-Trp—OH, -Tyr-His—OH, -His-Tyr—OH, -Phe-His—OH, -His-Phe—OH, -Phe-Trp—OH, -Phe-Tyr—OH and -Phe-Phe—OH. The amino acids which constitute these groups may be any of the L-, D- and DL-forms.

More specifically, the alkylamino groups of the "alkylamino groups substituted by aromatic groups" in X are, for example, $C_{1-10}$ alkylamino groups or $C_{3-10}$ cycloalkylamino groups. The aromatic ring groups are substituted on the carbon or nitrogen atoms of these alkylamino groups (for example, methylamino, ethylamino, n-propylamino, isopropylamino, n-butylamino, isobutylamino, sec-butylamino, tert-butylamino, n-pentylamino, n-hexylamino, n-decylamino, cyclopropylamino, cyclopentylamino, cyclohexylamino, cyclohexylmethylamino and 2-cyclohexylethylamino). The aromatic ring groups are those mentioned above. Examples of the "alkylamino groups substituted by aromatic ring groups" include, therefore, —NBzl$_2$, —NHBzl, —NHCHPhCH$_2$Ph —NHCH$_2$CHPh$_2$ and —NHCH$_2$CH$_2$-Ind.

In formula [B], $R_6$ represents a hydrogen atom, a lower alkyl group which may be substituted, or an aromatic group which may be substituted. The lower alkyl groups are preferably straight chain or branched chain alkyl groups each having 1 to 6 carbon atoms, which include, for example, methyl, ethyl, n-propyl, isopropyl, n-butyl, isobutyl, sec-butyl, tert-butyl, n-pentyl, isoamyl, tert-amyl, neopentyl and n-hexyl. These lower alkyl groups may contain 1 to 3 substituent groups. Examples of the substituent groups include aromatic ring groups [for example, $C_{6-15}$ aromatic hydrocarbon groups such as phenyl, naphthyl, indenyl, furyl, thienyl, pyridyl, quinolyl, pyranyl, imidazolyl, pyrimidyl, purinyl and indolyl), 5- and 6-membered aromatic heterocyclic groups containing 1 to 4 heteroatoms such as O, S and N, and condensed groups thereof with other aromatic rings (for example, benzene rings)]; sulfur-containing groups (for example, thione, mercapto, methylthio, ethylthio, phenylthio), an oxygen-containing group (for example, ketone, hydroxy, methoxy, ethoxy, phenoxy and benzyloxy), nitrogen-containing groups (for example, amino, N-methylamino, N-ethylamino and guanidino). The aromatic ring group are preferably aromatic hydrocarbon groups or aromatic heterocyclic groups which may be substituted. Preferred example of such aromatic hydrocarbon groups include those each having 6 to 12 carbon atoms (for example, phenyl, 1-naphthyl and 2-naphthyl). Preferred examples of the aromatic heterocyclic groups include 5- and 6-membered ring groups containing 1 to 4 heteroatoms such as O, S and N, and condensed groups thereof with other rings such as benzene rings (for example, furyl, thienyl, pyridyl, thiazolyl, imidazolyl and indolyl). The substituent groups for these aromatic hydrocarbon or aromatic heterocyclic groups include $C_{1-6}$ alkyl groups (such as methyl, ethyl, n-propyl and n-butyl), halogen atoms (such as fluorine, chlorine, bromine and iodine), $C_{1-6}$ alkoxyl groups (such as methoxy, ethoxy, n-propoxy, isopropoxy, n-butoxy and tert-butoxy), $C_{1-6}$ alkylthio groups (such as methylthio, ethylthio, n-propylthio, isopropylthio, n-butylthio and tert-butylthio), $C_{1-6}$ alkylcarbonyl groups (such as formyl and acetyl), $C_{1-6}$ alkoxycarbonyl groups (such as methoxycarbonyl, ethoxycarbonyl, isopropoxycarbonyl and tert-butoxycarbonyl). The number of the substituent groups is 1 to 3. In particular, preferred examples of $R_6$ include (1) lower alkyl groups (for example, $C_{1-6}$ alkyl groups such as methyl, ethyl, n-propyl, iso-propyl, n-butyl, isobutyl, sec-butyl, tert-butyl, n-pentyl, isoamyl, tert-amyl, neopentyl and n-hexyl), (2) 5- and 6-membered aromatic heterocyclic groups containing 1 to 4 heteroatoms such as O, S and N (for example, furyl, thienyl and pyridyl), and (3) lower alkyl groups substituted by aromatic heterocyclic groups [for example, 5- and 6-membered ring groups containing 1 to 4 heteroatoms such as O, S and N, or condensed groups thereof with other rings such as benzene rings (for example, furyl, thienyl, pyridyl, thiazolyl, imidazolyl and indolyl)], examples of the lower alkyl groups including 2-pyridylmethyl, 3-pyridylmethyl, 4-pyridylmethyl, indole-3-ylmethyl, N-methylindole-3-ylmethyl, N-formylindole-3-ylmethyl, 2-thienylmethyl, 3-thienylmethyl and 2-imidazolylmethyl. The carbon atom to which $R_6$ is attached is an asymmetric carbon atom. In the present invention, any of the L-, D- and DL-forms may be used. However, the D-form is more preferable. In formula [B], n represents an integer of 0, 1 or more, more preferably an integer of 0 or any of 1 to 4, and most preferably 0. When n is 0, the portion $-N(R_5)-CH(R_6)-(CH_2)_n-CO-$ is indicated by $-N(R_5)-CH(R_6)-CO-$. This portion is an α-amino acid residue [for example, Ala, Val, Leu, Ile, Trp, Pya(2) and Pya(3)]. Ala, Trp, Pya(2) and Pya(3) are preferred among others. In formula [B], m represents an integer of 2 or more, and preferably an integer of 2 to 6. The portion $-NH-(CH_2)_m-CO-$ represents βAla when m=2, GABA when m=3, and ϵAhx when m=5.

When the peptides represented by formula [B] are acidic compounds, salts thereof with bases are employed, and when the peptides are basic compounds, salts thereof with acids are employed. The salts of the peptides represented by formula [B] with bases include, for example, alkali metal salts (such as sodium salts and potassium salts), alkaline earth metal salts (such as calcium salts and magnesium salts), ammonium salts, and salts with organic bases (such as pyridinium salts and triethylammonium salts). The salts of the peptides with acids include, for example, inorganic acid salts (such as chloride, sulfate and nitrate), and organic acid salts (such as acetate, oxalate and p-toluenesulfonate). [Japanese Patent Application No. 4-27785 (EP-A-0,499,266)]

Peptides represented by formula [C] or pharmaceutically acceptable salts thereof:

[C]

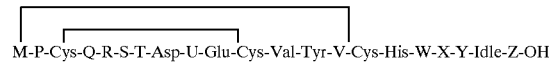

M-P-Cys-Q-R-S-T-Asp-U-Glu-Cys-Val-Tyr-V-Cys-His-W-X-Y-Idle-Z-OH wherein M represents a mercaptoacyl group; P, Q, R, S, T, U, V, W, X, Y and Z each represent amino acid residues, wherein an amino acid side chain of Y is either a substituted saturated aliphatic hydrocarbon group having 1 to 15 carbon atoms or an unsubstituted saturated aliphatic hydrocarbon group having 4 to 15 carbon atoms other than (1S)-1-methylpropyl.

Specifically, peptides or pharmaceutically acceptable salts thereof shown in Examples of Japanese Patent Application No. 4-27785 (EP-A-0,499,266) are used.

In the peptides of the present invention represented by formula (C), the saturated aliphatic hydrocarbon groups with 1 to 15 carbon atoms as the amino acid side chains of Y include alkyl, cycloalkyl and cycloalkyl-alkyl groups in which the alkyl groups may be straight or branched. As the alkyl groups, preferred are $C_{1-10}$ alkyl groups, which include, for example, methyl, ethyl, n-propyl, isopropyl, n-butyl, isobutyl, sec-butyl, tert-butyl, n-pentyl, isopentyl, neopentyl, n-hexyl, n-heptyl, n-octyl, n-nonyl and n-decyl. As the cycloalkyl groups, preferred are $C_{3-10}$ cycloalkyl groups, which include, for example, cyclopropyl, cyclobutyl, cyclopentyl, cyclohexyl, cycloheptyl, cyclooctyl and norbornyl. As the cycloalkyl-alkyl groups, preferred are $C_{3-10}$ cycloalkyl-$C_{1-6}$ alkyl groups, which include, for example, cyclopropylmethyl, cyclobutylmethyl, cyclopentylmethyl, cyclohexylmethyl, cycloheptylmethyl, 1-cyclopentylethyl, 1-cyclohexylethyl, 2-cyclopentylethyl, 2-cyclohexylethyl, 3-cyclohexylpropyl, 4-cyclohexylbutyl and 5-cyclohexyl-propyl.

The above-mentioned saturated hydrocarbon groups may also be substituted, and the substituent groups include sulfur-containing groups (such as thione, mercapto, methylthio, ethylthio, n-propylthio, isopropylthio, n-butylthio, isobutylthio, t-butylthio, phenylthio, cyclopentylthio, cyclohexylthio and thienyl), oxygen-containing substituent groups (such as ketone, hydroxyl, methoxy, ethoxy, n-propoxy, isopropoxy, n-butoxy, isobutoxy, t-butoxy, n-pentyloxy, cyclohexyloxy, phenoxy, benzyloxy and furyl), nitrogen-containing groups (such as amino, N-methylamino, N-ethylamino, N-n-propylamino, N-isopropylamino, N-n-butylamino, N-isobutylamino, N-t-butylamino, N-n-pentylamino, N-n-hexylamino, N-cyclohexylamino, N,N-dimethylamino, N,N-diethylamino, N,N-di-n-propylamino, N,N-di-isopropylamino, N,N-di-n-butylamino, N,N- diisobutylamino, N,N-di-t-butylamino, N,N-di-n-pentylamino, N,N-di-n-hexylamino, N,N-dicyclohexylamino, nitro, guanidino, pyrrolidino, piperidino, indolyl and imidazolyl), aromatic hydrocarbon group (such as phenyl, 1-naphthyl and 2-naphthyl) and halogen groups (such as chloro, bromo and fluoro).

The unsubstituted saturated aliphatic hydrocarbon groups with 4 to 15 carbon atoms other than (1S)-1-methylpropyl as the amino acid side chains of Y, include alkyl, cycloalkyl and cycloalkyl-alkyl groups in which alkyl may be straight or branched. As the alkyl groups, preferred are $C_{4-10}$ alkyl groups, which include, for example, n-butyl, isobutyl, t-butyl, n-pentyl, isopentyl, neopentyl, n-hexyl, n-heptyl, n-octyl, n-nonyl and n-decyl. As the cycloalkyl groups, preferred are $C_{4-10}$ cycloalkyl groups, which include, for example, cyclobutyl, cyclopentyl, cyclohexyl, cycloheptyl, cyclooctyl and norbornyl. As the cycloalkyl-alkyl groups, preferred are $C_{3-10}$ cycloalkyl-$C_{1-6}$alkyl groups, which include, for example, cyclopropylmethyl, cyclobutylmethyl, cyclopentylmethyl, cyclohexylmethyl, cycloheptylmethyl, 1-cyclopentylethyl, 1-cyclohexylethyl, 2-cyclopentylethyl, 2-cyclohexylethyl, 2,2-dicyclopentylethyl, 2,2-dicyclohexylethyl, 3-cyclohexylpropyl, 4-cyclohexylbutyl and 5-cyclohexylpropyl.

As the amino acid side chain of Y, a hydrocarbon group branched at its β-positioned carbon atom is more preferred. Examples thereof include isobutyl, neopentyl, cyclopropylmethyl, cyclobutylmethyl, cyclopentylmethyl, cyclohexylmethyl, cycloheptylmethyl, 2-cyclohexylpropyl, 2,2-dicyclohexylethyl, 2-mercaptopropyl, 2-thienylmethyl, 2-hydroxypropyl, 2-furylmethyl, 3-indolylmethyl, 4-imidazolylmethyl and benzyl.

In the present invention, the mercaptoacyl groups represented by M which may be substituted are carboxylic acid-derived acyl groups having mercapto groups, and the carboxylic acids include aliphatic, alicyclic and aromatic carboxylic acids. Preferred examples of the aliphatic mercaptoacyl groups include mercapto $C_2$–$C_{10}$ alkanoyl groups such as 3-mercaptopropionyl and 4-mercaptobutyryl. Preferred examples of the alicyclic mercaptoacyl groups include mercapto $C_3$–$C_8$ cycloalkylcarbonyl groups such as 3-mercaptocyclopentylcarbonyl. Preferred examples of the aromatic mercaptoacyl groups include $C_6$–$C_{14}$ arylcarbonyl groups such as 4-mercaptobenzoyl, 4-mercaptophenylacetyl and 3-mercapto-3-phenylpropionyl. The above-mentioned aliphatic and alicyclic groups are preferably used. The mercaptoacyl groups may be substituted. Substituent groups on the mercaptoacyl groups include amino and hydroxyl groups. A mercaptoacyl group substituted by an amino group at the α-position of the acyl group is more preferred. Preferred examples thereof include Cys, homocysteine and 3-mercapto-D-valine (penicillamine). The most preferred examples of the unsubstituted mercaptoacyl groups and the substituted mercaptoacyl groups are 3-mercaptopropionyl and Cys, respectively.

In the present invention, the amino acid residue represented by P, Q, R, S, T, U, V, W, X, Y or Z may be either a natural amino acid residue or a synthetic amino acid residue, and may be any of the L-, D- and DL-forms. Accordingly, P, Q, R, S, T, U, V, W, X, Y and Z can also be expressed as

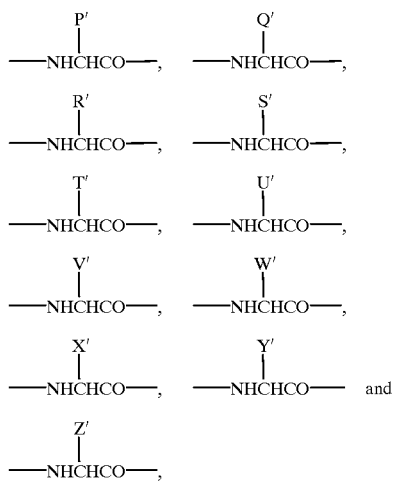

respectively. The compound of formula [C] can therefore be represented by the following formula [C']:

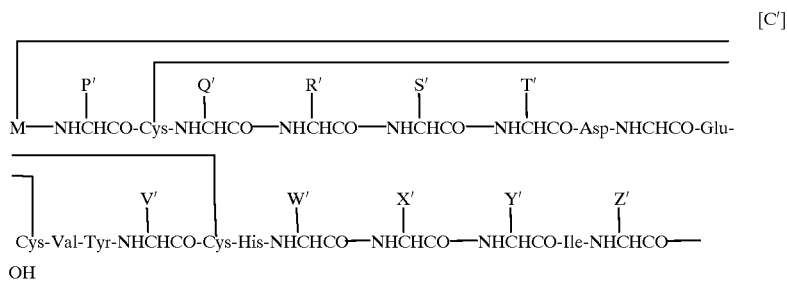

[C']

wherein P', Q', R', S', T', U', V', W', X' and Z' each represent hydrogen atoms or hydrocarbon groups with 1 to 15 carbon atoms which may be substituted, and Y' represents either a substituted saturated aliphatic hydrocarbon group having 1 to 15 carbon atoms or an unsubstituted saturated aliphatic hydrocarbon group having 4 to 15 carbon atoms other than (1S)-1-methylpropyl. The hydrocarbon groups each having 1 to 15 carbon atoms include aliphatic hydrocarbon groups, aromatic hydrocarbon groups and aliphatic-aromatic hydrocarbon groups.

The aliphatic hydrocarbon groups represented by P' to X' and Z' described above may be straight, branched or cyclic groups which may be saturated or unsaturated. Examples thereof include methyl, ethyl, n-propyl, iso-propyl, n-butyl, isobutyl, sec-butyl, t-butyl, n-pentyl, isopentyl, neopentyl, cyclopentyl, n-hexyl, cyclohexyl, n-heptyl, cycloheptyl, n-octyl, n-nonyl, n-decyl, cyclopentylmethyl and cyclohexylmethyl. The substituted aliphatic hydrocarbon groups include methylthiomethyl, ethylthiomethyl, n-propylthiomethyl, isopropylthiomethyl, n-butylthiomethyl, t-butylthiomethyl, 2-methylthioethyl, 2-ethylthioethyl, 2-t-butylthioethyl, mercaptomethyl, 1-mercaptoethyl, 2-mercaptoethyl, phenylthiomethyl, 1-phenylthioethyl, 2-phenylthioethyl, benzylthiomethyl, 4-methoxyphenylthiomethyl, 4-methoxybenzylthiomethyl, 4-methylbenzylthiomethyl, 4-nitrobenzylthiomethyl, 4-pyridylbenzylthiomethyl, hydroxymethyl, 1-hydroxyethyl, 2-hydroxyethyl, methoxymethyl, ethoxymethyl, n-propoxy-methyl, isopropoxymethyl, n-butoxymethyl, t-butoxymethyl, n-pentyloxymethyl, cyclopentyloxymethyl, n-hexyloxymethyl, cyclohexyloxymethyl, 1-methoxyethyl, 1-ethoxyethyl, 1-propoxyethyl, 1-isopropoxyethyl, 1-n-butoxyethyl, 1-isobutoxyethyl, 1-t-butoxyethyl, phenoxymethyl, 1-phenoxyethyl, 2-phenoxyethyl, benzyloxymethyl, 2-benzyloxyethyl, carboxymethyl, 1-carboxyethyl, 2-carboxyethyl, methoxycarbonylmethyl, ethoxycarbonylmethyl, n-propoxycarbonylmethyl, isopropoxycarbonylmethyl, n-butoxycarbonylmethyl, isobutoxycarbonylmethyl, t-butoxycarbonylmethyl, n-pentyloxycarbonylmethyl, cyclopentyloxycarbonylmethyl, n-hexyloxycarbonylmethyl, cyclohexyloxycarbonylmethyl, cycloheptyloxycarbonylmethyl, cyclooctyloxycarbonylmethyl, carboxyethyl, methoxycarbonylethyl, ethoxycarbonylethyl, n-propoxycarbonylethyl, iso-propoxycarbonylethyl, n-butoxycarbonylethyl, isobutoxycarbonylethyl, t-butoxycarbonylethyl, n-pentyloxycarbonylethyl, cyclopentyloxycarbonylethyl, n-hexyloxycarbonylethyl, cyclohexyloxycarbonylethyl, cycloheptyloxycarbonylethyl, cyclooctyloxycarbonylethyl, 2-aminoethyl, 2-(N-methylamino)ethyl, 2-(N,N-dimethylamino)ethyl, 3-aminopropyl, 3-(N,N-diethylamino)propyl, 2-guanidinoetyl, 3-guanidinopropyl, aminocarbonylmethyl, N-methylaminocarbonylmethyl, N-ethylaminocarbonylmethyl, N-n-propylaminocarbonylmethyl, N-isopropylaminocarbonylmethyl, N-n-butylaminocarbonylmethyl, N-isobutylaminocarbonylmethyl, N-t-butylaminocarbonylmethyl, N-n-pentylaminocarbonylmethyl, N-isopentylaminocarbonylmethyl, N-neopentylaminocarbonylmethyl, N-n-hexylaminocarbonylmethyl, N-cyclohexylaminocarbonylmethyl, N,N-dimethylaminocarbonylmethyl, N,N-diethylaminocarbonylmethyl, N,N-di-n-propylaminocarbonylmethyl, N,N-diisopropylaminocarbonylmethyl, N,N-di-n-butylaminocarbonylmethyl, N,N-diisobutylaminocarbonylmethyl, N,N-di-t-butylaminocarbonylmethyl, N,N-di-n-pentylaminocarbonylmethyl, N,N-diisopentylaminocarbonylmethyl, N,N-dineopentylaminocarbonylmethyl, N,N-di-n-hexylaminocarbonylmethyl, N,N-dicyclohexylaminocarbonylmethyl, pyrrolidinocarbonylmethyl, piperidinocarbonylmethyl, aminocarbonylethyl, N-methylaminocarbonylethyl, N-ethylaminocarbonylethyl, N-n-propylaminocarbonylethyl, N-isopropylaminocarbonylethyl, N-n-butylaminocarbonylethyl, N-isobutylaminocarbonylethyl, N-t-butylaminocarbonylethyl, N-n-pentylaminocarbonylethyl, N-cyclopentylaminocarbonylethyl, N-n-hexylaminocarbonylethyl, N-cyclohexylaminocarbonylethyl, N,N-dimethylaminocarbonylethyl, N,N-diethylaminocarbonylethyl, N,N-di-n-propylaminocarbonyl-ethyl, N,N-diisopropylaminocarbonylethyl, N,N-di-n-butylaminocarbonylethyl, N,N-diisobutylaminocarbonylethyl, N,N-di-t-butylaminocarbonylethyl, N,N-di-n-pentylaminocarbonylethyl, N,N-dicyclopentylaminocarbonylethyl, N,N-di-n-hexylaminocarbonylethyl, N,N-dicyclohexylaminocarbonyl-ethyl, 3-indolylmethyl, 4-imidazolylmethyl, 2-thienyl-methyl, 2-furylmethyl, pyrrolidinocarbonylethyl and piperidinocarbonylethyl.

Examples of the aromatic hydrocarbon groups and aliphatic-aromatic hydrocarbon groups represented by P' to X' and Z' include phenyl, 1-naphthyl, 2-naphthyl, phenylmethyl, 1-phenylethyl, 2-phenylethyl, 1-naphthylmethyl, 2-naphthylmethyl and 9-anthranylmethyl. Examples of the substituted aromatic hydrocarbon groups and aliphatic-aromatic hydrocarbon groups include 4-hydroxyphenyl, 4-hydroxyphenylmethyl, 4-methoxyphenyl-methyl, 4-ethoxyphenylmethyl, 4-n-propoxyphenylmethyl, 4-isopropoxyphenylmethyl, 4-n-butoxyphenylmethyl, 4-isobutoxyphenylmethyl, 4-t-butoxyphenylmethyl, 4-n-pentyloxyphenylmethyl, 4-cyclopentyloxyphenylmethyl, 4-n-hexyloxyphenylmethyl, 4-cyclohexyloxyphenylmethyl, 4-aminophenylmethyl, 4-dimethylaminophenylmethyl, 4-diethyl-aminophenylmethyl, 4-di-n-propylaminophenylmethyl, 4-diisopropylaminophenylmethyl, 4-di-n-butylaminophenylmethyl, 4-pyrrolidinophenylmethyl, 4-piperidinophenylmethyl, 4-nitrophenylmethyl, 4-fluorophenylmethyl, 3-fluorophenylmethyl, 2-fluorophenylmethyl, 4-chlorophenylmethyl, 3-chlorophenylmethyl and 2-chlorophenylmethyl.

Y' corresponds to the amino acid side chain of Y, and therefore represents a substituted saturated aliphatic hydrocarbon group having 1 to 15 carbon atoms or an unsubstituted saturated aliphatic hydrocarbon group having 4 to 15 carbon atoms other than (1S)-1-methylpropyl.

Preferred examples of the amino acid residues represented by P to Z (having P' to Z', respectively) are more specifically described below.

P is an amino acid residue having an alkyl group which may be substituted as the amino acid side chain (P'). A hydroxyl group is preferred as this substituent group. Specifically, the substituent groups include Ala as well as Ser and Thr.

Q includes, for example, Ser, Thr, Phe and Ala. Ser and Ala are preferred among others.

R is an amino acid residue having an alkyl group which may be substituted as the amino acid side chain (R'). A hydroxyl group is preferred as this substituent group. Specifically, the substituent groups include Ala as well as Ser and Thr.

S is an amino acid residue having a lipophilic portion as the amino acid side chain (S'). Examples thereof include Leu, Ala, Tyr, Trp and Met, and Leu is preferred.

T includes Met, Leu, Lys, Ala, Nle and Glu, and Met, Ala and Nle are preferred.

U includes Lys, Ala and Glu.

As V, aromatic amino acids are preferred, with the monocyclic ones preferred over the bicyclic ones. Preferred examples thereof include Trp as well as Phe and Tyr.

W includes Gln as well as Leu.

As Z, aromatic amino acids are preferred, with bicyclic ones being more preferred. Preferred examples thereof include Trp and Trp having a substituent group [for example, N-(indole)-formyltryptophan], 3-(1-naphthyl)-alanine and 3-(2-naphthyl)alanine. Substituted compounds such as N-(indole)-formyl compounds are often used in place of tryptophan easily decomposed by oxidation, because of oxidation of S—S bonds in synthesis.

As X, amino acid residues other than Asp are preferred, and particularly, amino acid residues having hydroxyl groups are preferred due to their strong binding affinity for endothelin receptors. Preferred examples thereof include Ser and Thr. In addition, amino acid residues such as Asn and Gly are also preferably used.

Preferred examples of Y include amino acid residues having the amino acid side chain (Y') branched at the 2-position, for example, Leu, Cha, Phe, γLeu and Asn.

Although embodiments of the present invention have emphasized substitution of (Y) at the 19-position, further combinations of substitution at the 19-position and substitution at the 18-position are also important. Such combinations of the 18-position and the 19-position include ThrLeu, ThrγLeu, ThrCha, ThrPhe, ThrAsn, SerLeu, AsnLeu and GlyLeu. The combinations of ThrLeu, ThrγLeu and ThrCha are especially preferred.

Examples of the peptides of the present invention represented by formula [C] include the following peptides:

1  CysSerCysSerSerLeuMetAspLys-GluCysValTyrPheCysHisLeuThrLeuIleTrp (Abbreviation [Thr$^{18}$, Leu$^{19}$]-ET-1; SQ ID NO:1)
2  CysSerCysSerSerLeuMetAspLys-GluCysValTyrPheCysHisLeuThrChaIleTrp (Abbreviation [Thr$^{18}$, Cha$^{19}$]-ET-1; SQ ID NO:2)
3  CysSerCysSerSerLeuMetAspLys-GluCysValTyrPheCysHisLeuThrPheIleTrp (Abbreviation [Thr$^{18}$, Phe$^{19}$]-ET-1; SQ ID NO:3)
4  CysSerCysSerSerLeuMetAspLysGluCysValTyrPheCysHisLeuThrγLeuIleTrp (Abbreviation [Thr$^{18}$, γLeu$^{19}$]-ET-1; SQ ID NO:4)
5  CysSerCysSerSerLeuMetAspLys-GluCysvalTyrPheCysHisLeuThrAsnIleTrp (Abbreviation [Thr$^{18}$, Asn$^{19}$]-ET-1; SQ ID NO:5)
6  CysSerCysSerSerLeuMetAspLys-GluCysvalTyrPheCysHisLeuSerLeuIleTrp (Abbreviation [Ser$^{18}$, Leu$^{19}$]-ET-1; SQ ID NO:6)
7  CysSerCysSerSerLeuMetAspLys-GluCysValTyrPheCysHisLeuAsnLeuIleTrp (Abbreviation [Asn$^{18}$, Leu$^{19}$]-ET-1; SQ ID NO:7)
8  CysSerCysSerSerLeuMetAspLys-GluCysvalTyrPheCysHisLeuGlyLeuIleTrp (Abbreviation [Glyl$^{18}$, Leu$^{19}$]-ET-1; SQ ID NO:8)
9  CysThrCysPheThrTyrLysAspLys-GluCysValTyrTyrCysHisLeuThrLeuIleTrp (Abbreviation [Thr$^{18}$, Leu$^{19}$]-ET-3; SQ ID NO:9)
10  CysSerCysSerSerLeuMetAspAla-GluCysValTyrPheCysHisLeuThrLeuIleTrp (Abbreviation [Ala$^9$, Thr$^{18}$, Leu$^{19}$]-ET-1; SQ ID NO:10)
11  MprSerCysSerSerLeuMetAspLys-GluCysValTyrPheCysHisLeuThrLeuIleTrp (Abbreviation [Mpr$^1$, Thr$^{18}$, Leu$^{19}$]-ET-1; SQ ID NO:11)
12  CysAlaCysSerSerLeuMetAspLys-GluCysValTyrPheCysHisLeuThrLeuIleTrp (Abbreviation [Ala$^2$, Thr$^{18}$, Leu$^{19}$]-ET-1; SQ ID NO:12)
13  CysSerCysAlaSerLeuMetAspLys-GluCysValTyrPheCysHisLeuThrLeuIleTrp (Abbreviation [Ala$^4$, Thr$^{18}$, Leu$^{19}$]-ET-1; SQ ID NO:13)
14  CysSerCysSerAlaLeuMetAspLys-GluCysValTyrPheCysHisLeuThrLeuIleTrp (Abbreviation [Ala$^5$, Thr$^{18}$, Leu$^{19}$]-ET-1; SQ ID NO:14)
15  CysSerCysSerSerAlaMetAspLys-GluCysValTyrPheCysHisLeuThrLeuIleTrp (Abbreviation [Ala$^6$, Thr$^{18}$, Leu$^{19}$]-ET-1; SQ ID NO:15)
16  CysSerCysSerSerLeuAlaAspLys-GluCysValTyrPheCysHisLeuThrLeuIleTrp (Abbreviation [Ala$^7$, Thr$^{18}$, Leu$^{19}$]-ET-1; SQ ID NO:16)
17  CysSerCysSerSerLeuNleAspLys-GluCysValTyrPheCysHisLeuThrLeuIleTrp (Abbreviation [Nle$^7$, Thr$^{18}$, Leu$^{19}$]-ET-1; SQ ID NO:17)
18  CysSerCysSerSerTrpLeuAspLys-GluCysValTyrPheCysHisLeuThrLeuIleTrp (Abbreviation [Thr$^{18}$, Leu$^{19}$]-ET-2; SQ ID NO:18)

[Japanese Patent Application No. 3-503831 (WO91/13089)]

Peptide derivatives represented by formula [D] or pharmaceutically acceptable salts thereof:

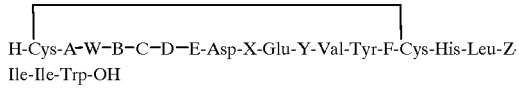

[D]

wherein A, B, C, D, E and F each represent amino acid residues, and satisfy any one condition of (i) A=Ser, C=ser, D=Leu, E=Met and F=Phe, (ii) A=Ser, B=Ser, C=Ser, D=Trp, E=Leu and F=Phe, and (iii) A=Thr, B=Phe, C=Thr, D=Tyr, E=Lys and F=Tyr; and W, X, Y and Z each represent amino acid residues, and at least one of W and Y is an amino acid residue other than an L-alanine residue or other than an L-cysteine residue, or X is an amino acid residue other than an L-lysine residue, or Z is an amino acid residue other than an L-aspartic acid residue.

Specifically, peptide derivatives or pharmaceutically acceptable salts thereof shown in Examples of Japanese Patent Application No. 3-503831 (WO91/13089) are used.

[EP-A-436,189]

Cyclic pentapeptides represented by formula [E] or pharmaceutically acceptable salts thereof:

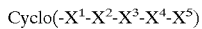

[E]

wherein $X^n$ represents an amino acid residue (wherein n represents an integer of 1 to 5); $X^1$ represents D-Phe, D-Tyr, D-Tha, D-Tza, D-Nal, D-Bta, D-Trp, D-Trp(O), D-Trp (CHO) or D-Trp[(CH$_2$)$_m$COR$^1$] (wherein m represents an integer of 0 to 6, and R$^1$ represents a hydroxyl group, a C$_{1-6}$ alkoxyl group, an amino group or a C$_{1-6}$ monoalkylamino group); $X^2$ represents D-Asp, D-Glu or D-Cys(O$_3$H); $X^3$ represents Pro, Hys, Pip, Thz, β-Ala, Gly, Ala, α-Aba, Aib, Val, Nva, Leu, Ile, alle, Nle, Met, Met(O), Met(O$_2$), Phe, Tza, Tha, Tyr, Trp, His, Arg, Lys, Lys(CHO), Orn, Orn (CHO), Asn, Gln, Asp, Glu, Cys(O$_3$H), Cys, Ser or Thr, and a hydrogen atom on an α-amino group may be substituted by a C$_{1-6}$ alkyl or C$_{3-7}$ cycloalkyl group which may have a group selected from the group consisting of a imidazolyl group, a carboxyl group and a hydroxyl group; $X^4$ represents D-Ala, D-Thr, D-αAba, D-Val, D-Nva, D-Leu, D-Ile, D-alle, D-Nle, D-tertLeu, D-Cpg, D-Chg, D-Cpg, D-Pen, Aib, Ac3c, Ac4c, Ac5c, Ac6c, Ac7c, D-Phg, D-Thg, D-Fug, D-Tzg or D-Itg, and a hydrogen atom on an α-amino group may be substituted by a C$_{1-3}$ alkyl group; and $X^5$ represents Pro, Pip, Thz, His, Ala, aAba, Val, Nva, Leu, Ile, alle, Nle, Met, C$_3$al, C4al, C5al or C6al, and a hydrogen atom on an α-amino group may be substituted by a C$_{1-6}$ alkyl group.

Specifically, cyclic pentapeptides or pharmaceutically acceptable salts thereof shown in Examples of EP-A-436, 189 are used. In particular, the following compounds are preferably used:

Cyclo(-D-Asp-Pro-D-Val-Leu-D-Trp-),
Cyclo(-D-Cys (O₃H)-Pro-D-Val-Leu-D-Trp-),
Cyclo(-D-Asp-Pro-D-Thg(2)-Leu-D-Trp-), and
Cyclo(-D-Asp-Pro-D-Cpg-Leu-D-Trp-)

[EP-A-457,195]

Peptides represented by formula [F] or pharmaceutically acceptable salts thereof:

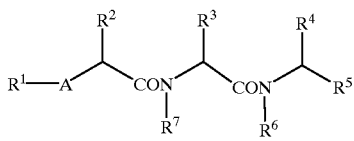

[F]

wherein $R^1$ represents a hydrogen atom or an acyl group; $R^2$ represents a lower alkyl group, an ar(lower)alkyl group which may be substituted, a cyclo(lower)alkyl(lower)alkyl group or a heterocyclic (lower) alkyl group which may be substituted; $R^3$ represents a heterocyclic (lower) alkyl group or an ar(lower)alkyl group which may be substituted; $R^4$ represents a hydrogen atom or a lower alkyl group which may be substituted; $R^5$ represents a carboxyl group, a protected carboxyl group, a carboxyl(lower)alkyl group or a protected carboxyl(lower)alkyl group; $R^6$ represents a hydrogen atom or a lower alkyl group which may be substituted; $R^7$ represents a hydrogen atom or a lower alkyl group; and A represents —O—, —NH—, a lower alkylamino group or a lower alkylene group; with the proviso that the compounds of formula [F] have an absolute configuration represented by the following partial formulae:

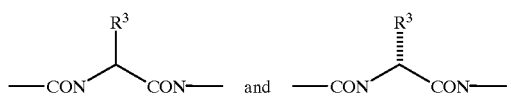

when $R^2$ is an (S)-isobutyl group, $R^3$ is an N-(dichlorobenzyloxycarbonyl)indole-3-ylmethylene group, $R^4$ is a methyl group, R is a methoxycarbonyl group, $R^6$ is a hydrogen atom, $R^7$ is a hydrogen atom, and A is —NH—. In the above definition, "lower" means $C_{1-6}$.

Specifically, peptides or pharmaceutically acceptable salts thereof shown in Examples of EP-A-457,195 are used.

[EP-A-510,526]

Compounds represented by formula [G] or salts thereof:

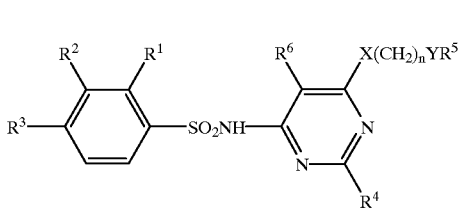

[G]

wherein $R^1$ represents a lower alkyl group, a lower alkoxyl group, a lower alkylthio group, a halogen atom or a trifluoromethyl group; $R^2$ represents a halogen atom, a lower alkoxyl group, a hydroxy-lower alkoxyl group or a trifluoromethyl group; $R^3$ represents a hydroxyl group, a halogen atom, an alkylthio group, a cycloalkyl group, a hydroxy-lower alkyl group, a hydroxy-lower alkoxyl group, a hydroxyimino-lower alkyl group, a lower alkenyl group, an oxy-lower alkyl group, a trifluoromethyl group, a trifluoromethoxyl group, a lower alkoxyl group, a lower alkoxyl-lower alkoxyl group or an aryl-lower alkoxyl group, and $R^2$ and $R^3$ may form butadienyl; $R^4$ represents a lower alkyl group, an aryl group or heterocyclic aryl group; $R^5$ represents a lower alkanoyl group, a benzoyl group, a heterocyclic carbonyl group or a tetrahydropyran-2-yl group; $R^6$ represents

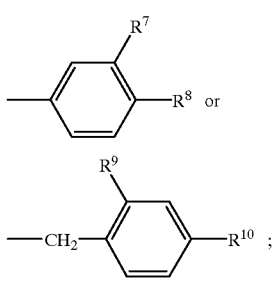

represents a lower alkoxyl group or a nitro group; $R^8$ represents a halogen atom, a lower alkyl group, a lower alkoxyl group, a lower alkylthio group, a nitro group, a hydroxyl group, an amino group or a trifluoromethyl group, and $R^7$ and $R^8$ may form butadienyl; $R^9$ represents a halogen atom, a lower alkyl group, a lower alkoxyl group, a lower alkylthio group or a trifluoromethyl group; $R_{10}$ represents a halogen atom, a lower alkyl group, a lower alkoxyl group or a lower alkylthio group; X and Y each represent O, S or NH; and n represents 2, 3 or 4. In the above definition, "lower" means $C_{1-7}$.

Specifically, compounds or salts thereof shown in Examples of EP-A-510,526 are used.

[WO92/12991]

Triterpene derivatives represented by formula [H]:

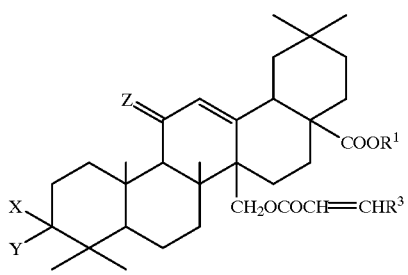

[H]

wherein $R^1$ represents a hydrogen atom or a metabolic ester residue; $R^3$ represents an aryl group which may be substituted or an aromatic heterocycle which may be substituted; one of X and Y is hydroxyl and the other is hydrogen, or both X and Y are combined to form oxo; and Z represents an oxygen atom or two hydrogen atoms.

Specifically, triterpene derivatives shown in Examples of WO92/12991 are used.

[Japanese Patent Unexamined Publication No. 4-288099]

Endothelin derivatives represented by formula [I]:

[I]

wherein Xaa1 represents Tyr, Phe or Ala; Xaa2 represents Asp or Gly; and Xaa3 represents Trp or Phe.

Specifically, endothelin derivatives shown in Examples of Japanese Patent Unexamined Publication No. 4-288099 are used.

[EP-A-496,452]

Cyclic peptides represented by formula [J]:

ethyl group or —OCH$_2$COOR$^a$; R$^3$ represents a hydrogen atom, a halogen atom, a lower alkyl group, a lower alkylthio group, a trifluoromethyl group, a cycloalkyl group or a lower alkoxyl group, and R$^2$ and R$^3$ may form butadienyl, methylenedioxy, ethylenedioxy or isopropylidene; R$^4$ represents a hydrogen atom, a lower alkyl group, a cycloalkyl group, a trifluoromethyl group, a lower alkoxyl group, a lower alkylthio group, a lower alkylthio-lower alkyl group, a hydroxy-lower alkyl group, a hydroxy-lower alkoxyl group, a lower alkoxy-lower alkyl group, hydroxy-lower alkoxy-lower alkyl group, hydroxy-lower alkoxy-lower alkoxyl group, a lower alkylslufinyl group, a lower alkylsulfonyl group, a 2-methoxy-3-hydroxypropoxyl group, a 2-hydroxy-3-phenylpropyl group, an amino-lower alkyl group, a lower alkylamino-lower alkyl group, a di-lower alkylamino-lower alkylamino group, a lower alkylamino group, a di-lower alkylamino group, an arylamino group, an aryl group, an arylthio, an aryloxy group, an aryl-lower alkyl

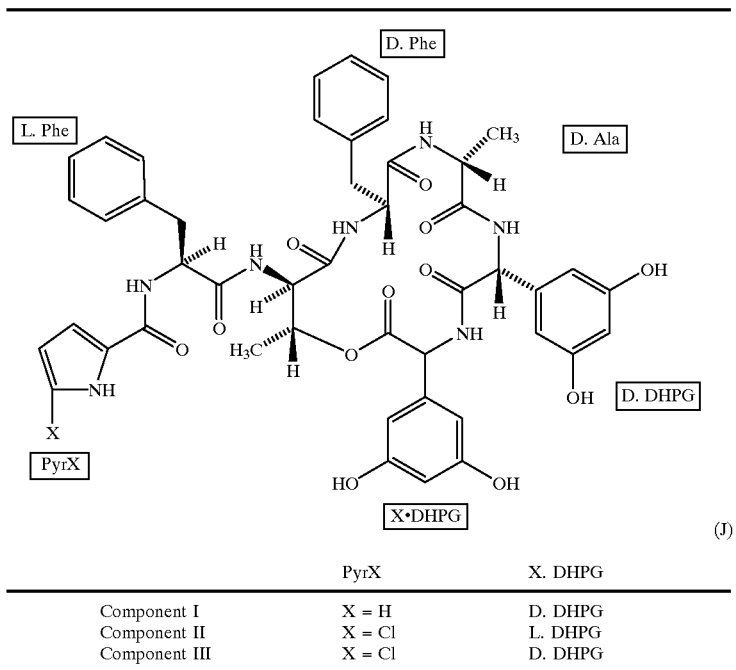

(J)

| | PyrX | X. DHPG |
|---|---|---|
| Component I | X = H | D. DHPG |
| Component II | X = Cl | L. DHPG |
| Component III | X = Cl | D. DHPG |

[EP-A-526,708]

Compounds represented by formula [K]:

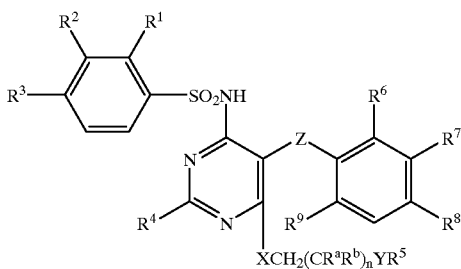

[K]

wherein R$^1$ represents a hydrogen atom, a lower alkyl group, a lower alkoxyl group, a lower alkylthio group, a halogen atom or a trifluoromethyl group; R$^2$ represents a hydrogen atom, a halogen atom, a lower alkoxyl group, a trifluoromgroup or a heterocycle; R$^5$ represents a hydrogen atom, a lower alkyl group, a lower alkanoyl group, a benzoyl group, a heterocyclic carbonyl group, a heterocyclic methyl group or a tetrahydropyran-2-yl group; R$^6$ to R$^9$ each represent hydrogen atoms, halogen atoms, trifluoromethyl groups, lower alkyl groups, lower alkoxyl groups, lower alkylthio groups, hydroxyl groups, hydroxymethyl groups, cyano groups, carboxyl groups, formyl groups, methylsulfinyl groups, methylsulfonyl groups, methylsulfonyloxy groups or lower alkoxycarbonyloxy groups; R$^7$ may combine with R$^6$ or R$^8$ to form butadienyl, methylenedioxy, ethylenedioxy or isopropylidenedioxy; Z represents —O—, —S—, ethylene, vinylene, —CO—, —OCHR$^{10}$— or —SCHR$^{10}$—, wherein R$^{10}$ represents a hydrogen atom or a lower alkyl group; X and Y each represent O, S or NH; YR$^5$ represents a lower alkylslufinyl group or —OCH$_2$CH(OR$^c$)CH$_2$—OR$^d$; R$^a$, R$^b$, R$^c$ and R$^d$ each represent hydrogen atoms or lower alkyl groups; R$^c$ and R$^d$ each represent methylene, ethylene or isopropylidene; and n represents 1, 2 or 3.

Specifically, compounds shown in Examples of EP-A-460,708 are used.

[EP-A-460,679]

Peptide derivatives represented by formula [L] or pharmaceutically acceptable salts thereof:

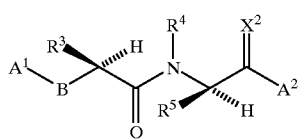
[L]

wherein $A^1$ is a group represented by formula (1), $R^{11}$—CO—, [wherein $R^{11}$ represents a lower alkyl group, a cycloalkyl group, a cycloalkyl-lower alkyl group, a group represented by $Ar^1$—$(CH_2)_p$— (wherein $Ar^1$ represents a phenyl group, a furyl group or a thienyl group, and p represents 0, 1 or 2), a 1,3-dithio-2-iridenemethyl group or 1,3-dithiol-2-iridene(lower alkoxycarbonyl)methyl group], a group represented by formula (2), $R^{12}O$—CO—, (wherein $R^{12}$ represents a lower alkyl group, a cycloalkyl group, a cycloalkyl-lower alkyl group or a phenyl group), a group represented by formula (3), $R^{13}R^{14}N$—C(=$X^1$)— (wherein $X^1$ represents an oxygen atom or a sulfur atom; $R^{13}$ represents a lower alkoxycarbonyl group, a cycloalkyl group, a lower alkynyl group, a 1-adamamtyl group, a pyrrolidino group, a piperidino group, a perhydroazepine-1-yl group, a perhydroazocine-1-yl group, a perhydroazonine-1-yl, a group represented by $Ar^2$—$(CH_2)_q$— [wherein $Ar^2$ represents a phenyl group (a hydrogen atom or each of two hydrogen atoms on the benzene ring may be substituted by a halogen atom, a lower alkyl group or a lower alkoxyl group), a furyl group or thienyl group, and q represents 0, 1 or 2]; $R^{14}$ represents a hydrogen atom, a hydroxyl group, a cycloalkyl group or a group represented by $Ar^3$—$(CH_2)_r$— (wherein $Ar^3$ represents a phenyl group, a furyl group or thienyl group, and r represents 1 or 2), $R^{13}$ and $R^{14}$ may form a 5- to 9-membered nitrogen-containing saturated heterocycle having 4 to 8 carbon atoms together with the adjacent nitrogen atom, one methylene group not adjacent to a nitrogen atom in a methylene group forming the heterocycle may be substituted by an oxy group, a thio group or —$NR^{15}$— (wherein $R^{15}$ represents a lower alkyl group), 1 to 4 hydrogen atoms on a carbon atom or carbon atoms of the heterocycle may each be substituted by hydroxyl groups or lower alkyl groups which may be substituted by hydroxyl groups, two adjacent carbon atoms of the heterocycle may form a double bond or a benzo condensed ring, and $R^{13}$ and $R^{14}$ may form a group represented by formula (LII) together with B:

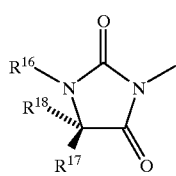
[LII]

wherein $R^{16}$ represents a hydrogen atom, a lower alkyl group or a cycloalkyl group, and $R^{17}$ and $R^{18}$ each represents hydrogen atoms or lower alkyl groups, independently;

B represents an oxygen atom or a group represented by —$NR^2$— (wherein $R^2$ represents a hydrogen atom or a methyl group), and forms the group represented by the above-mentioned forula (LII) together with $A^1$;

$R^3$ represents a lower alkyl group having 3 to 5 carbon atoms;

$R^4$ represents a hydrogen atom or a methyl group;

$R^5$ represents (1) a 3-indolylmethyl group, (2) a (2,3-dihydro-2-oxo-3-indolyl)methyl group, (3) a 3-indolylmethyl group in which the indole ring is substituted at the 1-position by a group represented by $R^{51}$—CO—$(CH_2)_s$— (wherein $R^{51}$ represents a hydrogen atom, a lower alkyl group, a hydroxyl group, a lower alkoxyl group, a benzyloxy group, an amino group or a mono-lower alkylamino group, s represents an integer of 0 to 6, and when s is 0, $R^{51}$ represents a group other than a hydroxyl group) or a group represented by $R52O)_2P(=O)$—$(CH_2)_t$— (wherein $R^{52}$ represents a hydrogen atom, a lower alkyl group or a benzyl group, and t represents an integer of 0 to 6), (4) a benzyl group in which any hydrogen atom on the benzene ring may be substituted by a group represented by $R^{53}$ O—CO—$(CH_2)_u$— (wherein $R^{53}$ represents a hydrogen atom or a lower alkyl group, and u represents an integer of 0 to 6), (5) a benzyl group in which one or two hydrogen atoms on the benzene ring are substituted by hydroxyl groups, or two hydrogen atoms on the benzene ring are substituted by a hydroxyl group and a sulfo group, (6) a 3-benzothienylmethyl group, a (1-oxo-3-benzo-thienyl)methyl group or (7) a (1,1-dioxo-3-benzothienyl)-methyl group;

$X^2$ represents an oxygen atom or a sulfur atom; and $A^2$ represents a group selected from the group consisting of groups represented by formulae (LIII), (LIV), (LV), (LVI) (LVII) and (LVIII):

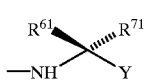
(LIII)

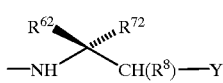
(LIV)

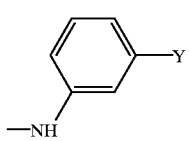
(LV)

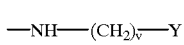
(LVI)

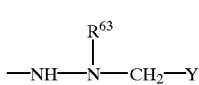
(LVII)

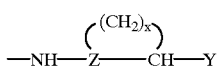
(LVIII)

wherein Y represents a sulfo group, a group represented by —$CO_2R^{91}$ (wherein $R^{91}$ represents a hydrogen atom, a lower alkyl group or a benzyl group) or a group represented by —$CONR^{92}R^{93}$ (wherein $R^{92}$ represents a hydrogen atom, a lower alkyl group, a lower alkylsulfonyl group, a phenylsulfonyl group in which 1 to 5 arbitrary hydrogen atoms on the benzene ring may each be substituted by lower alkyl groups or halogen atoms, or a carboxymethyl group, and $R^{93}$ represents a hydrogen atom or a lower alkyl group); $R^{61}$ represents a hydrogen atom or a lower alkyl group, or represents a methylene group together with $R^{71}$; $R^{71}$ represents a hydrogen atom, a lower alkyl group which may be substituted by a hydroxyl group, a phenyl group, a thienyl group, a phenyl-lower alkyl group in which any hydrogen atom on the benzene ring may be substituted by a hydroxyl group or a benzyloxy group, a thienyl-lower alkyl group, a thiazolyl-lower alkyl group, a 4-imidazolylmethyl group, a (lower alkyl-substituted 4-imidazolyl)methylthiomethyl group, a 3-indolylmethyl group, a carbamoyl-lower alkyl group or an N-benzyloxycarbonyl-ω-amino-lower straight chain alkyl group, or represents a methylene group together with $R^{61}$, with the proviso that when $R^{61}$ is a lower alkyl group, $R^{71}$ represents a group other than a hydrogen atom; $R^{62}$ represents a hydrogen atom, a phenyl group, a benzyl group, a carboxyl group, a carbamoyl group or an N-phenylcarbamoyl group, or represents a single bond together with $R^8$; $R^{72}$ represents a hydrogen atom, a lower alkyl group, a phenyl group, a benzyl group, a 3-indolylmethyl group, a carbamoyl group or an N-phenylcarbamoyl group, with the proviso that when $R^{62}$ is a group other than a hydrogen atom, $R^{72}$ represents a hydrogen atom or a lower alkyl group; $R^8$ represents a hydrogen atom, a lower alkyl group, a lower alkoxyl group or a hydroxyl group, or represents a single bond together with $R^{62}$; V represents 3, 4 or 5; $R^{63}$ represents a hydrogen atom, a lower alkyl group, a carboxy-lower alkyl group or a group represented by $Ar^4$—$(CH_2)_w$— (wherein $Ar^4$ represents a phenyl group, a furyl group or a thienyl group, and w represents 1 or 2; Z represents CH or N; and X represents 1, 2 or 3.

Specifically, peptide derivatives or pharmaceutically acceptable salts thereof shown in Examples of EP-A-460,679 are used.

[WO92/20706]

Compounds represented by formula [M] or pharmaceutically acceptable salts thereof:

$$AA^1\text{-}AA^2\text{-}AA^3\text{-}AA^4\text{-}AA^5\text{-}AA^6 \quad [M]$$

wherein $AA^1$ represents D-Dip, D-Bip, D-His, D-His(Dnp), D-2-Nal, D-1-Nal, D-Phe, D-Pgl, D-Tyr, D-Tyr(OMe), D-Tyr(OEt), D-Tyr(OtBu), D-Trp, D-Trp(For), D-Tic, D-Tza, D-Pyr, Ac-D-Dip, Ac-D-Bip, Ac-D-His, Ac-D-His (Dnp), Ac-D-2-Nal, Ac-D-1-Nal, Ac-D-Phe, Ac-D-Pgl, Ac-D-Tyr, Ac-D-Tyr(OMe), Ac-D-Tyr(OEt), Ac-D-Tyr (OtBu), Ac-D-Trp, Ac-D-Trp(For), Ac-D-Tic, Ac-D-Tza, Ac-D-Pyr, Ada-D-Dip, Ada-D-Bip, Ada-D-His, Ada-D-His (Dnp), Ada-D-2-Nal, Ada-D-1-Nal, Ada-D-Phe, Ada-D-Phe, Ada-D-Pgl, Ada-D-Tyr, Ada-D-Tyr(OMe), Ada-D-Tyr (OEt), Ada-D-Tyr(OtBu), Ada-D-Trp, Ada-D-Trp(For), Ada-D-Tic, Ada-D-Tza, Ada-D-Pyr, Adoc-D-Dip, Adoc-D-Bip, Adoc-D-His, Adoc-D-His(Dnp), Adoc-D-2-Nal, Adoc-D-1-Nal, Adoc-D-Phe, Adoc-D-Pgl, Adoc-D-Tyr, Adoc-D-Tyr(OMe), Adoc-D-Tyr(OEt), Adoc-D-Tyr(OtBu), Adoc-D-Trp, Adoc-D-Trp(For), Adoc-D-Tic, Adoc-D-Tza, Adoc-D-Pyr, Boc-D-Dip, Boc-D-Bip, Boc-D-His, Boc-D-His(Dnp), Boc-D-2-Nal, Boc-D-1-Nal, Boc-D-Phe, Boc-D-Pgl, Boc-D-Tyr, Boc-D-Tyr(OMe), Boc-D-Tyr(OEt), Boc-D-Tyr (OtBu), Boc-D-Trp, Boc-D-Trp(For), Boc-D-Tic, Boc-D-Tza, Boc-D-Pyr, Z-D-Dip, Z-D-Bip, Z-D-His, Z-D-His (Dnp), Z-D-2-Nal, Z-D-1-Nal, Z-D-Phe, Z-D-Pgl, Z-D-Tyr, Z-D-Tyr(OMe), Z-D-Tyr(OEt), Z-D-Tyr(OtBu), Z-D-Trp, Z-D-Trp(For), Z-D-Tic, Z-D-Tza, Z-D-Pyr, Fmoc-D-Dip, Fmoc-D-Bip, Fmoc-D-His, Fmoc-D-His(Dnp), Fmoc-D-2-Nal, Fmoc-D-1-Nal, Fmoc-D-Phe, Fmoc-D-Pgl, Fmoc-D-Tyr, Fmoc-D-Tyr(OMe), Fmoc-D-Tyr(OEt), Fmoc-D-Tyr (OtBu), Fmoc-D-Trp, Fmoc-D-Trp(For), Fmoc-D-Tic, Fmoc-D-Tza or Fmoc-D-Pyr;

$AA^2$ represents Ala, Alg, Arg, Asn, Asp, Dab, Glu, Gln, Gly, homoArg, homoGlu, homoLys, Ile, Leu, D-Leu, Lys, Met, Met(O), Met($O_2$), Nva, Nle, Orn, Phe, Tyr or Val, or $AA^2$ is lacking;

$AA^3$ represents Ans, D-Ans, N-MeAns, Glu, Gln, homophe, Phe or Tyr, or $AA^3$ is lacking;

$AA^4$ represents Ala, Chx, Gly, Glu, Ile, D-Ile, Leu, Nle, Nva or Val, or $AA^4$ is lacking;

$AA^5$ represents Ala, Chx, Gly, Ile, D-Ile, Leu, Nle, Nva or Val, or $AA^5$ is lacking; and $AA^6$ represents 2-Nal, 1-Nal, Pyr, Trp, Tyr(OMe), Tyr (OEt), Tyr(OtBu), Tyr, Trp-Gly, Trp-Asp, Trp(For), Dip, Phe, Bza or

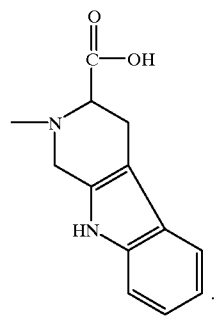

Specifically, compounds or pharmaceutically acceptable salts thereof shown in Examples of WO92/20706 are used.

[WO 93/08799]

Compounds represented by formula [N] or pharmaceutically acceptable salts thereof:

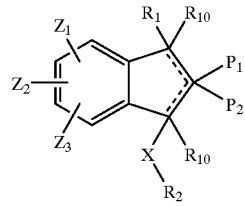

[N]

wherein:

$R_1$ is —$X(CH_2)_n Ar$ or —$X(CH_2)_n R_8$ or

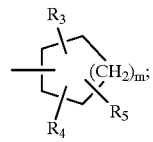

(c)

$R_2$ is hydrogen, Ar or (c);

$P_1$ is —$X(CH_2)_n R_8$;

$P_2$ is —$X(CH_2)_n R_8$, or —$XR_9 Y$;

$R_3$ and $R_5$ are independently hydrogen, $R_{11}$, OH, $C_{1-8}$alkoxy, $S(O)_q R_{11}$, $N(R_6)_2$, Br, F, I, Cl, $CF_3$, NHCOR$_6$, —$XR_9$—Y or —$X(CH_2)nR_8$ wherein the methylene groups of —$X(CH_2)_n R_8$ may be unsubstituted or substituted by one or more —$(CH_2)_n Ar$ groups;

$R_4$ is hydrogen, $R_{11}$, OH, $C_{1-5}$alkoxy, $S(O)_q R_{11}$, $NR6)_2$, —$XR11$), Br, F, I, Cl or NHCOR$_6$ wherein the C$_{1-5}$alkoxy may be unsubstituted or substituted by OH, methoxy or halogen;

R$_6$ is independently hydrogen or C$_{1-4}$alkyl;

R$_7$ is independently hydrogen or C$_{1-6}$alkyl or (CH$_2$)$_n$Ar;

R$_8$ is hydrogen, R$^1$, COOH, PO$_3$H$_2$, P(O)(OH)R$_7$ or tetrazole;

R$_9$ is C$_{1-10}$alkyl, C$_{2-10}$alkenyl or phenyl all of which may be unsubstituted or substituted by one or more OH, N(R$_6$)$_2$, COOH, halogen or XC$_{1-5}$alkyl;

R$_{10}$ is R$_3$ or R$_4$;

R$^{11}$ is C$_{1-8}$alkyl, C$_{2-8}$alkenyl, C$_{2-8}$alkynyl all of which may be unsubstituted or substituted by one or more OH, CH$_2$OH, N(R$_6$)$_2$ or halogen;

X is (CH$_2$)$_n$, O, NR$_6$ or S(O)$_q$;

Y is CH$_3$ or —CH$_2$X(CH$_2$)$_n$Ar;

Ar is:

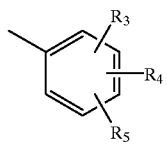

(a)

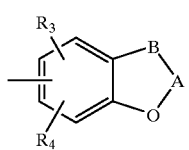

(b)

naphthyl, indolyl, pyridyl or thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more R$_3$ or R$_4$ groups;

A is C=O, or [CR$_6$)$_2$]$_m$;

B is —CH$_2$— or —O—;

Z$_1$ and Z$_2$ are independently hydrogen, C$_{1-8}$alkyl, C$_{2-8}$alkenyl, C$_{2-8}$alkynyl, OH, C$_{1-8}$alkoxy, S(O)$_q$ C$_{1-8}$alkyl, N(R$_6$)$_2$, Br, F, I, Cl, CF$_3$, NHCOR$_6$, —X(CH$_2$)nR$_8$, phenyl, benzyl or C$_{3-6}$cycloalkyl wherein the C$_{1-8}$alkyl, C$_{2-8}$alkenyl, C$_{2-8}$alkynyl may be optionally substituted by COOH, OH, CO(CH$_2$)$_n$CH$_3$, CO(CH$_2$)$_n$CH$_2$N(R$_6$)$_2$ or halogen; or Z$_1$ and Z$_2$ together may be —O—A—O— on contiguous carbons;

Z$_3$ is Z$_1$ or XR$_9$Y;

q is zero, one or two;

n is an integer from 0 to six;

m is 1, 2 or 3;

and the dotted line indicates the optional presence of a double bond; or a pharmaceutically acceptable salt thereof; provided that R$_2$ is not hydrogen when X is S(O)$_q$;

when the optional double bond is present there is only one R$_{10}$ and there is no P$_1$;

the compound Formula I is not (1RS)-1,3-diphenylylindene-2-carboxylic acid; (cis,cis)-(IRS, 3SR)-1,3-diphenylidindane-2-carboxylic acid; (1RS)-3-[3-Methyl-1-pheyl-(1H)-ind-2-en-1-yl] propionic acid; or (1RS)-2-[1,3-dipheyl-(1H)-ind-2-en-2-yl]ethanoic acid.

[WO 93/13218]

Peptides represented by formula [O] or pharmaceutically acceptable salts thereof:

AA$^1$-AA$^2$-AA$^3$-AA$^4$-AA$^5$-AA$^6$        [O]

wherein AA$^1$ is

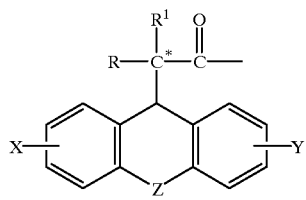

wherein R is hydrogen, alkyl, palkenyl, alkynyl, cycloalkyl, cycloalkylalkyl, aryl, heteroaryl, fluorenylmethyl,

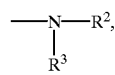

wherein R$^2$ and R$^3$ are each the same or different and each is hydrogen, alkyl, alkenyl, alkynyl, cycloalkyl, cycloalkylalkyl, aryl, arylalkyl, heteroaryl, or fluorenylmethyl,

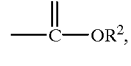

wherein R$^2$ is as defined above,

—OR$^2$, wherein R$^2$ is as defined above,

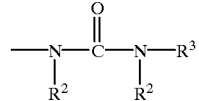

wherein R² and R³ are as defined above,

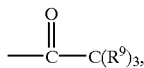

wherein R⁹ is F, Cl, Br, or I,
—CH₂—OR², wherein R² is as defined above,

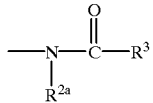

R²ᵃ wherein R²ᵃ is hydrogen or alkyl and R³ is defined above,

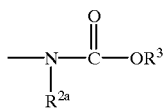

wherein R²ᵃ and R³ are as defined above excluding R³ is hydrogen, or

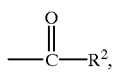

wherein R² is defined above,
R¹ is hydrogen or alkyl,
Z is —O—,
—S(O)$_m$—, wherein m is zero or an integer of 1 or 2,

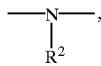

wherein R² is as defined above,
—(CH₂)$_n$—, wherein n is zero or an integer of 1, 2, 3, or 4,
—(CH₂)$_n$—CH=CH—(CH₂)$_n$—, wherein n is as defined above, —CO—,

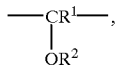

wherein R¹ and R² are as defined above, or

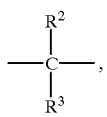

wherein R² and R³ are each the same or different and each is as defined above,
X and Y are the same and substituted at the same position on the aromatic ring and each may be one, two, three, or four substituents selected from the group consisting of
hydrogen,
halogen,
alkyl,
—CO₂R², wherein R² is as defined above,

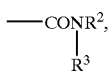

wherein R² and R³ are as defined above,

wherein R² and R³ are as defined above, nitro or

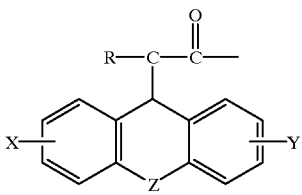

wherein R, Z, X, and Y are as defined above;
AA² is

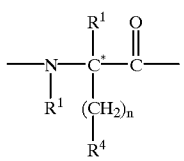

wherein R⁴ is
hydrogen,
alkyl,
alkenyl,
alkynyl,
cycloalkyl,
aryl,
heteroaryl,

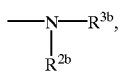

wherein R²ᵇ and R³ᵇ are each the same or different and each is
hydrogen,
alkyl,
cycloalkyl,
aryl, or
heteroaryl,
—OR²ᵇ, wherein R²ᵇ is as defined above,

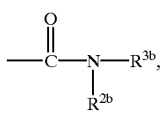

wherein R²ᵇ and R³ᵇ are each the same or different and each is as defined above for ²ᵇ and R³ᵇ,

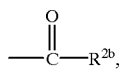

wherein $R^{2b}$ is as defined above,

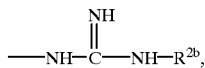

wherein $R^{2b}$ is as defined above, or

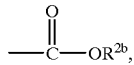

wherein $R^{2b}$ is as defined above, and $R^1$ and n are as defined above, $AA^2$ can be absent;

$AA^3$ is

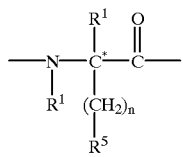

wherein $R^5$ is
hydrogen,
alkyl,
aryl,
heteroaryl,

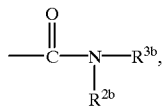

wherein $R^{2b}$ and $R^{3b}$ are each the same or different and each is as defined above,

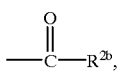

wherein $R^{2b}$ is as defined above, or

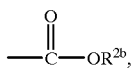

wherein $R^{2b}$ is as defined above, and $R^1$ and n are as defined above, $AA^3$ can be absent;

$AA^4$ and $AA^5$ are each independently absent or each is independently

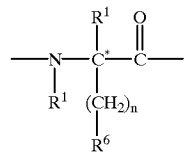

wherein $R^6$ is
hydrogen,
alkyl,
alkenyl,
alkynyl,
cycloalkyl,
aryl, or
heteroaryl, and
$R^1$ and n are as defined above, $AA^6$ is

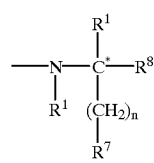

wherein $R^7$ is
aryl or
heteroaryl, $R^8$ is

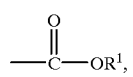

wherein $R^1$ is as defined above,
—$OR^1$, wherein $R^1$ is as defined above,

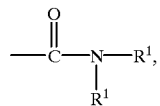

wherein $R^1$ is as defined above, or
—$CH_2$—$OR^1$, wherein $R^1$ is as defined above, and $R^1$ and n are as defined above;

wherein the stereochemistry at C* in $AA^1$, $AA^2$, $AA^3$, $AA^4$, or $AA^5$ is D, L, or DL and the stereochemistry at C* in $AA^6$ is L; or a pharmaceutically acceptable salt thereof.

[WO 93/21219]

Peptides represented by formula [P] or a pharmaceutically acceptable salt thereof:

X-A-Trp-B-Gly-Thr-E-G-Y  (P)

wherein A represents Asn or Asp; B represents His or Lys; E represents Ala or Ser; G represents Ala or Pro; X represents $X^1$-Gly or

Y represents hydroxyl, lower alkoxyl, amino,

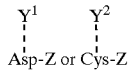

[wherein X and $X^3$ each represent hydrogen, benzyloxycarbonyl, t-butyloxycarbonyl, 9-fluorenylmethyloxycarbonyl, or carbonyl-substituted or unsubstituted lower alkanoyl; $X^2$ and $Y^2$ each represent hydrogen; $Y^1$ represents hydroxyl, lower alkoxyl or amino, or $X^1$ and $Y^1$, and $X^2$ and $Y^2$ each combine to form $X^1$-$Y^1$ and $X^2$-$Y^2$, respectively, which represent single bonds; Z represents hydroxyl, lower alkoxyl, benzyloxy or benzhydryloxy, Gly-$Z^1$ (wherein $Z^1$ represents hydroxyl, lower alkoxyl, benzyloxy or benzhydryloxy, or forms $X^1$-$Z^1$ together with $X^1$, which represents a single bond), Ala-$Z^1$ (wherein $Z^1$ has the same meaning as given above), Val-$Z^1$ (wherein $Z^1$ has the same meaning as given above), Trp-$Z^1$ (wherein $Z^1$ has the same meaning as given above), Trp-Gly-$Z^1$ (wherein $Z^1$ has the same meaning as given above), Trp-Asn-Tyr-Tyr-Trp-$Z^1$ (wherein $Z^1$ has the same meaning as given above), Trp-Phe-Phe-Asn-Tyr-Tyr-7Hyt-$Z^1$ (wherein $Z^1$ has the same meaning as given above, and 7Hyt represents 7-hydroxytryptophan), Trp-Ile-Ile-Trp-$Z^1$ (wherein $Z^1$ has the same meaning as given above), Trp-Val-Tyr-Phe-W-His-Leu-Asp-Ile-Ile-Trp-$Z^1$ (wherein $Z^1$ has the same meaning as given above; and W represents Ala, Ser or Cys), Trp-W-His-Leu-Asp-Ile-Ile-Trp-$Z^1$ (wherein $Z^1$ and W have the same meanings as given above), Trp-Val-Tyr-Tyr-W-His-Leu-Asp-Ile-Ile-Trp-$Z^1$ (wherein $Z^1$ and W have the same meanings as given above), Trp-Leu-Tyr-Phe-W-His-Gln-Asp-Val-Ile-Trp-$Z^1$ (wherein $Z^1$ and W have the same meanings as given above), Trp-Val-Tyr-Phe-W-Phe-Phe-Asn-Tyr-Tyr-Trp-$Z^1$ (wherein $Z^1$ and W have the same meanings as given above), Trp-Phe-Phe-Asn-Tyr-Tyr-W-His-Leu-Asp-Ile-Ile-Trp-$Z^1$ (wherein $Z^1$ and W have the same meanings as given above), Trp-Phe-Phe-Asn-Tyr-Tyr-Asn-Ile-Ile-Trp-$Z^1$ (wherein $Z^1$ has the same meaning as given above), or J-Phe-M-Q-Tyr-R-T-$Z^1$ (wherein J represents Trp or a single bond; M represents Phe a single bond; Q represents Asn or a single bond; R represents Tyr or a single bond; T represents Trp, Ala, Phe, Tyr, Trp-Trp, Asn-Tyr-Tyr-Trp, Trp-Asn-Tyr-Tyr-Trp, Trp-Val-Tyr-Phe-W-His-Leu-Asp-Ile-Ile-Trp (wherein W has the same meaning as given above) or a single bond; at least two or more of J, M, Q, R and T do not concurrently form a single bond; and $Z^1$ has the same meaning as given above].
[EP-A-555,537]

Peptides represented by formula [Q] or pharmaceutically acceptable salts thereof:

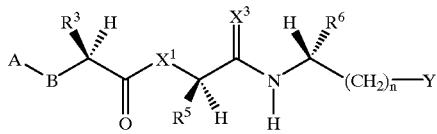

[Q]

wherein A is a group of the formula $R^{11}$OCO-(wherein $R^{11}$ is a lower alkyl group or a phenyl group), or a group of the formula $R^{12}R^{13}$N—C(=O)-(wherein $R^{12}$ is a lower alkyl group, a cycloalkyl group, a 1-adamantyl group, a phenyl group wherein one or two optional hydrogen atoms on the benzene ring may independently be replaced by a halogen atom, a trifluoromethyl group, a nitro group, an amino group or a formylamino group, a pyridyl group, or a thienyl group, $R^{13}$ is a hydrogen atom, a lower alkyl group or a cycloalkyl group, or $R^{12}$ and $R^{13}$ form, together with the adjacent nitrogen atom, a 5- to 9-membered nitrogen-containing saturated heterocyclic ring having 4 to 8 carbon atoms, wherein among methylene groups forming the ring, one optional methylene group not adjacent to the above nitrogen atom may be replaced by a thio group, and one to four optional hydrogen atoms on the carbon atoms of the heterocyclic ring may independently be replaced by a lower alkyl group, and further two adjacent carbon atoms in the heterocyclic ring may form a benzo-fused ring); B is an oxygen atom or a group of the formula —$NR^2$— (wherein $R^2$ is a hydrogen atom or a lower alkyl group); $R^3$ is a lower alkyl group, a cycloalkyl group, an anyl group, a heterocyclic group, a cycloalkyl lower alkyl group, an aryl lower alkyl group or a heterocyclic lower alkyl group; $X^1$ is an oxygen atom or a group of the formula —$NR^4$— (wherein $R^4$ is a hydrogen atom or a lower alkyl group); $R^5$ is a 3-indolylmenthyl, 3-benzothienylmethyl, 1-naphthylmethyl or benzyl group wherein one or two optional hydrogen atoms on the ring may be replaced by a hydroxyl group, a halogen atom, a formyl group, a lower alkyl group, a lower alkoxy group, a lower alkylthio group, a lower alkylsulfinyl group, a lower alkylsulfonyl group, a lower alkoxycarbonyl group, a nitro group or a group of the formula $R^{51}$—CO—$X^2$ (wherein $R^{51}$ is a lower alkyl group, a lower alkoxy group, or an amino group which may be substituted by a lower alkyl group, and $X^2$ is an oxygen atom or a group of the formula —$NR^{52}$— (wherein $R^{52}$ is a hydrogen atom or a lower alkyl group)); $X^3$ is an oxygen atom or a sulfur atom; $R^6$ is a hydrogen atom, or a lower alkyl or lower alkenyl group which may have a substituent selected from the group consisting of a hydroxyl group, a lower alkoxy group, a lower alkylthio group and a heterocyclic group; n is 0 or 1; Y is a hydroxymethyl group, a group of the formula $CO_2R^{71}$ (wherein $R^{71}$ is a hydrogen atom or a lower alkyl group), a group of the formula $CONHR^{72}$ (wherein $R^{72}$ is a hydrogen atom or a lower alkyl group which may have a substituent selected from the group consisting of a hydroxyl group, a carboxyl group and a sulfo group), a 1H-tetrazol-5-yl group, a sulfo group and a phosphono group; or a pharmaceutically acceptable salt thereof.
[Japanese Patent Unexamined Publication 5-178890]

Compounds represented by formula [R] or a pharmaceutically acceptable salt thereof:

[R]

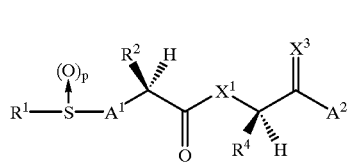

wherein $R^1$ is a lower alkyl group, a cycloalkyl group, a cycloalkyl lower alkyl group, an aralkyl group, an aryl group, a 5- to 10-membered heterocyclic ring, a 5- to 10-membered heterocyclic lower alkyl group, in which on the chain and/or the ring, the lower alkyl group, the cycloalkyl group, the cycloalkyl lower alkyl group, the aralkyl group, the aryl group, the 5- to 10-membered heterocyclic ring, the 5- to 10-membered heterocyclic lower alkyl group may be each independently substituted by a lower aklyl, halogen, OH, a lower alkoxy, nitro, trifluoromethyl, cyano, formyl, a lower alkanoyl, carboxyl, a lower alkoxy carbonyl group, amino, monoloweralkylamino, diloweralkylamino, formylamino, alkanoylamino, aroylamino, carbamoyl, N-mono-loweralkylcarbamoyl or N,N-diloweralkylcarbamoyl, mercapto, loweralkylthio or loweraklanoylthio;

p is an integer of 0 to 2;

$A^1$ is a single bond or a divalent lower alkylene group which may be substituted with a lower alkyl;

$R^2$ is a lower alkyl group, a cycloalkyl group, a cycloalkyl lower alkyl group, an aralkyl group, an aryl group, a 5- to 10-membered heterocyclic ring, a 5- to 10-membered heterocyclic lower alkyl group;

$X^1$ is an oxygen atom or —$NR^3$— wherein $R^3$ is hydrogen or a lower alkyl group;

$R^4$ is a 5- to 10-membered heterocyclic lower alkyl group which may have on the ring a lower alkyl group; $R^{41}$—CO—$(CH_2)_q$ wherein $R^{41}$ represents hydrogen, a lower alkyl group, OH, a lower alkoxy group, aralkyloxy, amino, a monolower alkylamino group or a dilower alkylamino group; q is an integer of 0 to 6; an aryl lower aklyl group which may have on the ring nitro, $R^{42}CO$—$(CH_2)_r$— wherein $R^{42}$ represents a lower alkyl group, a lower alkoxy group, amino, a mono lower alkylamino group or a dilower alkylamino group; r is an integer of 0 to 6; $R^{42}$—CO—$X^2$— wherein $R^{42}$ has the same meaning as above, $X^2$ is an oxygen atom or —$NR^{43}$— wherein $R^{43}$ is hydrogen or a lower alkyl group; or $R^{44}O$—$(CH_2)_s$— wherein $R^{44}$ is hydrogen or a lower alkyl group and s is an integer of 0 to 6;

$X^3$ represents an oxygen or sulfur atom;

$A^2$ represents any group selected from a group consisting of the following [RII] to [RVII]:

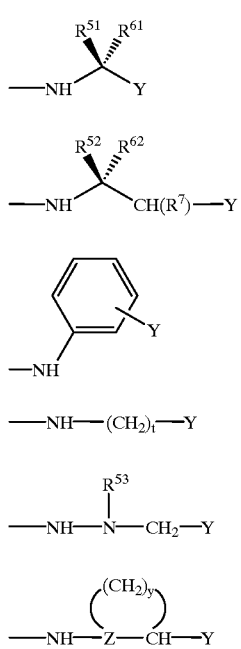

wherein Y represents a hydroxy loweralkyl group, a sulfo group, a phosphono group, —$CO_2R^{81}$ wherein $R^{81}$ is hydrogen or a carboxyl protective group, or —$CONR^{82}R^{83}$ wherein $R^{82}$ and $R^{83}$ each independently represents hydrogen, a lower alkyl group, a lower alkyl sulfonyl group, a phenyl sulfonyl group in which 1 to 5 hydrogen atoms on the benzene ring may be independently substituted by a lower alkyl group or halogen, or a carboxy lower alkyl group;

$R^{51}$ is hydrogen or a lower alkyl group, or forms a methylene group together with $R^{61}$ described below;

$R^{53}$, $R^{61}$ and $R^{62}$ each independently represents a lower alkyl group, a lower alkenyl group, an aryl group, an aryl lower alkyl group, a 5- to 10-membered heterocyclic ring, a 5- to 10-membered heterocyclic lower alkyl group; in which, on the chain and/or the ring, the lower alkyl group, the lower alkenyl group, the aryl group, the aryl lower alkyl group, the 5- to 10-membered heterocyclic ring, the 5- to 10-membered heterocyclic lower alkyl group may be each independently substituted by OH, a lower aklyl group, halogen, a lower alkoxy group, an aryloxy group, an acyloxy group, a carboxyl group, a protected carboxyl group, an amino group, a monoalkylamino group, a diloweralkylamino group, a carbamoyl group, an N-mono-loweralkylcarbamoyl group, an N,N-diloweralkylcarbamoyl group, a lower-alkoxy carbonylamino group or an aryloxy carbonylamino group; further $R^{61}$ and $R^{51}$ may form together a methylene group in the proviso that $R^{61}$ is other than hydrogen when $R^{11}$ is a lower alkyl, and $R^{62}$ is hydrogen or a lower alkyl group when $R^{52}$ is other than hydrogen;

$R^{52}$ represents hydrogen, an aryl group, an aralkyl group, a carboxyl group, a carbamoyl group, an N-monoloweralkyl carbamoyl group, an N,N-diloweralkyl carbamoyl group or an N-arylcarbamoyl group; or forms a single bond with $R^7$;

$R^7$ represents hrdrogen, a lower alkyl group, a lower alkoxy group or OH, or forms a single bond with $R^{52}$;

t is an integer of 2 to 6;

Z is CH or N;

v is an integer of 1 to 3.

Especially the compound is represented by the formula is preferable:

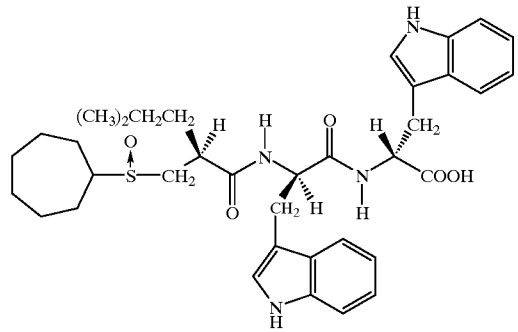

[Japanese Patent Unexamined Publication 5-279390]

Cyclic pentapeptides represented by formula [S] or pharmaceutically acceptable salts thereof:

cyclo(-Dtrp(COOCH₃)-Dasp-Pro-DtertLeu-γMeLeu-)  [S].

[EP-A-558,258]

Compounds represented by formula [T] or pharmaceutically acceptable salts thereof:

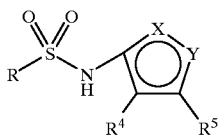
[T]

wherein one of X and Y is N and the other is O; R is naphthyl or naphthyl substituted with $R^1$, $R^2$ and $R^3$; $R^1$, $R^2$ and $R^3$ are each independently hydrogen; alkyl, alkenyl, alkynyl, alkoxy, cycloalkyl, cycloalkylalkyl, cycloalkenyl, cycloalkenylalkyl, aryl or aralkyl, any of which may be substituted with $Z^1$, $Z^2$ and $Z^3$; halo; hydroxyl; cyano; nitro; —C(O)H; —C(O)$R^6$; COOH; COO$R^6$; —SH; —S(O)n$R^6$; —S(O)m—OH; —S(O)m—O$R^6$; —O—S(O)m—$R^6$; —O—S(O)m—OH; —S(O)m—O$R^6$; —$Z^4$—N$R^7R^8$; or —$Z^4$—NR11)—$Z^5$—N$R^9R^{10}$;

- $R^4$ and $R^5$ are each independently hydrogen; alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ and $Z^3$; halo; hydroxyl; cyano; nitro; —C(O)H; —C(O)$R^6$; COOH; COO$R^6$; —SH; —S(O)n$R^6$; —S(O)m—OH; —S(O)m—O$R^6$; —O—S(O)m—$R^6$; —O—S(O)m—OH; —O——S(O)m—O$R^6$; —$Z^4$—N$R^7R^8$; or —$Z^4$—NR11)—$Z^5$—N$R^9R^{10}$; or $R^4$ and $R^5$ together are alkylene or alkenylene (either of which may be substituted with $Z^1$, $Z^2$ and $Z^3$), completing a 4- to 8-membered saturated, unsaturated or aromatic ring together with the carbon atoms to which they are attached;
- $R^6$ is alkyl, alkenyl, alkynyl, alkoxy, cycloalkyl, cycloalkylalkyl, cycloalkenyl, cycloalkenylalkyl, aryl, or aralkyl, any of which may be substituted with $Z^1$, $Z^2$ or $Z^3$;
- $R^7$ is as defined for $R^6$ or is H, CN, OH, COH, CO$R^6$, CO$_2R^6$; or in Z is not SO$_n$, $R^7$ can be SH, CO$R^6$, SO$_m$OH, SO$_m$O$R^6$, OSO$_m$$R^6$, OSO$_m$OH or OSO$_m$O$R^6$;
- $R^8$ is as defined for $R^6$ or H or if $Z^4$ is not CO and $R^7$ is not COH, CO$R^6$ or CO$_2R^6$, $R^8$ can be COH or CO$R^6$; or N$R^7R^8$ is alkylene or alkenylene (each opt. substituted with $Z^1$, $Z^2$ or $Z^3$) completing a 3–8 membered optionally saturated, unsaturated, or aromatic ring;
- $R^9$ is as defined for $R^6$ or H, OH, COH or CO$R^6$, CO$_2R^6$, SH, SO$_nR^6$, SO$_m$OH, SO$_m$O$R^6$, OSO$_m$$R^6$, OSO$_m$OH or OSO$_m$O$R^6$;
- $R^{10}$ is as defined for $R^6$ or H or if $Z^5$ is not CO and $R^9$ is not COH, CO$R^6$ or CO$_2R^6$, $R^{10}$ can be COH or CO$R^6$;
- $R^{11}$ is as defined for $R^6$ or H, OH, COH, CO$R^6$ or CO$_2R^6$; or
- any 2 of $R^9$, $R^{10}$ and $R^{11}$ together form alkylene or alkenylene (each opt. substituted with $Z^1$, $Z^2$ or $Z^3$) completing a 3–8 membered optionally saturated, unsaturated, or aromatic ring, with the atoms to which they are attached;
- $Z^1$, $Z^2$ and $Z^3$ are H, halogen, OH, alkyl, alkenyl, aralkyl, alkoxy, aryloxy, aralkyloxy, SH, SO$_nZ^6$, SO$_m$OH, SO$_m$O$Z^6$, OSO$_m$OH, OSO$_m$O$Z^6$, oxo, NO$_2$, CN, COH, CO$Z^6$, CO$_2$H, CO$_2Z^6$, $Z^4$N$Z^7Z^8$, $Z^4$N$Z^{11}Z^5Z^6$, $Z^4$N$Z^{11}Z^5$N$Z^7Z^8$;
- $Z^4$, $Z^5$ are a vinyl bond, $Z^9$SOn$Z^{10}$, $Z^9$CO$Z^{10}$, $Z^9$CS$Z^{10}$, $Z^9$ O$Z^{10}$, $Z^9$S$Z^{10}$ or $Z^9$OCO$Z^{10}$;
- $Z^6$, $Z^7$, $Z^8$ are H, alkyl, alkenyl, alkynyl, cycloalkyl, cycloalkylalkyl, cycloalkenyl, cycloalkenylalkyl, aryl, aralkyl; or
- N$Z^7Z^8$ is alkylene or alkenylene completing a 3–8 membered optionally saturated, unsaturated, or aromatic ring;
- $Z^9$, $Z^{10}$ are a single bond, alkylene, alkenylene or alkynylene;
- $Z^{11}$ is as defined for $R^6$ or H, OH, COH, CO$Z^6$ or CO$_2Z^6$; or
- any 2 of $Z^7$, $Z^8$ and $Z^{11}$ together form alkylene or alkenylene completing a 3–8 membered optionally saturated, unsaturated, or aromatic ring, with the atoms to which they are attached;
- m is 1 or 2,
- n is 0, 1 or 2.

Especially the following compound is preferable:

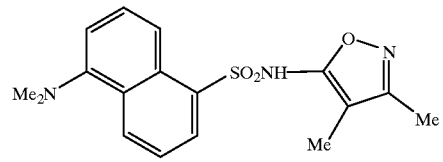

[WO 93/23404]

Compounds represented by formula [U] or pharmaceutically acceptable salts thereof:

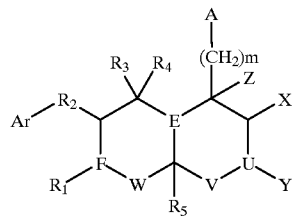

[U]

wherein Ar is a substituted or unsubstituted aromatic or heterocyclic group; R is H or a substituted or unsubstituted straight or branched chain, cyclic or mixture of straight, branched and cyclic alkyl, alkenyl, alkynyl, aryl, arylalkyl, alkoxyalkyl or alkoxycarbonyl group having from 1–20 carbon atoms; A is a functional group that bears a polar moiety, and is preferably COOH or RNH; $R_1$ is R, R—C=O, R substituted with one or more heteroatoms, a substituted or unsubstituted aryl group, or is aryl-(CH$_2$)$_n$; $R_2$ is (CH$_2$)$_n$, CHR, C(R)$_2$, COO, OCO, NHCO, CONH, SO, SO$_2$ or NR; $R_3$ and $R_4$, which are the same or different or each may be absent, and are =O, H, O-aryl, OR, O-alkyl or alkyl, aryl, SR, S-aryl, NHR, NH-aryl, NR, or are other heteroaromatic groups; $R_5$ is H, OH or R; E and F, which are the same or are different, are either N or (CH$_2$)$_p$; p is an integer or 0 between 0 and 5; m and n are integers or 0 between 0 and 10; T is O, S, NCOR or NR; U and V, which may be the same or different, are (CH$_2$)n; W is CO, (CH$_2$)$_n$, (CH$_2$)$_n$—CHR or CHR—(CH$_2$)$_n$; X and Y, which may be the same or different, are H, alkyl or aryl or X and Y form a saturated or unsaturated homocyclic or heterocyclic ring containing 3–15 members; and Z is H, SR, NHR or N(R)$_2$.

Especially the compound represented by the following formula is preferable:

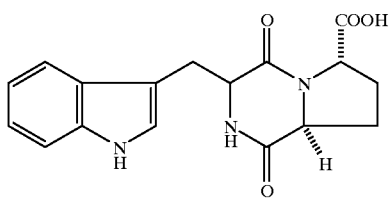

[EP-A-569193]

Compounds represented by formula [V] or pharmaceutically acceptable salts thereof:

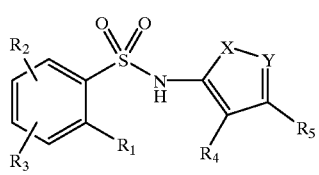

[V]

One of X, Y is N and the other is O;

$R_1$, $R_2$, $R_3$=independently H ($R_1$ is not H); alkyl, alkenyl, alkynyl, alkoxy, cycloalkyl(alkyl), cycloalkenyl(alkyl), aryl, aryloxy, aralkyl or aralkoxy; halo, hydroxyl; cyano; nitro; —C(O)H; —C(O)$R_6$; COOH; COO$R_6$; —SH; —S(O)$_n R_6$; —S(O)$_m$—OH; —S(O)$_m$—O$R_6$; —O—S(O)$_m$—$R_6$; —O—S(O)$_m$—OH; —O—S(O)$_m$—O$R_6$; —$Z_4$—N$R_7 R_8$; or —$Z_4$—N($R_{11}$)—$Z_5$—N$R_9 R^{10}$;

$R_4$, $R_5$=as defined for $R_1$–$R_3$ or together form a 4–8 membered saturated, unsaturated or aromatic ring;

$R_6$ is alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$, $R_7$ is H; alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$; cyano; hydroxyl; —C(O)H; —C(O)$R_6$; COOH; COO$R_6$; —SH; —S(O)$_n R_6$; —S(O)$_m$—OH; —S(O)$_m$—O$R_6$; —O—S(O)$_m$—$R_6$; —O—S(O)$_m$—OH; —O—S(O)$_m$—O$R_6$ except when $Z_4$ is —S(O)$_n$—;

$R_8$ is H; —C(O)H or —C(O)$R_6$ except when $Z_4$ is —C(O)— and $R_7$ is —C(O)H, —C(O)$R^6$, COOH or COO$R_6$; alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$; or $R_7$ and $R_8$ together are alkylene or alkenylene (either of which may be substituted with $Z_1$, $Z_2$ and $Z_3$), completing a 3- to 8-membered saturated, unsaturated or aromatic ring together with the nitrogen atom to which they are attached;

$R_9$ is H; hydroxyl; —C(O)H or —C(O)$R_6$; COOH or COO$R_6$; —SH; —S(O)$_n R_6$; —S(O)$_m$—OH; —S(O)$_m$—O$R_6$; —O—S(O)$_m$—$R_6$; —O—S(O)$_m$—OH; —O—S(O)$_m$—O$R_6$; alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$;

$R_{10}$ is H; —C(O)H or —C(O)$R_6$ except when $Z_5$ is —C(O)— and $R_9$ is —C(O)H, —C(O)$R_6$, COOH or COO$R_6$; alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$;

$R^{11}$ is H; hydroxyl, —CO$_2 R_6$ or COOH, except when one of $R_9$ and $R_{10}$ is hydroxyl, —CO$_2 R_6$ or COOH; —C(O)H, —C(O)$R_6$; or alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$;

any 2 of $R_9$, $R_{10}$ and $R^{11}$ together form alkylene or alkenylene (each opt. substituted with $Z_1$, $Z_2$ and $Z_3$) completing a 3–8 membered optionally saturated, unsaturated, or aromatic ring, with the atoms to which they are attached;

$Z_1$, $Z_2$ and $Z_3$ are each independently H; halogen; OH; alkoxy, SH, SO$_n Z_6$, SO$_m$OH, SO$_m$O$Z_6$, OSO$_m Z_6$, OSO$_m$OH or OSO$_m$O$Z_6$; oxo; NO$_2$, CN, COH, COZ$_4$, CO$_2$H, CO$_2 Z_4$, NZ$_7 Z_8$, CONZ$_7 Z_8$ or S(O)$_n Z_7 Z_8$;

$Z_4$ and $Z_5$ are each independently a single bond; —S(O)$_n$; —C(O)—; —C(S)—; or alkyl, alkenyl, alkynyl, alkoxy, cycloalkyl, cycloalkylalkyl, cycloalkenyl, cylcoalkenylalkyl, aryl or aralkyl, any of which may be substituted with $Z_1$, $Z_2$ and $Z_3$;

$Z^6$, $Z_7$ and $Z_8$ are each independently hydrogen, alkyl, alkenyl, alkynyl, alkoxy, cycloalkyl, cycloalkylalkyl, cycloalkenyl, cylcoalkenylalkyl, aryl or aralkyl, or $Z_7$ and $Z_8$ together form alkylene or alkenylene completing a 3–8 membered saturated, unsaturated, or aromatic ring, with the nitrogen atom to which they are attached;

m is 1 or 2; and n is 0, 1, or 2.

Especially the compound represented by the following formula is preferable:

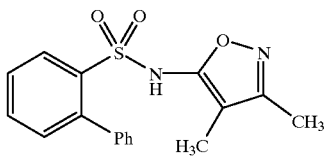

[WO 93/17701]

Cyclic pentapeptides represented by formula [W1], [W2] or [W3] or a pharmaceutically acceptable salt thereof:

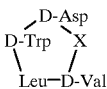

[W1]

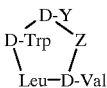

[W2]

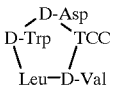

[W3]

X=an α-amino acid with a conformationally restricted 4–16C side chain.

Y=Ser, Z=an α-amino acid with a conformationally restricted side chain.

The side chain, C-amino and N-amino groups of X form 1–3 separate or fused rings with the amino groups being members of one the rings.

TCC is 1,2,3,4-tetrahydro-2-carboline-3-caroxylic acid.

[Bioorganic & Medicinal Chemistry Letters, Vol. 10, pp. 2099–2104 (1993)]

Compounds represented by formula [X1], [X2] or [X3] or a pharmaceutically acceptable salt thereof:

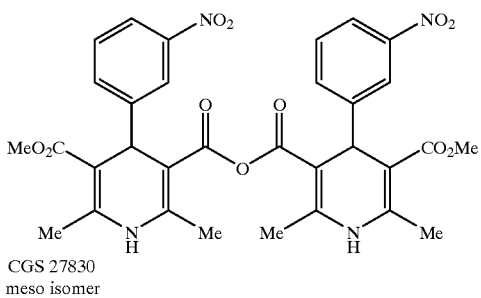

CGS 27830
meso isomer

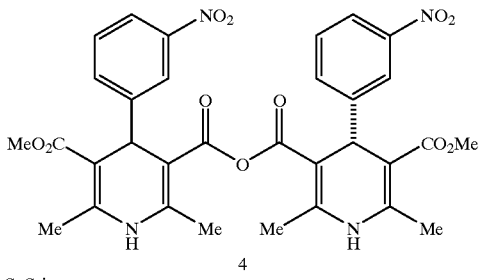

4
S, S-isomer

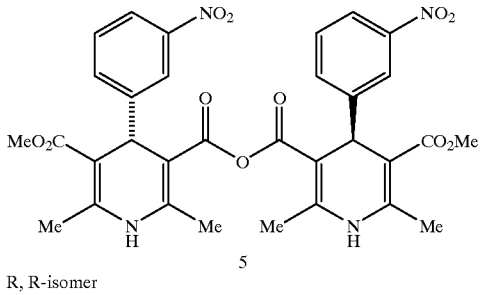

5
R, R-isomer

The compounds having antagonistic activity on endothelin receptors of the present invention can be used for prophylaxis and/or treatment of hypofunction of various organs which occurs during or after surgery or transplant, and for prophylaxis and/or treatment of complications hereof. Examples of the organs include the liver, the kidney, the heart, the spleen and the pancreas. For example, in liver surgery, a method is generally used at present in which the liver blood vessel is temporarily ligated and reperfused after completion of the surgery. However, the ligation of the blood vessel for a long period of time (5 to 10 minutes or more) is known to decrease liver function after reperfusion, resulting in hepatic insufficiency. Using a rat hepatic injury model after ischemia-reperfusion as a model of this, the effect of the compounds having antagonistic activity on endothelin receptors was studied. As a result, remarkable improvement of hepatic insufficiency was observed in the compounds. Accordingly, the compounds having antagonistic activity on endothelin receptors can be effectively used for prophylaxis and/or treatment of such hypofunction of the organs such as the liver which occurs in their surgery or transplant or after that, and for prophylaxis and/or treatment of complications thereof. The compounds having antagonistic activity on endothelin receptors used in the present invention are safe, low-toxic compounds.

Examples of hypofunction of the liver which occurs in its surgery or transplant or after that, or indexes thereof include, for example, an increase in transaminase (GPT-GOT) activity, a decrease in formation of fibrinogen or prothrombin and a decrease in production of heparin. The compounds having antagonistic activity on endothelin receptors have prophylactic and/or therapeutic effect on the hypofunction of the liver and the complications thereof.

When the compounds having antagonistic activity on endothelin receptors are used for prophylaxis and/or treatment of the hypofunction of organs which occurs in their surgery or transplant or after that, and for prophylaxis and/or treatment of the complications thereof, the compounds can be given orally or parenterally to warm-blooded animals (such as rabbits, dogs, cats, rats, mice, monkeys, cattle and humans). The form of preparations may be either oral preparations (such as powders, tablets, granules and capsules) or parenteral preparations (such as suppositories and injections). These preparations can be prepared by methods known in the art.

When the compounds are given parenterally, they are usually given in the solution form, for example, in the injection form. Although the dose varies depending upon the object to which the preparations are given, the organ to which they are given, the symptom, the route of administration, etc, it is advantageous that they are intravenously injected in the injection form in a dose of about 0.01 to about 100 mg/kg of body weight per operation time, preferably about 0.01 to about 50 mg/kg, and more preferably about 0.05 to about 20 mg/kg. When the compounds are given orally, they are given before surgery in a dose of about 5 mg to about 1 g/kg of body weight, and preferably about 10 to 100 mg/kg. The injections include hypodermic injections, intradermic injections, intramuscular injections and drip infusions, as well as intravenous injections. Such injections are prepared by methods known in the art, namely., by dissolving, suspending or emulsifying the compounds having antagonistic activity on endothelin receptors in aseptic aqueous or oily solutions. Aqueous solutions for injection include physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic surface active agents (for example, polysorbate 80 and HCO-50). Oily solutions include sesame oil and soybean oil, and may be used in combination with solubilizing adjuvants such as benzyl benzoate and benzyl alcohol. The preparations may further contain buffers (for example, phosphate buffer and sodium acetate buffer), soothing agents (for example, benzalkonium chloride and procaine hydrochloride), stabilizing agents (for example, human serum albumin and polyethylene glycol), preservatives (for example, benzyl alcohol and phenol), etc. The injections thus prepared are usually filled into appropriate ampuls. When the oral preparations such as powders, tablets, granules and capsules are prepared, pharmaceutically acceptable carriers may be incorporated therein. The carriers include excipients (for example, lactose and starch), lubricants (for example, magnesium stearate and talc), binders (for example, hydroxypropyl cellulose, hydroxypropylmethyl cellulose and macrogold) and disintegrators (starch and carboxymethyl cellulose calcium). Additives such as antiseptics (for example, benzyl alcohol, chlorobutanol, methyl p-hydroxybenzoate and propyl p-hydroxybenzoate), antioxidants, colorants and sweeteners can be further used as required.

EXAMPLES

The present invention will be described in more detail with the following Reference Example, Example and Preparation Examples. It is understood of course that they are not intended to limit the scope of the present invention. Compound (1) represented by cyclo(-D-Asp-AspR1)-Asp-D-Thg(2)-Leu-D-Trp-) which is used in Example 1 is a compound described in EP-A-0,528,312 mentioned above, and is only a typical example of the compounds having antagonistic activity on endothelin receptors used in the present invention. Other compounds having antagonistic activity on endothelin receptors can also be used similarly. In addition to Preparation Examples 1 to 4, the preparation examples described in the above-mentioned patent specifications, the disclosure of each of which are hereby incorporated by reference, disclosing the compounds having antagonistic activity on endothelin receptors can also be employed similarly.

Reference Example 1

Compound 1[cyclo(D-Asp-AspR1)-Asp-D-Thg(2)-Leu-D-Trp-)] (0.266 mole) was dissolved into 6 liter of methanol. 0.1 N aqueous sodium hydroxide (5.41 L) was added to the solution under ice cooling for 3 hours and 25 minutes with mixing. Methanol was distilled out from the resulting solution under reduced pressure. Purified water (5 L) was added to the residual solution, which was washed twice with ethyl acetate (5 L). The water layer was concentrated under reduced pressure to 11,341 g. The residual solution was adsorbed on a column filled with 15 L of Diaion HP-20 (Trade mark, Mitsubishi Kasei, Japan). After the column was washed with 45 L of purified water, elution was conducted by methanol-purified water (1:1 by volume). The desired fractions were collected and it was concentrated under reduced pressure to 1,265 g. Twenty gram of activated charcoal (Shirasagi P, Trade mark, Takeda Chemical Industries, Ltd., Japan) was added to the concentrate and the mixture was mixed at 25° C. for 30 minutes. The activated charcoal was filtered by Millipore Filter(0.5 µm, φ90 mm, Trade Mark, Millipore, USA) and washed with purified water (0.8 L). The filtrate and the wash was combined and freezed to obtain 230 g of disodium salt of the compound 1. Elementary analysis as $C_{45}H_{51}N_9O_{11}SNa_2 \cdot 3.8H_2O$:

Calculated: C 51.95; H 5.68; N 12.12; S 3.08; Na 4.42
Determined: C 52.11; H 6.02; N 12.16; S 3.02; Na 4.62 Na was determined by atomic absorption spectrophotometry.

Example 1

A rat hepatic injury model after ischemia-reperfusion was prepared with reference to the method of Koo et al.[1]) Wister rats (male) weighing 250 to 300 g which had been fasted (water drinking had been allowed freely) since a day before were used for the experiment. The rats were anesthetized with pentobarbital sodium (60 mg/kg, intraperitoneal administration), and maintained at a body temperature of 37° C. by the use of a thermostat. A polyethylene tube for medication and for venous blood sampling was inserted in the left artery of each rat. After intravenous administration of heparin (200 units/kg), the venous blood (about 1 ml, before ischemia) was collected. The rats were divided into three groups (a pseudo-operation group, a control group and a compound (1) group). Physiological saline was intravenously given to the pseudo-operation and control groups, and 3 mg/kg of the 2Na salts of compound (1) to the compound (1) group. The abdomen was dissected, and the right branching of the portal vein was separated and clipped to shut off a blood flow to the right lobe and the quadrate lobe of the liver (the control group and the compound (1) group). The pseudo-operation group was treated in a similar manner without the procedure of clipping. After hemostasis for 25 minutes, the clip was opened to reflow the blood, and the venous blood was collected again after one hour (one hour after reperfusion). GPT and GOT activities in the plasma of the venous blood collected was assayed by spectrophotometric method using a standard assay kit (GPT-UV test wako and GOT-UV test wako). The significance tests among the respective groups were conducted by using the Ryan's multiple test for values before ischemia and values at one hour after reperfusion, respectively, and the difference is regarded as significant at a significance level of 5%. Results are shown in Tables 1 and 2.

1) Koo et al., "Contribution of no-reflow phenomenon to hepatic injury after ischemia-reperfusion: evidence for a role for superoxide anion", *Hematology*, 15, 507–514 (1991)

TABLE 1

| GPT | n | Before ischemia (KU) | One hour after reperfusion (KU) |
|---|---|---|---|
| Pseudo-operation group (given physiological saline) | 5 | 19 ± 4 | 27 ± 7 |
| Control group (given physiological saline) | 5 | 27 ± 11 | 73 ± 29* |
| 2Na salt of Compound (1) (3 mg/kg) | 5 | 19 ± 3 | 34 ± 10 |

*P < 0.05 (VS) control group or 2Na salt of compound (1) group
KU: Karmen unit

TABLE 2

| GOT | n | Before ischemia (KU) | One hour after reperfusion (KU) |
|---|---|---|---|
| Pseudo-operation group (given physiological saline) | 5 | 71 ± 9 | 89 ± 5 |
| Control group (given physiological saline) | 5 | 84 ± 19 | 171 ± 72 |
| 2Na salt of Compound (1) (3 mg/kg) | 5 | 68 ± 5 | 98 ± 14 |

The figures in Tables indicate "mean value±standard error".

For GPT and GOT activities in the plasma before ischemia, no significant difference was observed among three groups, the pseudo-operation group, the control group and the compound (1) group. The GPT activity of the control group at one hour after reperfusion showed a significantly high value, compared with that of the pseudo-operation group. The GPT activity of the compound (1) group at one hour after reperfusion was nearly equal to that of the pseudo-operation group. The GOT activity of the control group at one hour after reperfusion was also higher than that of the pseudo-operation group, and intravenous administration of 3 mg/kg of the 2Na salt of compound (1) showed a tendency to inhibit an increase in GOT activity.

These results proved that compound (1) showed significant inhibiting action on an increase in plasma GPT value associated with a rat hepatic injury after ischemiareperfusion, and that it also showed a tendency to inhibit an increase in plasma GOT value. This suggests that endogenous endothelin is related to the hepatic injury after ischemia-reperfusion, and indicates that the compounds having antagonistic activity on endothelin receptors act as prophylactic and/or therapeutic drugs for the hepatic injury after ischemia-reperfusion.

Preparation Example 1

Fifty milligrams of the 2Na salt of compound (1) used in Example 1 was dissolved in 50 ml of distilled water for injection (listed in the Pharmacopeia of Japan), followed by addition of distilled water for injection (listed in the Pharmacopeia of Japan) to adjust the volume to 100 ml. This solution was filtered under sterilization conditions. Then, vials for injection were each charged with 1 ml portions of this solution under sterilization conditions, followed by lyophilization. Subsequently, the vials were sealed.

Preparation Example 2

Five hundred milligrams of the 2Na salt of compound (1) used in Example 1 was dissolved in 50 ml of distilled water for injection (listed in the Pharmacopeia of Japan), followed by addition of distilled water for injection (listed in the Pharmacopeia of Japan) to adjust the volume to 100 ml. This solution was filtered under sterilization conditions. Then, vials for injection were each charged with 1 ml portions of this solution under sterilization conditions, followed by lyophilization. Subsequently, the vials were sealed.

Preparation Example 3

Five grams of the 2Na salt of compound (1) used in Example 1 was dissolved in 50 ml of distilled water for injection (listed in the Pharmacopeia of Japan), followed by addition of distilled water for injection (listed in the Pharmacopeia of Japan) to adjust the volume to 100 ml. This solution was filtered under sterilization conditions. Then, vials for injection were each charged with 1 ml portions of this solution under sterilization conditions, followed by lyophilization. Subsequently, the vials were sealed.

Preparation Example 4

Fifteen grams of the 2Na salt of compound (1) used in Example 1 was dissolved in 50 ml of distilled water for injection (listed in the Pharmacopeia of Japan), followed by addition of distilled water for injection (listed in the Pharmacopeia of Japan) to adjust the volume to 100 ml. This solution was filtered under sterilization conditions. Then, vials for injection were each charged with 1 ml portions of this solution under sterilization conditions, followed by lyophilization. Subsequently, the vials were sealed.

What is claimed is:

1. A method of treating organ hypofunction in a host, said hypofunction being caused by ischemia due to surgery on said organ, said method comprising administering to said host an organ hypofunction treatment effective amount of cyclo(D-Asp-AspR1)-Asp-D-Thg(2)-Leu-D-Trp) or a pharmaceutically acceptable salt thereof, wherein AspR1) is aspartic acid β-4-phenylpiperazineamide and Thg(2) is 2-(2-thienyl)glycine and wherein said organ is selected from the group consisting of liver and kidney.

2. A method according to claim 1, wherein the organ is a liver.

3. A method according to claim 1, wherein the organ is a kidney.

4. A method of treating organ hypofunction in a host, said hypofunction being caused by ischemia due to surgery on said organ, said method comprising administering to said host an organ hypofunction treatment effective amount of disodium salt cyclo(D-Asp-AspR1)-Asp-D-Thg(2)-Leu-D-Trp), in which AspR1) is aspartic acid β-4-phenylpiperazineamide and Thg(2) is 2-(2-thienyl)glycine and wherein said organ is selected from the group consisting of liver and kidney.

5. A method according to claim 4, wherein the organ is a liver.

6. A method according to claim 4, wherein the organ is a kidney.

* * * * *